(12) United States Patent
Gregersen et al.

(10) Patent No.: US 12,023,080 B1
(45) Date of Patent: Jul. 2, 2024

(54) CANNULATED CONTINUOUS COMPRESSION SCREW

(71) Applicant: University of Utah Research Foundation, Salt Lake City, UT (US)

(72) Inventors: Colin S. Gregersen, Salt Lake City, UT (US); T. Wade Fallin, Hyde Park, UT (US); Charles L. Saltzman, Salt Lake City, UT (US); Chase Hagman, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/375,484

(22) Filed: Sep. 30, 2023

Related U.S. Application Data

(60) Provisional application No. 63/534,817, filed on Aug. 26, 2023.

(51) Int. Cl.
| | | |
|---|---|---|
| *A61B 17/86* | (2006.01) | |
| *A61B 17/00* | (2006.01) | |
| *A61B 17/56* | (2006.01) | |
| *A61B 17/68* | (2006.01) | |

(52) U.S. Cl.
CPC ........ *A61B 17/866* (2013.01); *A61B 17/8605* (2013.01); *A61B 17/863* (2013.01); *A61B 17/8635* (2013.01); *A61B 17/864* (2013.01); *A61B 17/8685* (2013.01); *A61B 2017/00867* (2013.01); *A61B 2017/564* (2013.01); *A61B 2017/681* (2013.01)

(58) Field of Classification Search
CPC . A61B 17/864; A61B 17/866; A61B 17/7225; A61B 17/8685
See application file for complete search history.

(56) References Cited

U.S. PATENT DOCUMENTS

| | | | |
|---|---|---|---|
| 2,077,804 | A | 4/1937 | Morrison |
| 2,397,545 | A | 4/1946 | Hardinge |
| 3,051,169 | A | 8/1962 | Leonard |
| 4,456,005 | A | 6/1984 | Lichty |
| 4,940,467 | A | 7/1990 | Tronzo |
| 4,947,502 | A | 8/1990 | Engelhardt |
| 4,959,064 | A | 9/1990 | Engelhardt |

(Continued)

FOREIGN PATENT DOCUMENTS

| | | |
|---|---|---|
| EM | 0015671160002 S | 7/2009 |
| WO | WO 2019113115 A1 | 6/2019 |

OTHER PUBLICATIONS

U.S. Appl. No. 10/085,775, filed Oct. 2, 2018, Markku Biedermann.
(Continued)

*Primary Examiner* — Olivia C Chang
(74) *Attorney, Agent, or Firm* — David Meibos; Maywood IP Law

(57) ABSTRACT

A bone screw may be insertable into a bone. The bone screw may have a distal member with bone-engaging threads, a proximal member configured to slidably engage the distal member, and a tension member with a proximal end coupled to the proximal member, and a distal end coupled to the distal member such that, in response to motion of the distal member away from the proximal member, the tension member elongates and urges the distal member to move toward the proximal member.

14 Claims, 35 Drawing Sheets

(56) References Cited

U.S. PATENT DOCUMENTS

| | | |
|---|---|---|
| 5,061,137 A | 10/1991 | Gourd |
| 5,067,957 A | 11/1991 | Jervis |
| 5,102,276 A | 4/1992 | Gourd |
| 5,122,133 A | 6/1992 | Evans |
| 5,305,203 A | 4/1994 | Raab |
| 5,415,660 A | 5/1995 | Campbell |
| 5,827,285 A | 10/1998 | Bramlet |
| 5,876,434 A | 3/1999 | Flomenblit |
| 6,021,343 A | 2/2000 | Foley |
| 6,190,395 B1 | 2/2001 | Williams |
| 6,296,645 B1 | 10/2001 | Hover |
| 6,468,202 B1 | 10/2002 | Irion |
| 6,478,802 B2 | 11/2002 | Kienzle, III |
| 6,511,481 B2 | 1/2003 | von Hoffmann et al. |
| 6,656,184 B1 | 12/2003 | White |
| 6,725,080 B2 | 4/2004 | Melkent |
| 6,736,819 B2 | 5/2004 | Tipirneni |
| 6,887,243 B2 | 5/2005 | Culbert |
| 6,887,245 B2 | 5/2005 | Kienzle, III |
| 6,908,275 B2 | 6/2005 | Nelson |
| 6,908,465 B2 | 6/2005 | von Hoffmann et al. |
| 7,175,626 B2 | 2/2007 | Neff |
| 7,582,107 B2 | 9/2009 | Trail et al. |
| 7,625,395 B2 | 12/2009 | Muckter |
| D611,145 S | 3/2010 | Khalil |
| D611,225 S | 3/2010 | Khalil |
| D625,818 S | 10/2010 | Khalil |
| 7,877,890 B2 | 2/2011 | Weber |
| 7,881,770 B2 | 2/2011 | Melkent |
| 7,901,412 B2 | 3/2011 | Tipirneni |
| 7,905,908 B2 | 3/2011 | Cragg |
| 7,985,222 B2 | 7/2011 | Gall |
| 8,043,333 B2 | 10/2011 | Frigg |
| 8,048,134 B2 | 11/2011 | Partin |
| 8,066,748 B2 | 11/2011 | Lieberman |
| 8,114,141 B2 | 2/2012 | Appenzeller |
| 8,118,952 B2 | 2/2012 | Gall |
| D657,873 S | 4/2012 | Khalil |
| 8,216,243 B2 | 7/2012 | Yevmenenko et al. |
| 8,216,398 B2 | 7/2012 | Bledsoe |
| 8,460,349 B2 | 6/2013 | Frenk et al. |
| 8,491,583 B2 | 7/2013 | Gall |
| 8,540,726 B2 | 9/2013 | Yevmenenko et al. |
| 8,551,106 B2 | 10/2013 | Harrold |
| 8,556,969 B2 | 10/2013 | Johnson |
| 8,597,337 B2 | 12/2013 | Champagne |
| 8,679,167 B2 | 3/2014 | Tipirneni |
| 8,690,931 B2 | 4/2014 | Appenzeller |
| 8,702,768 B2 | 4/2014 | Tipirneni |
| 8,828,067 B2 | 9/2014 | Tipirneni |
| 8,864,804 B2 | 10/2014 | Champagne |
| 8,876,821 B2 | 11/2014 | Kinmon |
| 8,961,500 B2 | 2/2015 | DiCorleto |
| 9,028,534 B2 | 5/2015 | Tipirneni |
| 9,050,108 B2 | 6/2015 | Grinberg |
| 9,060,809 B2 | 6/2015 | Tipirneni et al. |
| 9,060,824 B2 | 6/2015 | Chien |
| 9,113,976 B2 | 8/2015 | Yevmenenko et al. |
| 9,138,274 B1 | 9/2015 | Biesinger |
| 9,161,793 B2 | 10/2015 | Huebner |
| 9,161,799 B2 | 10/2015 | Benson |
| 9,168,076 B2 | 10/2015 | Patty |
| 9,204,910 B2 | 12/2015 | Epperly |
| 9,283,006 B2 | 3/2016 | Fonte |
| 9,326,805 B2 | 5/2016 | Biedermann |
| 9,339,316 B2 | 5/2016 | Hulliger |
| 9,345,514 B2 | 5/2016 | Robinson |
| 9,364,275 B2 | 6/2016 | Pacheco et al. |
| 9,414,875 B2 | 8/2016 | Appenzeller |
| 9,482,260 B1 | 11/2016 | Krause |
| 9,498,229 B2 | 11/2016 | Harris, Jr. et al. |
| 9,522,019 B2 | 12/2016 | Biedermann |
| 9,539,372 B2 | 1/2017 | Johnson |
| 9,615,869 B2 | 4/2017 | Brown et al. |
| 9,638,491 B2 | 5/2017 | Challis |
| 9,724,138 B2 | 8/2017 | Palmer |
| 9,724,149 B2 | 8/2017 | Trieu |
| 9,763,712 B2 | 9/2017 | Appenzeller |
| 9,795,412 B2 | 10/2017 | Sinha |
| 9,827,029 B2 | 11/2017 | Hulliger |
| 9,861,413 B2 | 1/2018 | Palmer |
| 9,861,415 B2 | 1/2018 | Biedermann |
| 9,872,712 B2 | 1/2018 | Trieu |
| 9,980,762 B2 | 5/2018 | Anapliotis |
| 10,064,670 B2 | 9/2018 | Mootien et al. |
| 10,166,056 B2 | 1/2019 | Warren et al. |
| 10,219,850 B2 | 3/2019 | Fumex et al. |
| 10,531,905 B2 | 1/2020 | Gault et al. |
| 10,702,324 B2 | 7/2020 | Marek et al. |
| 10,856,924 B2 | 12/2020 | Rippe et al. |
| 11,278,335 B2 | 3/2022 | Rowe et al. |
| 11,291,488 B1 | 4/2022 | O'Flaherty et al. |
| 11,452,556 B2 | 9/2022 | Rippe et al. |
| 2002/0198527 A1 | 12/2002 | Muckter |
| 2004/0171930 A1 | 9/2004 | Grimm |
| 2005/0131411 A1 | 6/2005 | Culbert |
| 2005/0154296 A1 | 7/2005 | Lechner |
| 2005/0240190 A1 | 10/2005 | Gall |
| 2006/0015207 A1 | 1/2006 | Weiser |
| 2006/0264954 A1 | 11/2006 | Sweeney, II et al. |
| 2007/0260248 A1 | 11/2007 | Tipirneni |
| 2009/0198287 A1 | 8/2009 | Chiu |
| 2009/0254129 A1 | 10/2009 | Tipirneni |
| 2009/0264937 A1 | 10/2009 | Parrott |
| 2010/0076498 A1 | 3/2010 | Tyber |
| 2010/0211115 A1 | 8/2010 | Tyber et al. |
| 2010/0268285 A1 | 10/2010 | Tipirneni et al. |
| 2010/0312245 A1 | 12/2010 | Tipirneni et al. |
| 2011/0004212 A1 | 1/2011 | Gall |
| 2011/0077693 A1 | 3/2011 | Yu |
| 2011/0203406 A1 | 8/2011 | Macintyre |
| 2011/0295319 A1 | 12/2011 | Duplessis |
| 2013/0253593 A1 | 9/2013 | Fierlbeck |
| 2013/0310835 A1 | 11/2013 | Gall |
| 2014/0121714 A1 | 5/2014 | Hernandez |
| 2014/0142639 A1 | 5/2014 | Vennard et al. |
| 2014/0257420 A1 | 9/2014 | Fox |
| 2015/0223843 A1 | 8/2015 | Tipirneni |
| 2015/0250515 A1 | 9/2015 | Terrill et al. |
| 2015/0257797 A1 | 9/2015 | Biedermann et al. |
| 2015/0366591 A1 | 12/2015 | Dujovne |
| 2016/0015440 A1 | 1/2016 | Patty |
| 2016/0038203 A1 | 2/2016 | Huebner |
| 2016/0143649 A1 | 5/2016 | Weekes |
| 2016/0183992 A1 | 6/2016 | Huang |
| 2016/0249964 A1 | 9/2016 | Songer et al. |
| 2016/0287301 A1 | 10/2016 | Mehl et al. |
| 2017/0296245 A1 | 10/2017 | Gault et al. |
| 2018/0071000 A1 | 3/2018 | Pham |
| 2018/0092677 A1 | 4/2018 | Peterson |
| 2018/0206897 A1 | 7/2018 | Palmer |
| 2018/0263669 A1 | 9/2018 | Peterson |
| 2018/0311051 A1 | 11/2018 | Donaldson |
| 2018/0317989 A1 | 11/2018 | Sellers |
| 2019/0298427 A1 | 10/2019 | Palmer |
| 2019/0374269 A1 | 12/2019 | Kiefer et al. |
| 2020/0038080 A1 | 2/2020 | Palmer |
| 2020/0261121 A1 | 8/2020 | Biedermann |
| 2020/0305938 A1 | 10/2020 | Krumme |
| 2021/0030455 A1 | 2/2021 | Patty |
| 2022/0142691 A1 | 5/2022 | Smith |
| 2022/0175430 A1 | 6/2022 | Rowe et al. |
| 2022/0218400 A1 | 7/2022 | Krumme et al. |
| 2022/0265332 A1* | 8/2022 | O'Flaherty .......... A61B 17/864 |
| 2022/0280197 A1 | 9/2022 | Blair et al. |

OTHER PUBLICATIONS

U.S. Appl. No. 10/117,695, filed Nov. 6, 2018, Lutz Biedermann.
U.S. Appl. No. 10/130,358, filed Nov. 20, 2018, Matthew Palmer.
U.S. Appl. No. 10/136,930, filed Nov. 27, 2018, William R. Krause.
U.S. Appl. No. 10/166,055, filed Jan. 1, 2019, Jeremy Eekhoff.
U.S. Appl. No. 10/194,946, filed Feb. 5, 2019, Kathryn A. Stecco.

(56) References Cited

OTHER PUBLICATIONS

U.S. Appl. No. 10/292,735, filed May 21, 2019, Dror Robinson.
U.S. Appl. No. 10/327,826, filed Jun. 25, 2019, Charles Horrell.
U.S. Appl. No. 10/405,903, filed Sep. 10, 2019, David P Biesinger.
U.S. Appl. No. 10/478,238, filed Nov. 19, 2019, Andrew K. Palmer.
U.S. Appl. No. 10/555,766, filed Feb. 11, 2020, Kathryn A. Stecco.
U.S. Appl. No. 10/610,266, filed Apr. 7, 2020, Markku Biedermann.
U.S. Appl. No. 10/610,276, filed Apr. 7, 2020, Christian Lutz.
U.S. Appl. No. 10/751,101, filed Aug. 25, 2020, Lutz Biedermann.
U.S. Appl. No. 10/806,497, filed Oct. 20, 2020, Robert Michael Patty.
U.S. Appl. No. 10/883,532, filed Jan. 5, 2021, William R. Krause.
U.S. Appl. No. 10/898,249, filed Jan. 26, 2021, Matthew Palmer.
U.S. Appl. No. 11/020,158, filed Jun. 1, 2021, Scott Epperly.
Smith & Nephew, Conquest FN Femoral Neck Fracture System, brochure 2018 (8 pgs).
Medshape, DynaNail Mini Fusion System, The Compression Standard by which Fusion Systems are measured just got smaller, Brochure 2019 (2 pgs).
Medshape, DynaNail Mini Fusion System, Dynaframe CF Deployment System, 2017 (2 pgs).
Medshape, Enovis, Dynanail Helix, Nail System sales sheet, 2022 (2 pgs).
Medline, United Foot & Ankle: Reflex Nitinol Dynamic Disc: A Novel Concept for Screw Dynamization, 2022 1 pg.
Activortho, NiTE Force Compression Implant 2023 (retrieved from: https://activortho.com/#technology) (6 pgs).

* cited by examiner

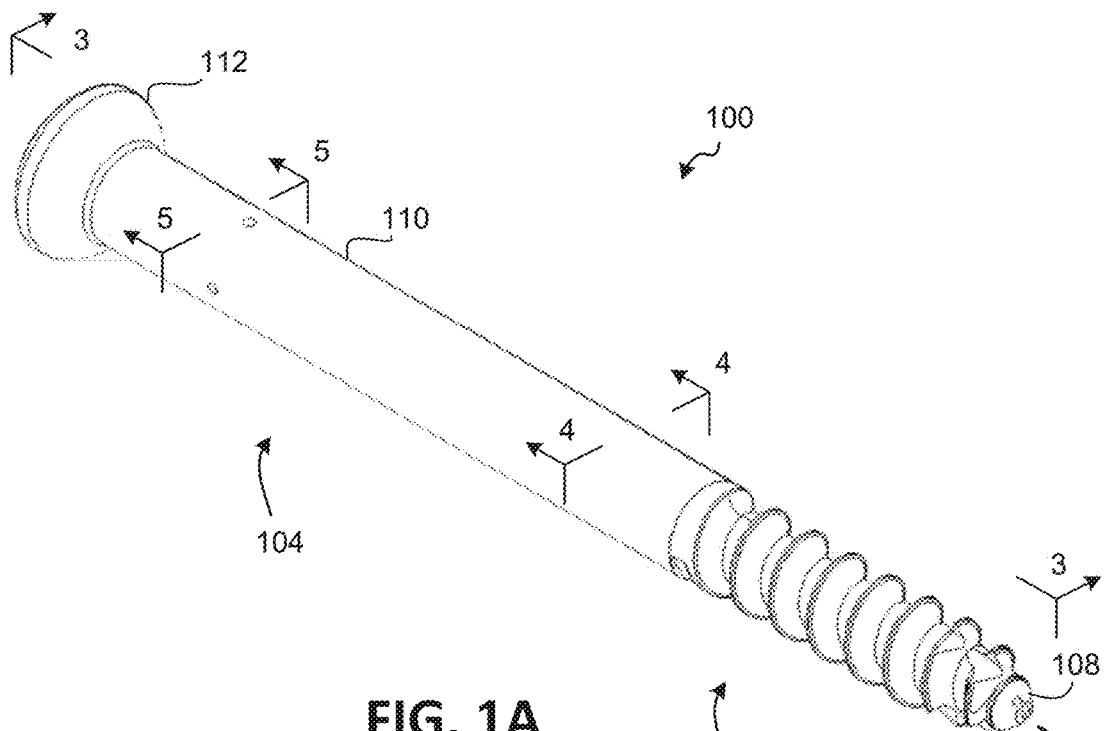
FIG. 1A
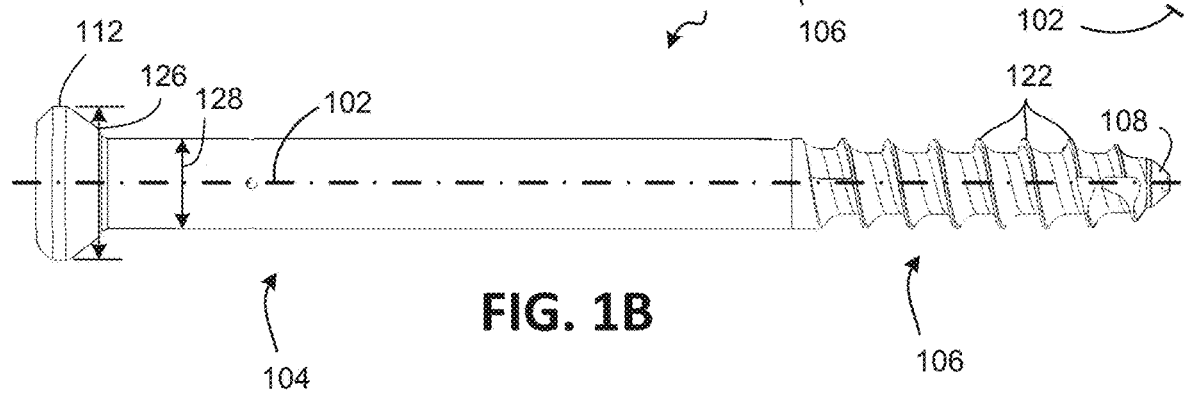
FIG. 1B
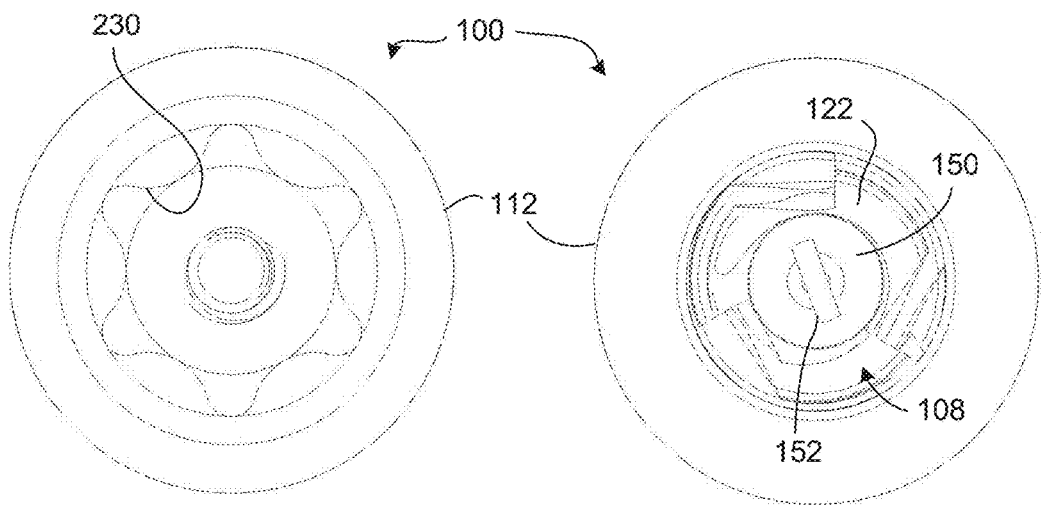
FIG. 1C
FIG. 1D

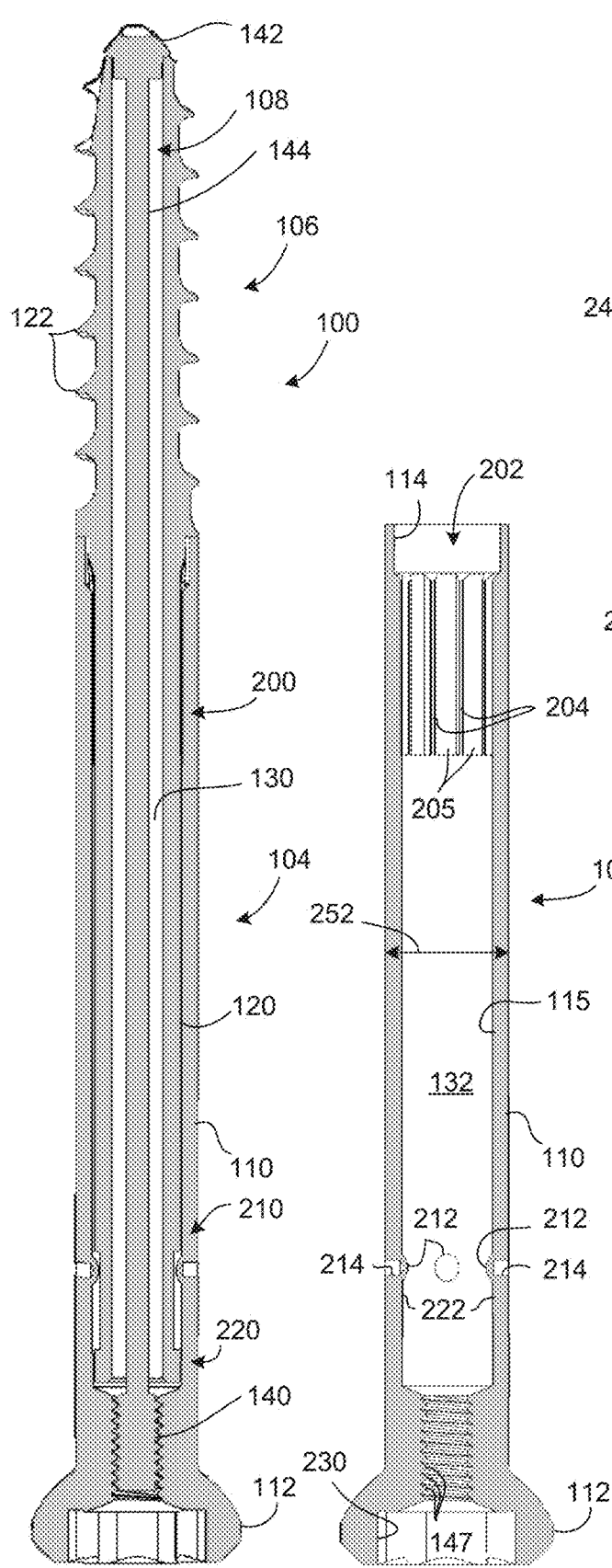
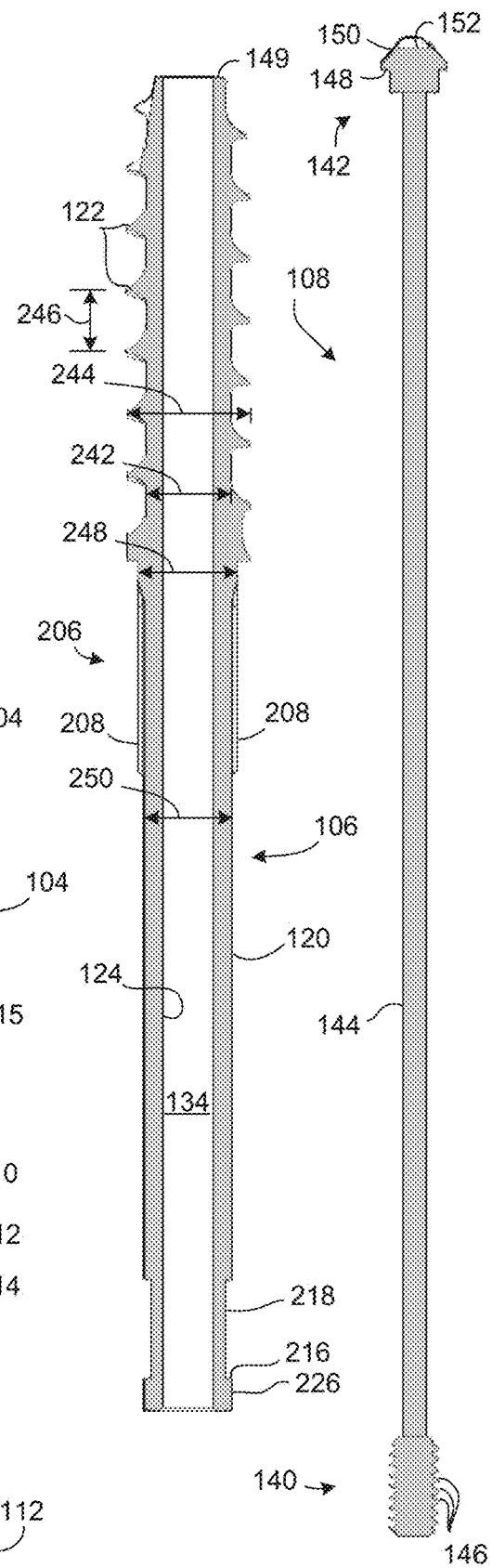
FIG. 3A  FIG. 3B  FIG. 3C  FIG. 3D

CANNULATED CONTINUOUS COMPRESSION SCREW

CROSS-REFERENCE TO RELATED APPLICATIONS

This application claims priority to U.S. Provisional Application No. 63/534,817, filed on Aug. 26, 2023, entitled "Cannulated Continuous Compression Screw", which is incorporated by reference as though set forth herein in its entirety.

TECHNICAL FIELD

The present disclosure relates to bone fixation devices, systems, and methods. More specifically, the present disclosure relates to bone screws that can apply compressive force to surrounding bone.

BACKGROUND

Surgical procedures involving fixation of bone portions with bone screws and fasteners can fail or become loose over time due to bending loads, multi-axial forces, and/or off-axis loading scenarios that may be applied to the bone screws during the healing process. Existing bone screws and fasteners may not provide sufficient fixation and strength to overcome these bending loads, multi-axial forces, and/or off-axis loading scenarios.

Further, it has been observed that healing of fractures, fusion of bone portions, and other forms of osteogenesis are facilitated by pressure applied across the bone interface. Existing bone fixation systems often provide pressure when initially applied, but then this pressure subsides over time due to subsidence, resorption, motion of the bone portions involved, loosening of the fastener, and/or other factors.

Accordingly, bone fixation devices, systems, and methods with improved fixation, strength, and bone loading characteristics would be desirable.

SUMMARY

The various bone fixation devices, systems, and methods of the present disclosure have been developed in response to the present state of the art, and in particular, in response to the problems and needs in the art that have not yet been fully solved by currently available bone fixation devices, systems, and methods. In some embodiments, the bone fixation devices, systems, and methods of the present disclosure may provide improved bone fixation and stabilization between two or more bone portions and/or implants.

In one embodiment, a bone screw, insertable into a bone, may have a distal member with bone-engaging threads and a driver engagement feature configured to mate with a driver to receive torque directly from the driver. The bone screw may also have a proximal member configured to slidably engage the distal member, and a tension member. The tension member may have a proximal end coupled to the proximal member, and a distal end coupled to the distal member such that, in response to motion of the distal member away from the proximal member, the tension member elongates and urges the distal member to move toward the proximal member.

In the bone screw of any preceding paragraph, the tension member may further have a shaft extending from the proximal end to the distal end. The shaft may have a cannula sized to receive a guidewire.

In the bone screw of any preceding paragraph, the proximal member may have a shank and a head comprising head threading with a first pitch different from a second pitch of the bone-engaging threads.

In the bone screw of any preceding paragraph, the proximal member and the distal member may define a longitudinal axis, and the proximal member may have a shank and a head with a proximal-most surface that is nonperpendicular to the longitudinal axis.

In the bone screw of any preceding paragraph, the proximal member and the distal member may define a longitudinal axis. The distal member may have a distal engagement surface facing away from the longitudinal axis. The proximal member may have a proximal engagement surface facing toward the longitudinal axis. The distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member. The proximal member and the distal member may cooperate to define a length limiting mechanism configured to prevent the length from exceeding a maximum length, and prevent the length from decreasing below a minimum length.

In the bone screw of any preceding paragraph, the proximal member may have a proximal opening through which a driver is insertable to engage the driver engagement feature.

In the bone screw of any preceding paragraph, the driver engagement feature may have a slot shaped to receive a blade-shaped torque output feature of a driver.

In the bone screw of any preceding paragraph, the proximal member may further be configured to rotatably engage the distal member.

In the bone screw of any preceding paragraph, the bone screw may have a length from a proximal-most end of the proximal member to a distal-most end of the distal member. The proximal member may have a proximal shaft with a proximal shaft width. The distal member may have a distal shaft with a distal shaft width. At each of a minimum length and a maximum length of the bone screw, the distal shaft may have a constant cross-sectional shape from a distal-most end of the proximal member to a proximal-most end of the bone-engaging threads.

In one embodiment, a bone screw, insertable into a bone, may have a distal member with bone-engaging threads, a proximal member configured to slidably and rotatably engage the distal member, and a tension member with a proximal end coupled to the proximal member, and a distal end coupled to the distal member such that, in response to motion of the distal member away from the proximal member, the tension member elongates and urges the distal member to move toward the proximal member.

In the bone screw of any preceding paragraph, the tension member may further have a shaft extending from the proximal end to the distal end. The shaft may have a cannula sized to receive a guidewire.

In the bone screw of any preceding paragraph, the proximal member may have a shank and a head with head threading with a first pitch different from a second pitch of the bone-engaging threads.

In the bone screw of any preceding paragraph, the proximal member and the distal member may define a longitudinal axis, and the proximal member may have a shank and a head with a proximal-most surface that is nonperpendicular to the longitudinal axis.

In the bone screw of any preceding paragraph, the proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the bone screw of any preceding paragraph, the bone screw may have a length from a proximal-most end of the proximal member to a distal-most end of the distal member, the proximal member may have a proximal shaft with a proximal shaft width, the distal member may have a distal shaft with a distal shaft width, and at each of a minimum length and a maximum length of the bone screw, the distal shaft may have a constant cross-sectional shape from a distal-most end of the proximal member to a proximal-most end of the bone-engaging threads.

In one embodiment, a bone screw, insertable into a bone, may have a distal member with bone-engaging threads, a proximal member configured to slidably engage the distal member to cause the bone screw to have a minimum length and a maximum length that is greater than the minimum length, and a tension member. The tension member may have a proximal end coupled to the proximal member, and a distal end coupled to a distal end of the distal member such that, in response to motion of the distal member away from the proximal member, the tension member elongates and urges the distal member to move toward the proximal member. The proximal member may have a proximal shaft with a proximal shaft width, the distal member may have a distal shaft with a distal shaft width, and at each of the minimum length and the maximum length, the distal shaft may have a constant cross-sectional shape from a distal-most end of the proximal member to a proximal-most end of the bone-engaging threads.

In the bone screw of any preceding paragraph, the tension member may further have a shaft extending from the proximal end to the distal end. The shaft may have a cannula sized to receive a guidewire.

In the bone screw of any preceding paragraph, the proximal member may have a shank and a head with head threading with a first pitch different from a second pitch of the bone-engaging threads.

In the bone screw of any preceding paragraph, the proximal member and the distal member may define a longitudinal axis, and the proximal member may have a shank and a head with a proximal-most surface that is nonperpendicular to the longitudinal axis.

In the bone screw of any preceding paragraph, the proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

According on one embodiment, a bone screw, insertable into a bone, may have a distal member with bone-engaging threads, a proximal member configured to slidably engage the distal member, and a tension member. The tension member may have a proximal end coupled to the proximal member, and a distal end coupled to the distal member such that, in response to motion of the distal member away from the proximal member, the tension member elongates and urges the distal member to move toward the proximal member. The proximal member may have a head configured to resist insertion into the bone such that distal motion of the bone-engaging threads within the bone causes elongation of the tension member, and the distal member and the proximal member may cooperate to define a driver engagement feature configured to mate with a pre-stretch driver such that the pre-stretch driver is actuatable to urge the proximal member to move proximally relative to the distal member to cause elongation of the tension member independently of engagement of the bone screw with the bone.

In the bone screw of any preceding paragraph, the tension member may further have a shaft extending from the proximal end to the distal end. The shaft may have a cannula sized to receive a guidewire.

In the bone screw of any preceding paragraph, the proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the bone screw of any preceding paragraph, the driver engagement feature may have a push feature on the distal member, configured to engage the pre-stretch driver in a manner that allows the push feature to be pushed distally by the pre-stretch driver, and a retention feature on the proximal member, configured to engage the pre-stretch driver in a manner that allows the retention feature to remain in place while the push feature advances distally.

In the bone screw of any preceding paragraph, the push feature may have a slot formed on a proximal surface of the distal member, and the retention feature may have an internal groove formed on an interior surface of the proximal member.

In the bone screw of any preceding paragraph, the push feature may be shaped to be rotatable by the pre-stretch driver to enable the pre-stretch driver to rotate the distal member independently of the proximal member during insertion of the bone screw into bone, causing the bone screw to elongate beyond a pre-stretch level induced by the pre-stretch driver.

In the bone screw of any preceding paragraph, the push feature may have a slot shaped to receive a blade-shaped torque output feature of the pre-stretch driver.

According to one embodiment, a system may provide compression within a bone, and may have a bone screw with a distal member with bone-engaging threads, a proximal member resiliently coupled to and configured to slidably engage the distal member, and a pre-stretch driver configured to urge elongation of the bone screw. The pre-stretch driver may have a sleeve configured to engage the proximal member and a driver shaft slidably retained within the sleeve. The driver shaft may be configured to engage the distal member. The pre-stretch driver may further have an actuator configured to urge the driver shaft to move distally relative to the sleeve to urge the distal member to move distally relative to the proximal member.

In the system of any preceding paragraph, the bone screw may further have a tension member with a proximal end coupled to the proximal member, a distal end coupled to the distal member such that, in response to motion of the distal member away from the proximal member, the tension member elongates and urges the distal member to move toward the proximal member, and a shaft extending from the proximal end to the distal end. The shaft may have a cannula sized to receive a guidewire.

In the system of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the system of any preceding paragraph, the proximal member and the distal member may cooperate to define a driver engagement feature with a push feature on the distal member, configured to engage the pre-stretch driver in a manner that allows the push feature to be pushed distally by the pre-stretch driver, and a retention feature on the proximal member, configured to engage the pre-stretch driver in a manner that allows the retention feature to remain in place while the push feature advances distally.

In the system of any preceding paragraph, the push feature may have a slot formed on a proximal surface of the distal member, and the retention feature may have an internal groove formed on an interior surface of the proximal member.

In the system of any preceding paragraph, the push feature may be shaped to be rotatable by the pre-stretch driver to enable the pre-stretch driver to rotate the distal member independently of the proximal member during insertion of the bone screw into bone, causing the bone screw to elongate beyond a pre-stretch level induced by the pre-stretch driver.

In the system of any preceding paragraph, the pre-stretch driver may further have a blade-shaped torque output feature, and the push feature may have a slot shaped to receive the blade-shaped torque output feature.

In the system of any preceding paragraph, the pre-stretch driver may further have a proximal end with a torque input feature that facilitates rotation of the pre-stretch driver, while coupled to the bone screw in a pre-stretched condition.

In the system of any preceding paragraph, the actuator may be configured to be rotated by hand to urge the distal member to move distally relative to the proximal member, and the pre-stretch driver may further have a scale positioned to indicate a level of elongation of the bone screw by visual comparison of the scale with a position of the actuator.

According to one embodiment, a system, for providing compression within a bone, may have a bone screw with a distal member with bone-engaging threads, a proximal member resiliently coupled to and configured to slidably engage the distal member, and a pre-stretch driver configured to urge elongation of the bone screw. The pre-stretch driver may have an actuator configured to be rotated by hand to urge the distal member to move distally relative to the proximal member, and a scale positioned to indicate a level of elongation of the bone screw by visual comparison of the scale with a position of the actuator.

In the system of any preceding paragraph, the bone screw may further have a tension member with a proximal end coupled to the proximal member, a distal end coupled to the distal member such that, in response to motion of the distal member away from the proximal member, the tension member elongates and urges the distal member to move toward the proximal member, and a shaft extending from the proximal end to the distal end, the shaft with a cannula sized to receive a guidewire.

In the system of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the system of any preceding paragraph, the proximal member and the distal member may cooperate to define a driver engagement feature with a push feature on the distal member, configured to engage the pre-stretch driver in a manner that allows the push feature to be pushed distally by the pre-stretch driver, and a retention feature on the proximal member, configured to engage the pre-stretch driver in a manner that allows the retention feature to remain in place while the push feature advances distally.

In the system of any preceding paragraph, the push feature may have a slot formed on a proximal surface of the distal member, the retention feature may have an internal groove formed on an interior surface of the proximal member, and the push feature may be shaped to be rotatable by the pre-stretch driver to enable the pre-stretch driver to rotate the distal member independently of the proximal member during insertion of the bone screw into bone, causing the bone screw to elongate beyond a pre-stretch level induced by the pre-stretch driver.

In the system of any preceding paragraph, the pre-stretch driver further may have a proximal end with a torque input feature that facilitates rotation of the pre-stretch driver, while coupled to the bone screw in a pre-stretched condition.

In one embodiment, a bone screw, insertable into a bone, may have a distal member with bone-engaging threads, a proximal member configured to slidably engage the distal member, and a tension member coupled to the proximal member and the distal member such that, in response to motion of the distal member away from the proximal member, the tension member elongates and urges the distal member to move toward the proximal member. The tension member may be configured such that, at a minimum length of the bone screw, the tension member is pre-stretched so that the tension member is under tension to urge the bone screw to shorten.

In the bone screw of any preceding paragraph, the tension member may further have a shaft extending from a proximal end to a distal end of the tension member. The shaft may have a cannula sized to receive a guidewire.

In the bone screw of any preceding paragraph, the proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below the minimum length.

In the bone screw of any preceding paragraph, the tension member may be configured to be tensioned after the tension member has been coupled to the proximal member and the distal member.

In the bone screw of any preceding paragraph, the bone screw may further have a nut with interior threads. One of a proximal end and a distal end of the tension member may have threads configured to engage the interior threads of the nut to couple the tension member to one of the proximal member and the distal member.

In the bone screw of any preceding paragraph, the threads may be on the distal end of the tension member, the nut may be shaped to abut a corresponding surface of the distal member, the tension member may be dimensioned to be couplable to the distal member via the nut with the proximal member and the distal member at the minimum length, and the nut may be configured to be further actuated after the tension member has been coupled to the distal member via the nut to pre-stretch the tension member with the bone screw at the minimum length.

In one embodiment, a method, for inserting a bone screw into a bone, may include positioning the bone screw proximate the bone. The bone screw may have a distal member with bone-engaging threads, a proximal member configured to slidably engage the distal member, and a tension member coupled to the proximal member and the distal member such that, in response to motion of the distal member away from the proximal member, the tension member elongates and urges the distal member to move toward the proximal member. The method may further include, with the bone screw at a minimum length, stretching the tension member to move the tension member from a relaxed state to a stretched state, and with the tension member in the stretched state, inserting the bone screw into the bone.

In the method of any preceding paragraph, the tension member may further have a shaft extending from a proximal end to a distal end of the tension member. The shaft may have a cannula. Inserting the bone screw into the bone may include inserting the bone screw over a guidewire placed in the bone such that the cannula receives the guidewire.

In the method of any preceding paragraph, the method may further include, prior to positioning the bone screw proximate the bone, coupling the tension member to the proximal member and the distal member, and with the tension member coupled to the proximal member and the distal member and with the tension member at the minimum length, tensioning the tension member.

In the method of any preceding paragraph, the bone screw may further have a nut with interior threads, one of a proximal end and a distal end of the tension member may have threads, and coupling the tension member to the proximal member and the distal member may include engaging the interior threads of the nut with the threads of the tension member to couple the tension member to one of the proximal member and the distal member.

In the method of any preceding paragraph, the threads may be on the distal end of the tension member, coupling the tension member to the proximal member and the distal member may further include, with the proximal member and the distal member at the minimum length, abutting a corresponding surface of the distal member with the nut, and tensioning the tension member may include, with the bone screw at the minimum length, further actuating the nut after coupling the tension member to the distal member via the nut to pre-stretch the tension member.

According to one embodiment, bone screw, insertable into a bone, may have a distal member with bone-engaging threads, a proximal member configured to slidably engage the distal member to cause the bone screw to have a minimum length and a maximum length that is greater than the minimum length, and a tension member coupled to the proximal member and the distal member such that, in response to motion of the distal member away from the proximal member, the tension member elongates and urges the distal member to move toward the proximal member. The tension member may be at least partially formed of a superelastic material having an upper plateau stress and a lower plateau stress. The tension member may impart a first compressive force between the proximal member and the distal member when the tension member is at the minimum length and a second compression force between the proximal member and the distal member when the tension member is at the maximum length. The first compression force divided by the second compression force may be similar in value to the lower plateau stress divided by the upper plateau stress.

In the bone screw of any preceding paragraph, the tension member may further have a shaft extending from a proximal end to a distal end of the tension member. The shaft may have a cannula sized to receive a guidewire.

In the bone screw of any preceding paragraph, the proximal member may have a shank and a head with head threading with a first pitch different from a second pitch of the bone-engaging threads.

In the bone screw of any preceding paragraph, the proximal member and the distal member may define a longitudinal axis, and the proximal member may have a shank and a head with a proximal-most surface that is nonperpendicular to the longitudinal axis.

In the bone screw of any preceding paragraph, the proximal member and the distal member define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the bone screw of any preceding paragraph, the maximum length may be selected such that, at the maximum length, the tension member is at the upper plateau stress, and the minimum length may be selected such that, at the minimum length, the tension member is at the lower plateau stress.

In the bone screw of any preceding paragraph, the tension member may be configured such that, at a minimum length of the bone screw, the tension member is pre-stretched so that the tension member is under tension to urge the bone screw to shorten.

In the bone screw of any preceding paragraph, the tension member may further be configured to have the upper plateau stress at a first temperature and to have a second lower plateau stress at a second temperature higher than the first temperature. The upper plateau stress may be similar in value to the second lower plateau stress.

In one embodiment, a bone screw, insertable into a bone, may have a distal member with bone-engaging threads, a proximal member configured to slidably engage the distal member to cause the bone screw to have a minimum length and a maximum length that is greater than the minimum length, and a tension member coupled to the proximal member and the distal member such that, in response to motion of the distal member away from the proximal member, the tension member elongates and urges the distal member to move toward the proximal member. The tension member may be at least partially formed of a superelastic material having an upper plateau stress at a first temperature and a lower plateau stress at a second temperature. The second temperature may be higher than the first temperature. The upper plateau stress may be similar in value to the lower plateau stress.

In the bone screw of any preceding paragraph, the tension member may further have a shaft extending from a proximal end to a distal end of the tension member. The shaft may have a cannula sized to receive a guidewire.

In the bone screw of any preceding paragraph, the proximal member may have a shank and a head with head threading with a first pitch different from a second pitch of the bone-engaging threads.

In the bone screw of any preceding paragraph, the proximal member and the distal member define a longitudinal axis, and the proximal member may have a shank and a head with a proximal-most surface that is nonperpendicular to the longitudinal axis.

In the bone screw of any preceding paragraph, the proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmission of torque about the longitudinal axis between the distal engagement surface and the proximal engagement surface.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the bone screw of any preceding paragraph, the maximum length may be selected such that, at the maximum length, the tension member is at the upper plateau stress, and the minimum length may be selected such that, at the minimum length, the tension member is at the lower plateau stress.

In the bone screw of any preceding paragraph, the tension member may be configured such that, at a minimum length of the bone screw, the tension member is pre-stretched so that the tension member is under tension to urge the bone screw to shorten.

In the bone screw of any preceding paragraph, the second temperature may be an internal body temperature of a patient.

According to one embodiment, a method for inserting a bone screw into a bone may include positioning the bone screw proximate the bone. The bone screw may have a distal member with bone-engaging threads, a proximal member configured to slidably engage the distal member, and a tension member configured to be coupled to the proximal member and the distal member such that, in response to motion of the distal member away from the proximal member, the tension member elongates and urges the distal member to move toward the proximal member. The method may further include, with the tension member at a first temperature, coupling the tension member to the proximal member and the distal member, and moving the tension member to a second temperature different from the first temperature to urge the tension member to shorten to apply compression between the proximal member and the distal member.

In the method of any preceding paragraph, the tension member may further have a shaft extending from a proximal end to a distal end of the tension member. The shaft may have a cannula. Inserting the bone screw into the bone may include inserting the bone screw over a guidewire placed in the bone such that the cannula receives the guidewire.

In the method of any preceding paragraph, the tension member may be at least partially formed of a superelastic material having an upper plateau stress at the first temperature and a lower plateau stress at the second temperature. The second temperature may be higher than the first temperature, and the upper plateau stress is similar in value to the lower plateau stress.

In the method of any preceding paragraph, the second temperature may be an internal body temperature of a patient, and moving the tension member to the second temperature may include allowing the tension member to move to the internal body temperature.

According to one embodiment, bone screw, insertable into a bone, may have a distal member with bone-engaging threads, a proximal member configured to slidably engage the distal member, and a tension member with a proximal end coupled to the proximal member, and a distal end coupled to the distal member such that, in response to motion of the distal member away from the proximal member, the tension member elongates and urges the distal member to move toward the proximal member. One of the proximal member and the distal member may have a torque transmission socket, the other of the proximal member and the distal member may have a shaft adjacent to a torque transmission protrusion that is slidably receivable within the torque transmission socket to transmit torque between the proximal member and the distal member, and the torque transmission protrusion may have a torque transmission feature with a first maximum diameter larger than a second maximum diameter of a portion of the shaft that is adjacent to the torque transmission feature.

In the bone screw of any preceding paragraph, the tension member may further have a shaft extending from the proximal end to the distal end. The shaft may have a cannula sized to receive a guidewire.

In the bone screw of any preceding paragraph, the proximal member may have a head and a shank that houses the torque transmission socket, and the head may have head threading with a first pitch different from a second pitch of the bone-engaging threads.

In the bone screw of any preceding paragraph, the proximal member and the distal member may define a longitudinal axis, and the proximal member may have a head and a shank that houses the torque transmission socket. The head may have a proximal-most surface that is nonperpendicular to the longitudinal axis.

In the bone screw of any preceding paragraph, the torque transmission socket may have a female spline, and the torque transmission feature of the torque transmission protrusion may have a male spline configured to mate with the female spline.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length.

In the bone screw of any preceding paragraph, the proximal member and the distal member define a longitudinal axis, the proximal member may have the torque transmission socket, the distal member may have the torque transmission protrusion, the distal member may have a distal engagement surface, distinct from the torque transmission protrusion, facing away from the longitudinal axis, the proximal member may have a proximal engagement surface, distinct from the torque transmission socket, facing toward the longitudinal axis, and the distal engagement surface may be positioned to abut the proximal engagement surface to transmit bending loads from the distal member to the proximal member.

According to one embodiment, a bone screw, insertable into a bone, may have a distal member with bone-engaging threads, a proximal member configured to slidably engage the distal member, and a tension member with a proximal end coupled to the proximal member, and a distal end coupled to the distal member such that, in response to motion of the distal member away from the proximal member, the tension member elongates and urges the distal member to move toward the proximal member. The bone screw may have a length from a proximal-most end of the proximal member to a distal-most end of the distal member, and the proximal member and the distal member cooperate to define a length limiting mechanism configured to prevent the length from exceeding a maximum length, and prevent the length from decreasing below a minimum length.

In the bone screw of any preceding paragraph, the tension member may further have a shaft extending from the proximal end to the distal end. The shaft may have a cannula sized to receive a guidewire.

In the bone screw of any preceding paragraph, the proximal member may have a shank and a head with head threading with a first pitch different from a second pitch of the bone-engaging threads.

In the bone screw of any preceding paragraph, the proximal member and the distal member may define a longitudinal axis, and the proximal member may have a shank and a head with a proximal-most surface that is nonperpendicular to the longitudinal axis.

In the bone screw of any preceding paragraph, the length limiting mechanism may have a distal shoulder and a proximal shoulder, both of which are on one of the proximal member and the distal member, and a stop feature on the other of the proximal member and the distal member. The stop feature may be positioned between the distal shoulder and the proximal shoulder to define the minimum length and the maximum length by abutting the stop feature against the distal shoulder and the proximal shoulder.

In the bone screw of any preceding paragraph, the distal shoulder and the proximal shoulder may be on the distal member, the stop feature may be on the proximal member, the stop feature may abut the distal shoulder to define the minimum length, and the stop feature may abut the proximal shoulder to define the maximum length.

In the bone screw of any preceding paragraph, the proximal member and the distal member may define a longitudinal axis. The proximal member may have a proximal torque transmission feature, the distal member may have a distal torque transmission feature that engages the proximal torque transmission feature to receive torque from the proximal member, the distal member may have a distal engagement surface, distinct from the distal torque transmission feature, facing away from the longitudinal axis, the proximal member may have a proximal engagement surface, distinct from the proximal torque transmission feature, facing toward the longitudinal axis, and the distal engagement surface may be positioned to abut the proximal engagement surface to transmit bending loads from the distal member to the proximal member.

According to one embodiment, a bone screw, insertable into a bone, may have a distal member with bone-engaging threads, a proximal member configured to slidably engage the distal member, and a tension member with a proximal end coupled to the proximal member, a distal end coupled to the distal member such that, in response to motion of the distal member away from the proximal member, the tension member elongates and urges the distal member to move toward the proximal member, and a shaft extending from the proximal end to the distal end. The shaft may have a cannula sized to receive a guidewire. The proximal member and the distal member may define a longitudinal axis, the distal member may have a distal engagement surface facing away from the longitudinal axis, the proximal member may have a proximal engagement surface facing toward the longitudinal axis, and the distal engagement surface may be positioned to abut the proximal engagement surface to transmit bending loads from the distal member to the proximal member without transmitting torque between the proximal member and the distal member.

In the bone screw of any preceding paragraph, the proximal member may have a shank and a head with head threading with a first pitch different from a second pitch of the bone-engaging threads.

In the bone screw of any preceding paragraph, the proximal member and the distal member define a longitudinal axis, and the proximal member may have a shank and a head with a proximal-most surface that is nonperpendicular to the longitudinal axis.

In the bone screw of any preceding paragraph, the proximal member may have a proximal torque transmission feature distinct from the proximal engagement surface, and the distal member may have a distal torque transmission feature, distinct from the distal engagement surface, configured to receive torque from the proximal torque transmission feature.

In the bone screw of any preceding paragraph, the proximal torque transmission feature may be in a torque transmission socket, the distal torque transmission feature may be on torque transmission protrusion that is slidably receivable within the torque transmission socket to transmit torque between the proximal member and the distal member, the proximal torque transmission feature may have a female spline, and the distal torque transmission feature may have a male spline configured to mate with the female spline.

In the bone screw of any preceding paragraph, the bone screw may have a length from a proximal-most end of the proximal member to a distal-most end of the distal member, and the proximal member and the distal member may cooperate to define a length limiting mechanism configured to prevent the length from exceeding a maximum length, and prevent the length from decreasing below a minimum length. The length limiting mechanism may have a distal shoulder and a proximal shoulder, both of which are on one of the proximal member and the distal member, and a stop feature on the other of the proximal member and the distal member. The stop feature may be positioned between the distal shoulder and the proximal shoulder to define the minimum length and the maximum length by abutting the stop feature against the distal shoulder and the proximal shoulder.

In the bone screw of any preceding paragraph, the distal shoulder and the proximal shoulder may be on the distal member, the stop feature may be on the proximal member, the stop feature may abut the distal shoulder to define the minimum length, and the stop feature may abuts the proximal shoulder to define the maximum length.

These and other features and advantages of the present disclosure will become more fully apparent from the following description and appended claims or may be learned by the practice of the devices, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIGS. 1A, 1B, 1C, and 1D are perspective, side elevation, front elevation, and rear elevation views, respectively, of a bone screw according to one embodiment.

FIGS. 3A, 3B, 3C, and 3D are side elevation, section views of the bone screw, the proximal member, the distal member, and the tension member, respectively, of FIG. 1.

Figure 2:
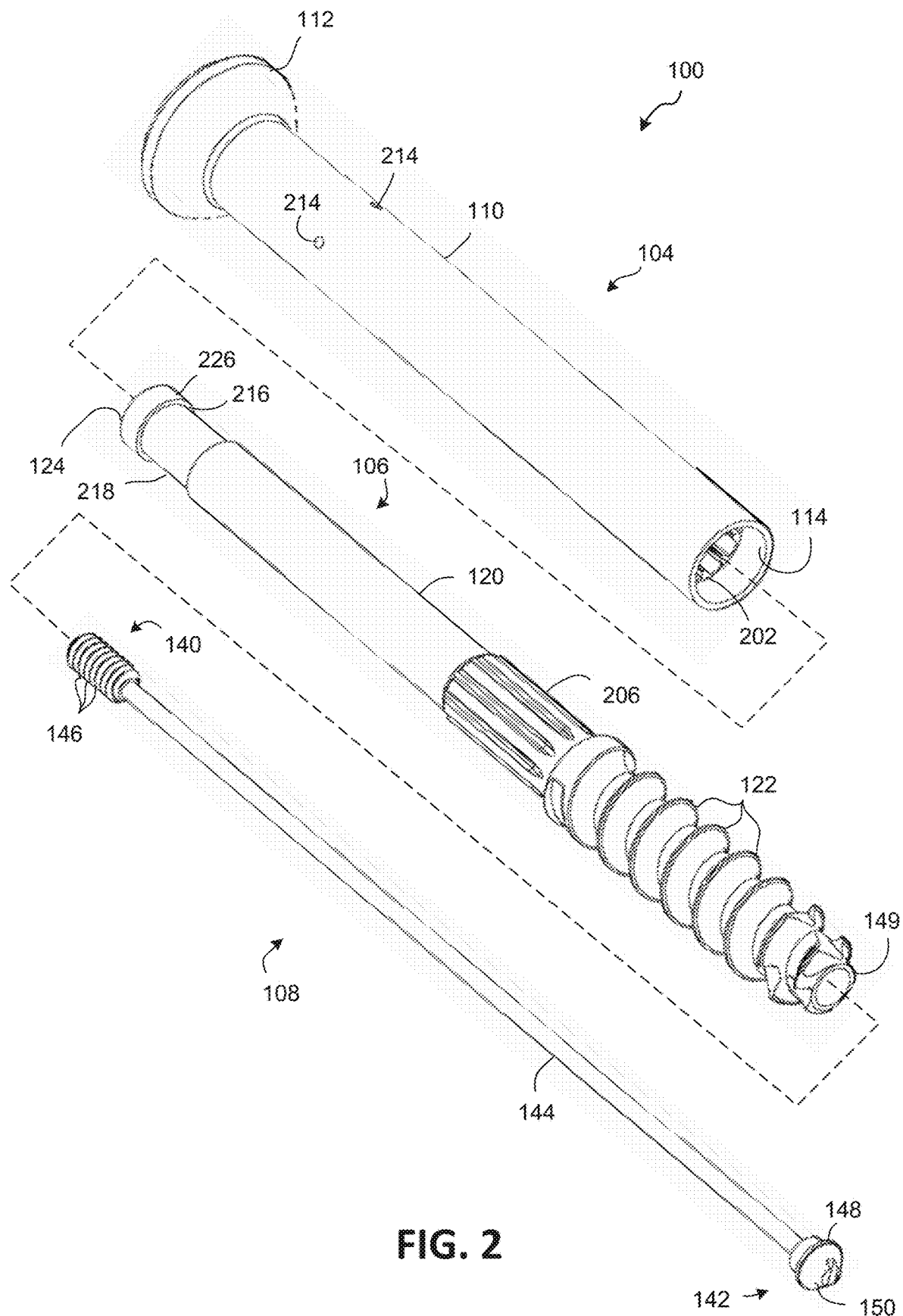
FIG. 2 is an exploded, perspective view of the bone screw of FIG. 1.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary." is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following examples have been included to provide guidance to one of ordinary skill in the art for practicing representative embodiments of the presently disclosed subject matter. In light of the present disclosure and the general level of skill in the art, those of skill in the art can appreciate that the following examples are intended to be exemplary only and that numerous changes, modifications, and alterations can be employed without departing from the scope of the presently disclosed subject matter.

Fixation of bone portions with bone screws may be utilized in a variety of surgical procedures including, but not limited to trauma fixation, arthrodesis, osteotomies, etc. For example, trauma fixation procedures may be needed when high-energy events cause bones to break and fragment. Bone screws may be utilized to secure the bone fragments in a correct anatomic alignment while the bone heals. Arthrodesis procedures can treat degenerative bone joints, which may cause pain and loss of joint function, by removing degraded articular cartilage from a bone joint and then holding the bone joint in compression with bone screws while the bones fuse together across the joint. Osteotomy procedures can realign a bone to a more favorable position, by first cutting the bone and then using bone screws to hold the cut bone portions in a new desired alignment while the bone heals.

Example applications/procedures that may utilize any of the fixation devices described or contemplated herein, in any configuration and with any of the features described herein, may include, but are not limited to: trauma procedures (e.g., fracture fixation, etc.), post-traumatic reconstruction (pelvic or joint fusions), spine procedures (e.g., SI fusion, facet fixation, etc.), joint reconstruction procedures (total hip arthroplasty, total knee arthroplasty), sports related procedures, extremity procedures, cranio-maxillo-facial procedures, rib plating procedures, veterinary procedures, bone plating procedures (e.g., femur plates, humerus plates, tibial plates, etc.), intramedullary nail fixation procedures, amputee connection procedures, sarcoma procedures, shoulder/glenoid fixation, small bone fixation, correction, or fusion (e.g., foot/ankle, hand/wrist, etc.), joint fusions, osteotomies, procedures involving osteoporotic or compromised bone, etc.

The following disclosure presents various bone fixation devices, systems, and methods for utilization in bone and other tissues as implantable devices (e.g., orthopedic implants, spine implants, sports medicine implants, trauma implants, reconstruction implants, extremity implants, veterinary implants, etc.). It will be understood that any feature of any bone fixation assembly described or contemplated herein may be combined with any other bone fixation assembly that is described or contemplated herein without departing from the spirit or scope of the present disclosure.

Figure 4:
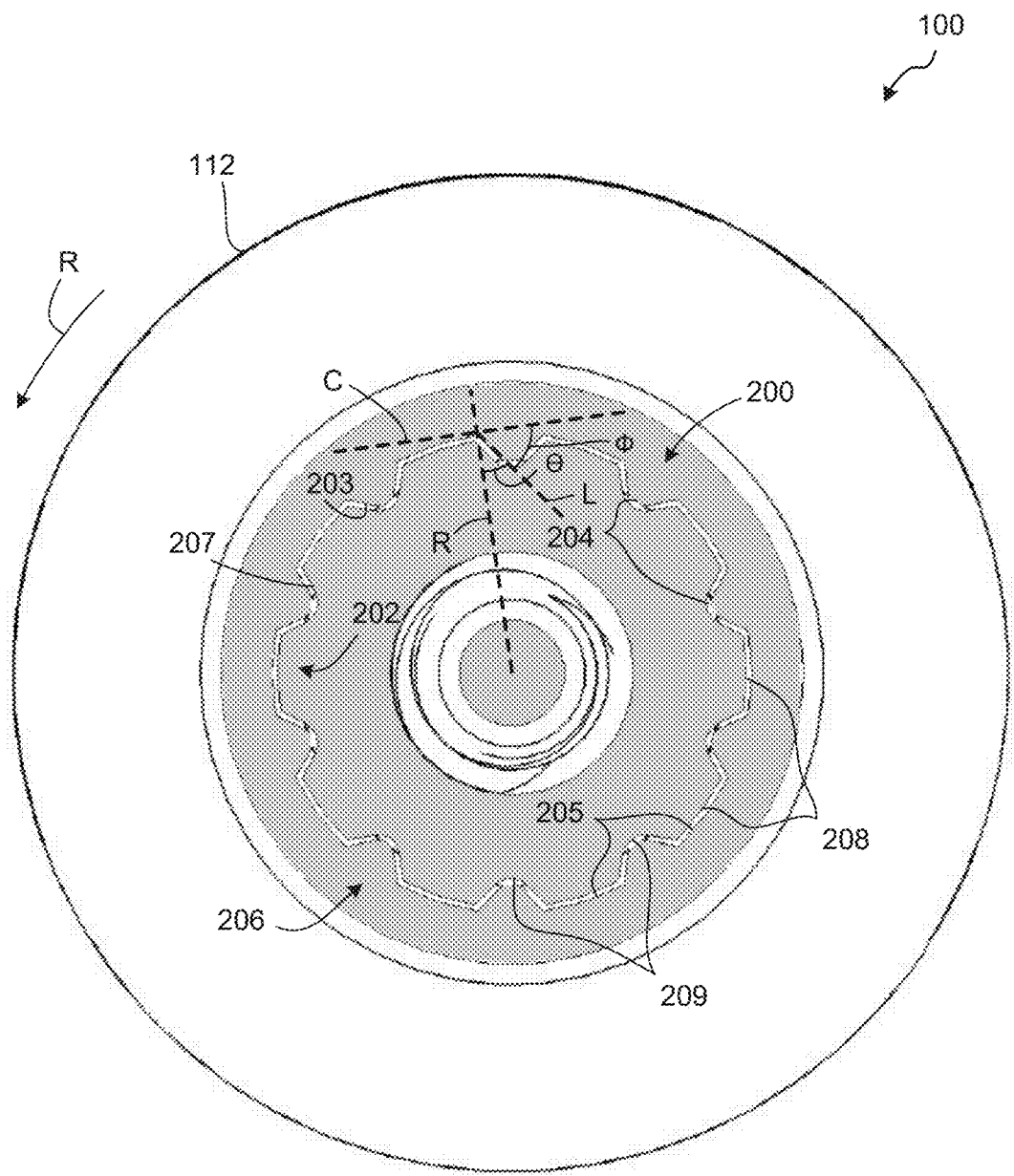
FIG. 4 is a front elevation, section view of the bone screw of FIG. 1.
Figure 5:
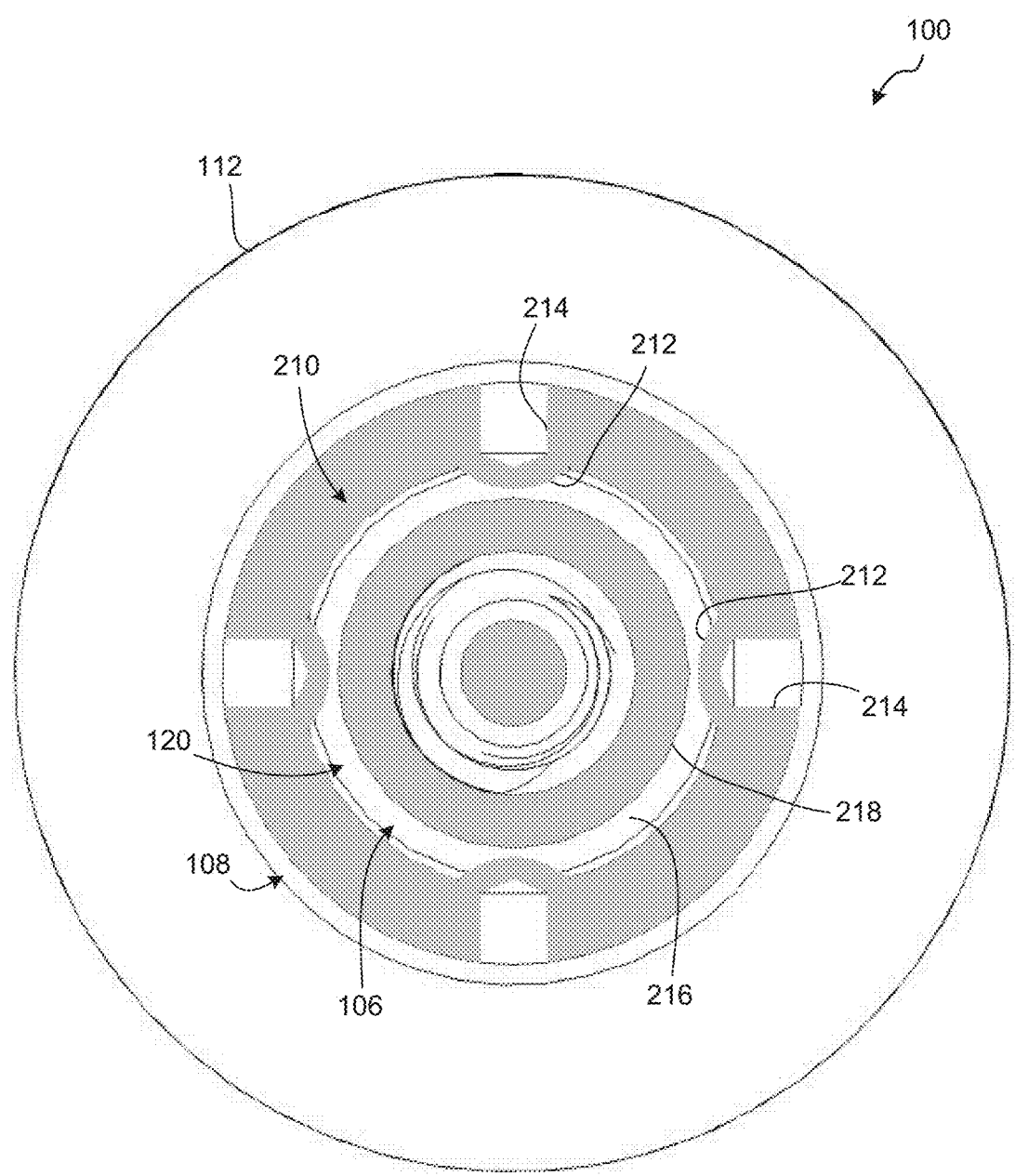
FIG. 5 is another front elevation, section view of the bone screw of FIG. 1.

According to some embodiments, a bone screw 100 may be provided. The bone screw may have a longitudinal axis 102, a proximal member 104, a distal member 106, and a tension member 108. The bone screw 100 will be shown and described in connection with FIGS. 1A through 5. FIGS. 1A, 1B, 1C, and 1D are perspective, side elevation, front elevation, and rear elevation views, respectively, of the bone screw 100. FIG. 2 is an exploded, perspective view of the bone screw 100. FIGS. 3A, 3B, 3C, and 3D are side elevation, section views of the bone screw 100, the proximal member 104, the distal member 106, and the tension member 108, respectively. FIG. 4 is a front elevation, section view of the bone screw 100. FIG. 5 is another front elevation, section view of the bone screw 100.

As shown, the longitudinal axis 102 of the bone screw 100 may be an axis extending along the geometric center and/or axis of radial symmetry of the bone screw 100, along the longest length of the bone screw 100. The terms "proximal" and "distal" are generally used with reference to displacement along the longitudinal axis 102, although they are sometimes used as adjectives to connect features to a proximal or distal member, such as the proximal member 104 and the distal member 106.

The proximal member 104 may have a proximal shank 110 at a distal end of the proximal member 104, a head 112 at a proximal end of the proximal member 104, and a proximal interior surface 114 that cooperates with an interior surface 115 of the proximal member 104 to define a proximal portion 132 of a variable-length cavity 130. The head 112 may have a width 126 (i.e., greatest dimension perpendicular to the longitudinal axis 102) greater than a width 128 of the proximal shank 110. Thus, upon insertion into the bone, the head 112 may protrude transverse to the longitudinal axis 102 to engage the cortex of the bone into which the bone screw 100 is driven, as will be shown subsequently. The proximal interior surface 114 and the interior surface 115 may face inwardly, toward the longitudinal axis 102. The head 112 may have a driver engagement feature 230 that receives torque from a driver (not shown). For example, the driver engagement feature 230 may be a socket with a radially symmetrical pattern that receives a boss, with a matching shape, on the distal end of the driver. The driver engagement feature 230 may be a hexagonal socket as shown.

The distal member 106 may have a distal shank 120 at a proximal end of the distal member 106, bone-engaging threads 122 at a distal end of the distal member 106, and a distal interior surface 124 defining a distal portion 134 of the variable-length cavity 130. The bone-engaging threads 122 may be designed to engage bone, and may be shaped to function optimally upon insertion into a pilot hole previously formed in the bone. In the alternative, the bone-engaging threads 122 may be self-tapping, and may enable the bone screw 100 to form its own pilot hole in the bone into which it is inserted.

The tension member 108 may have a proximal end 140, a distal end 142, and a shank 144, extending along the longitudinal axis 102, that connects the proximal end 140 to the distal end 142. The proximal end 140 may have proximal threads 146 that facilitate coupling of the tension member 108 to the proximal member 104 via threaded engagement with interior threads 147 within the proximal member 104. The distal end 142 may have a distal flange 148 that facilitates coupling of the tension member 108 to the distal member 106 via abutment of the distal flange 148 on a corresponding surface 149 of the distal member 106, distal to the bone-engaging threads 122. The distal end 142 may further have a distal tip 150 that is sufficiently sharp for bone penetration. The distal tip 150 may have one or more features, such as channels or grooves, that help remove bone cuttings from in front of the distal tip 150. Additionally or alternatively, the distal tip 150 may have a slot 152 that facilitates rotation of the tension member 108 with a driver such as a flat-head screwdriver.

As shown more clearly in FIGS. 2 and 3A, the bone screw 100 may be assembled by, first, inserting the proximal end 140 of the tension member 108 along the proximal direction, through the open distal end of the distal member 106, until the distal flange 148 of the distal end 142 of the tension member 108 rests against the corresponding surface 149 of the distal member 106. Then, the distal shank 120 of the distal member 106 and the proximal end 140 of the tension member 108 may be inserted into the proximal portion 132 of the variable-length cavity 130, within the proximal member 104. The tension member 108 may be rotated relative to the proximal member 104 and the distal member 106 (for example, by rotating the distal tip 150 of the tension member 108 with a flat-head screwdriver or other driver) such that the proximal threads 146 of the proximal end 140 of the tension member 108 engage the interior threads 147 of the proximal member 104.

This may result in the configuration shown in FIG. 3A, in which the tension member 108 resides generally within the variable-length cavity 130, which is defined by the proximal member 104 and the distal member 106. The variable-length cavity 130 may include a proximal portion 132 within the proximal member 104, and a distal portion 134 within the distal member 106. Part of the distal portion 134 may also reside within the proximal member 104, as the distal shank 120 is within the proximal portion 132 of the variable-length cavity 130.

The bone screw 100 may be used for a variety of purposes, including but not limited to fracture fixation, joint arthrodesis, and implant fixation. In some implementations, the bone screw 100 may be inserted through one bone portion or implant, and into a separate bone portion in which the bone-engaging threads 122 are anchored. As mentioned previously, in some embodiments, the bone screw 100 may be inserted into a pilot hole previously formed in the bone. In alternative embodiments, the bone screw 100 may be driven against the bone to form and tap its own hole.

In either case, the bone screw 100 may be rotated (for example, via a driver) such that the bone-engaging threads 122 draw the bone screw 100 to advance until the head 112 rests against the exterior surface of the proximal bone portion or implant. Then, the bone screw 100 may be further advanced such that the distal member 106 is urged distally, by virtue of the action of the bone-engaging threads 122, relative to the proximal member 104. The tension member 108 may be dimensioned such that the shank 144 of the tension member 108 elongates in response to this force, permitting the distal member 106 to move distally while the proximal member 104 remains generally in place.

The tension on the shank 144 may cause the tension member 108 to exert compressive force, drawing the distal member 106 back proximally relative to the proximal member 104. This compressive force may act across the junction between the bone portions (or in the case of implant fixation, between the bone and the implant), and may beneficially facilitate osteointegration, fracture healing, lasting fracture fixation, and/or the like.

This further advancement of the distal member 106 may continue until the bone screw 100 has reached its desired length. The length may be selected such that the tension member 108 continues to exert compressive force, even after some of the strain in the tension member 108 has relaxed, for example due to bone subsidence, patient motion, and/or other factors.

In some embodiments, the proximal member 104 and the distal member 106 may be formed of relatively high-strength biocompatible materials such as titanium and/or titanium alloys. The tension member 108 may advantageously be formed of a biocompatible superelastic material such as Nitinol. The superelastic material may beneficially undergo considerable strain while exerting a generally constant compressive force on the proximal member 104 and the distal member 106. Thus, the tension member 108 may maintain compression even after some relaxation in strain has occurred.

The bone screw 100 will likely be under considerable stress as it is driven into the bone and/or as the patient goes about his or her activities with the bone screw 100 in place. In a larger screw (such as most wood screws), these stresses may not be of concern. However, the bone screw 100 may desirably be relatively small in diameter—for example, from 3.5 mm to 7.0 mm, measured at the diameter of the proximal shank 110 of the proximal member 104. The bone screw 100 may thus have a number of features that help distribute, shift, and/or otherwise manage stresses in the proximal member 104, the distal member 106, and/or the tension member 108 to avoid failure (for example, breakage or plastic deformation) of the proximal member 104, the distal member 106, and/or the tension member 108. Notably, hollow screws of this size that lack such stress distribution features may be likely to fail during insertion and/or during healing.

More specifically, the bone screw 100 may have a torque transmission feature, a length limiting mechanism, a bending transmission feature, and deliberately selected exterior diameter. Each of these features may help to control some aspect of the stresses experienced by the proximal member 104, the distal member 106, and/or the tension member 108, as will be described below.

The bone screw 100 may have a torque transmission feature that transmits torque from the proximal member 104 to the distal member 106. The torque transmission feature may be configured to control stresses in the proximal member 104 and the distal member 106 incident to application of torque as the bone screw 100 is driven into the bone. It has been observed that torque transmission features with torque transmission surfaces oriented circumferentially, or nearly circumferentially, can be subject to high hoop stresses as these surfaces, as can the surfaces to which they transmit torque. Conventional polyhedral interfaces (such as a hexagonal hole and driver) are thus subject to high stresses during torque transmission. Similarly, an interface in which one or more flats on a cylindrical member are placed within a hole having one or more matching flats, would also be subject to high stress.

Accordingly, the torque transmission feature employed by the bone screw 100 may have a design in which the torque transmission surface(s) are angled significantly from the circumferential direction. This angle may be greater than 20°, greater than 30°, greater than 40°, greater than 50°, greater than 60°, greater than 70°, or even greater than 80°. In some embodiments, the angle may be 90°. Further, in other embodiments, this angle may be even greater than 90°. Although large angles may be beneficial for hoop stress reduction, in some embodiments, sufficient hoop stress reduction may be obtained with torque transmission surfaces that are angled such that they are oriented closer to the radial direction than the circumferential direction.

As embodied in FIGS. 1A through 5, and shown most clearly in FIG. 4, the torque transmission feature of the bone screw 100 may be a spline 200. The spline 200 may include an outer spline component 202 formed on the proximal interior surface 114 of the proximal member 104, and an inner spline component 206 formed on the distal shank 120 of the distal member 106. The outer spline component 202 may mesh with the inner spline component 206 such that the outer spline component 202 transmits torque to the inner spline component 206. Thus, as the proximal member 104 is rotated by the surgeon (for example, via a driver engaging the head 112), the distal member 106 may also rotate, driving the bone-engaging threads 122 into the bone.

As further shown in FIG. 4, the outer spline component 202 may have torque transmitting surfaces 203 that are on the leading sides of outer teeth 204 as the proximal member 104 rotates about the longitudinal axis 102, along the direction of rotation R. The outer teeth 204 may extend along part of the length of the proximal portion 132 of the variable-length cavity 130, parallel to the longitudinal axis 102. The outer teeth 204 may be separated from each other by outer grooves 205 that also extend parallel to the longitudinal axis 102.

The outer spline component 202 is shown with ten of the outer teeth 204; however, those of skill in the art will recognize that any number of teeth may be present. In some embodiments, only a single tooth may be present. The presence of multiple teeth may help to spread the loads induced by torque transmission across additional surfaces, and to multiple sectorial portions of the proximal member 104 and the distal member 106.

The inner spline component 206 may have torque receiving surfaces 207 that are on the trailing surfaces of inner teeth 209 as the distal member 106 rotates about the longitudinal axis 102, along the direction of rotation R. The inner teeth 209 may extend along part of the length of the distal portion 134 of the variable-length cavity 130, parallel to the longitudinal axis 102. The inner teeth 209 may be separated from each other by inner grooves 208 that also extend parallel to the longitudinal axis 102.

The number of inner grooves 208 on the inner spline component 206 may be equal to the number of outer teeth 204 on the outer spline component 202. In FIG. 4, there are ten of the outer teeth 204 that reside within ten of the inner grooves 208. Similarly, there are ten of the inner teeth 209 that reside within ten of the outer grooves 205. Thus, the outer spline component 202 meshes with the inner spline component 206. As indicated previously, more or fewer teeth or grooves may be present in either component. The number of teeth in one component may be equal to the number of grooves in the other, but this is not necessarily the case—in some embodiments, unequal numbers of teeth and/or grooves may be present between inner and outer spline components.

The torque transmitting surfaces 203 of the outer spline component 202 may advantageously be angularly displaced from the circumferential direction C by an angle $\Phi$, shown in FIG. 4. The line L represents one of the torque transmitting surfaces 203 of the outer spline component 202. As set forth above, the angle $\Phi$ may be significant so as to reduce hoop stresses in the proximal member 104 and/or the distal member 106. In some embodiments, the angle $\Phi$ may be greater than an angle $\theta$ between the line L and the radial direction R. Thus, the angle $\Phi$ may be greater than 45°.

The spline 200 represents only one of multiple different types of torque transmission features that may be used within the scope of the present disclosure. Various other torque transmission features, including but not limited to polyhedral and curvilinear shapes, may be used. A polyhedral torque transmission feature may include star shapes, rectangles, and/or other shapes with torque transmission surfaces that are angularly displaced from the circumferential direction. Curvilinear torque transmission features may likewise have such angled torque transmission surfaces, and may include curvilinear and/or rectilinear segments. In some embodiments, a more organically-shaped rounded spline may be used. In other embodiments, an ovoid, elliptical, or other curvilinear torque transmission feature may be present.

The bone screw 100 may also have a length limiting mechanism 210 that helps to control the elongation of the bone screw 100. Unlimited elongation of the bone screw 100 may cause the tension member 108 to fail in tension, as the loads experienced by the tension member 108 (static and/or fatigue loading) may cause the tension member 108 to break or plastically deform. In some embodiments, the length limiting mechanism 210 may operate to limit the displacement of the distal member 106 relative to the proximal member 104 such that the stress on the tension member 108 remains within its superelastic zone, as will be shown and described hereafter. Further, in some embodiments, the bone screw 100 may be designed for infinite life. Thus, the length limiting mechanism 210 may be designed to limit displacement of the distal member 106 relative to the proximal member 104 such that the strength limits of the tension member 108 are not exceeded.

As shown, the length limiting mechanism 210 may include a proximal stop feature on the proximal member 104 and a distal stop feature on the distal member 106. The proximal stop feature and the distal stop feature may come into contact with each other when the maximum length of the bone screw 100 is reached, preventing further distal motion of the distal member 106 relative to the proximal member 104. The proximal stop feature and the distal stop feature may each take many forms. One or more than one of each of the proximal stop feature and the distal stop feature may be present in a bone screw according to the present disclosure.

As shown in FIGS. 3A, 3B, and 5, the proximal member 104 may have multiple proximal stop features, each of which is a protrusion 212 on the proximal interior surface 114. Each protrusion 212 may protrude inwardly (i.e., toward the longitudinal axis 102 and the distal member 106, nested within the proximal portion 132 of the variable-length cavity 130) from the remainder of the proximal interior surface 114. Each protrusion 212 may be formed, for example, through the use of apertures 214 formed in the exterior surface of the proximal member 104. In some embodiments, the apertures 214 may be formed as blind holes that are separated from the proximal portion 132 of the variable-length cavity 130 by relatively thin walls. After the distal shank 120 of the distal member 106 has been inserted into the proximal portion 132 of the variable-length cavity 130, pins or other projecting members may be inserted into the apertures 214 and pressed inwardly to flex the thin walls inward, thus forming each protrusion 212.

The distal member 106 may have a single distal stop feature that contacts all of the protrusions 212. As shown in FIGS. 3A, 3C, and 5, the distal stop feature of the distal member 106 may be a shoulder 216 that defines one end of a relief 218 formed on the distal shank 120 of the distal member 106. Specifically, the relief 218 may be formed as a smaller-diameter section of the distal shank 120, on an extension of the distal shank 120 that extends proximally from the inner spline component 206. The relief 218 may be proximate a proximal end of the distal shank 120 and may define the shoulder 216.

After full insertion of the distal shank 120 into the proximal portion 132 of the variable-length cavity 130, the relief 218 may be aligned with the apertures 214 of the proximal member 104. Thus, when the protrusions 212 are formed as described above, the protrusions 212 may extend inwardly into the relief 218. The protrusions 212 may protrude sufficiently into the relief 218 such that the shoulder 216 is unable to move distally beyond the protrusions 212. Thus, abutment of the shoulder 216 against the protrusions 212 may limit the extent to which the distal member 106 is able to move distally relative to the proximal member 104.

When the distal shank 120 is fully inserted into the proximal portion 132 of the variable-length cavity 130 (such that the distal shank 120, in its entirety, is received within the proximal portion 132), the protrusions 212 may reside near the distal end of the relief 218. Thus, the length of the relief 218 may define the extent to which the distal member 106 is able to move distally relative to the proximal member 104.

Advantageously, the length limiting mechanism 210 may be displaced proximally of the spline 200. Thus, the length limiting mechanism 210 may operate without interfering with operation of the spline 200, and without requiring added complexity in the torque transmission feature of the bone screw 100.

A "length limiting mechanism" may include any of a wide variety of devices that can limit the elongation of a bone screw. Similarly, a "proximal motion stop" and a "distal motion stop" may each include any feature that can be physically interfere with such elongation. Thus, proximal and distal motion stops may include any known combination of protruding elements, including but not limited to flanges, bumps, tabs, detents, shoulders, and the like. Such elements may protrude inwardly, outwardly, and/or in a circumferential direction.

The bone screw 100 may also have a bending transmission feature 220 that helps to transfer bending loads between the proximal member 104 and the distal member 106 at a location displaced from where such loading is applied. For example, if the bone screw 100 is inserted through a first bone portion such that the bone-engaging threads 122 anchor in a second bone portion, motion (or attempted motion) of the user may urge the second bone portion to move relative to the first bone portion. This force may be in shear (i.e., urging relative motion parallel to the interface or fracture between the first and second bone portions), tension (urging relative motion perpendicular to the interface or fracture), bending (urging relative motion along an axis offset from the longitudinal axis 102 of the bone screw 100), and/or torsion (urging rotation of the second bone portion relative to the first bone portion about the longitudinal axis 102 of the bone screw 100).

These forces may result in a bending moment on the bone screw 100 and may be greatest at the interface between the first and second bone portions. The bending transmission feature 220 may advantageously be displaced proximally or distally from this interface and may thus distribute some of these forces away from the interface. Further, the bending transmission feature 220 may transfer some bending load from the distal member 106 to the proximal member 104. The distal member 106 may have the smaller cross-sectional shape proximate the interface between the first and second bone portions and may thus be subject to higher bending stress. Accordingly, shifting some of this bending stress to the proximal member 104 may increase the overall bending load that can be tolerated by the bone screw 100.

As shown in FIGS. 3A, 3B, and 3C, the bending transmission feature 220 may include a proximal engagement surface 222 on the proximal member 104 and a distal engagement surface 226 on the distal member 106. In the embodiment of FIGS. 3A, 3B, and 3C, the distal engagement surface 226 may be an outwardly-facing surface proximal to the shoulder 216, at the proximal end of the distal shank 120. The proximal engagement surface 222 may be located on a proximal portion of the interior surface 115, which faces inwardly, and faces the distal engagement surface 226.

The distal engagement surface 226 may be sized such that it has a diameter near that of the proximal engagement surface 222. Advantageously, the distal engagement surface 226 may be slightly smaller than the proximal engagement surface 222 such that the distal engagement surface 226 can be received within the proximal engagement surface 222 with clearance during assembly of the proximal member 104 and the distal member 106. This clearance may be relatively small so that, in response to slight bending of the bone screw 100, the distal engagement surface 226 abuts the proximal engagement surface 222 to transmit some of the bending load from the distal member 106 to the proximal member 104.

For example, a bending load on the bone screw 100 may urge the distal member 106 to shift such that its axis is no longer colinear with the axis of the proximal member 104. This motion of the distal member 106 may cause the distal shank 120 of the distal member 106 to move toward one side of the interior surface 115. Abutment of the distal engagement surface 226 with the proximal engagement surface 222 may limit this bending such that the material near the maximum bending stress (for example, near the interface between bone portions) is not stressed at a level that would cause it to plastically deform or break.

The bending transmission feature 220 is only one of many possible structures that may be used to transmit bending loads away from the site of maximum stress. Notably, the bone screw 100 may include other features that may also act as bending transmission features, in addition to or in the alternative to the proximal engagement surface 222 and the distal engagement surface 226. Any surfaces of the proximal member 104 and the distal member 106 that abut each other in response to application of bending load on the bone screw 100 may be considered bending transmission features. In particular, the entire length of the distal shank 120 (with the exception of the relief 218) proximal to the inner spline component 206, and the corresponding inwardly-facing regions of the interior surface 115 of the proximal member 104, may also act as bending transmission features, as they may abut each other and transmit bending loads from the distal member 106 to the proximal member 104 as the bone screw 100 is loaded in bending.

Further, the phrase "bending transmission feature" includes any combination of surfaces, however shaped, that abut each other to transmit such loading. By way of example and not limitation, such surfaces may have cylindrical, splined, polygonal, irregular, and/or other cross-sectional shapes. Such surfaces may be parallel to the longitudinal axis 102, or in alternative embodiments, may be angled nonparallel to the longitudinal axis 102. Thus, bending transmission features need not be linear extrusions, but may instead have conical, semispherical, or other shapes with variation toward and/or away from the longitudinal axis 102.

The bone screw 100 may further have other features and/or dimensions that help provide the bone screw 100 with enhanced strength and/or rigidity over prior art variable-length screws. For example, many known screws have a shank that is only as large as the minor diameter of the screw threads. Such a design has the benefit of simple preparation, as the corresponding pilot hole may be formed with a drill bit (not shown) with a constant diameter. By contrast, the bone-engaging threads 122 of the bone screw 100 may be dimensioned such that portions of the bone screw 100 proximal to the bone-engaging threads 122 (excluding the head 112) are larger than the minor diameter of the bone-engaging threads 122.

Specifically, as shown in FIG. 3C, the bone-engaging threads 122 may have a minor diameter 242, a major diameter 244, and a pitch 246. The distal shank 120 may have an exterior diameter 248, adjacent to the bone-engaging threads 122, that is larger than the minor diameter 242 of the bone-engaging threads 122. This may provide the distal shank 120, and in particular, the portion of the distal shank 120 adjacent to the bone-engaging threads 122, with added bending strength over that which would be present in bone screws with shanks that are limited in size to the minor diameter of the screw threads.

The distal shank 120 may also have an exterior diameter 250, displaced proximally of the bone-engaging threads 122, and also proximal to the inner spline component 206. The exterior diameter 250 may also be larger than the minor diameter 242 of the bone-engaging threads 122. In some embodiments, the exterior diameter 248 and/or the exterior diameter 250 may be equal to and/or larger than the major diameter 244. In yet other embodiments, the exterior diameter 248 and/or the exterior diameter 250 may be the equal in size, larger, or smaller than the average of the minor diameter 242 and the major diameter 244 of the bone-engaging threads 122.

As a result of these deliberate dimensioning decisions, the weakest cross-section of the bone screw 100, as to bending, may be displaced from the location of maximum bending stress. More precisely, maximum bending stress may be experienced at the interface between the items being secured together by the bone screw 100 (for example, between two bone fragments or portions to be secured together). A screw (not shown) with distal threading with a minor diameter equal to the outer diameter of the shank of the screw may have a weakest cross section, as to bending, displaced significantly proximally of the screw threads. Thus, the location of maximum stress may unfortunately align with the part of the screw that is most susceptible to bending, which may be near the center of the screw.

Conversely, the bone screw 100 may have a weakest cross section, as to bending, that is distal to the center of the screw, and thus likely displaced distally of the location of maximum bending stress. For example, the weakest cross section of the bone screw 100, as to bending, may be immediately proximal to the bone-engaging threads 122. This location may be displaced distally from the interface between bone portions when the bone screw 100 is fully inserted because the bone-engaging threads 122 may advantageously be driven fully into the distal bone portion or fragment, and then driven further to cause elongation of the bone screw 100, as will be described hereafter.

Further, as shown in FIG. 3B, the proximal shank 110 may have an exterior diameter 252 that is also larger than the minor diameter 242 of the bone-engaging threads 122. Thus, not only the distal member 106, but also the proximal member 104, may have enhanced strength and/or rigidity. As further shown in FIG. 3A, the exterior diameter 252 may be as large as the major diameter 244 of the bone-engaging threads 122, providing the bone screw 100 with yet more additional strength and/or rigidity. In alternative embodiments, the exterior diameter 252 may be larger than the minor diameter 242 but smaller than the major diameter 244 of the bone-engaging threads 122.

The exterior diameter 252 may conform to standard or otherwise known sizes for orthopedic screws. This may facilitate use of the bone screw 100 in place of conventional screws for a wide variety of orthopedic applications. In some embodiments, the exterior diameter 252 may be within the range of 1 mm to 10 mm. Yet more specifically, the exterior diameter 252 may be within the range of 2 mm to 8 mm. Still more specifically, the exterior diameter 252 may be within the range of 3.5 mm to 7 mm. In some embodiments, the exterior diameter 252 may be within the range of 4 mm to 6 mm. Yet more specifically, the exterior diameter 252 may be about 5 mm. FIGS. 1A through 5 are shown to scale for the particular embodiment of the bone screw 100; hence, other dimensions of the bone screw 100 may be derived from these possible values of the exterior diameter 252.

The bone screw 100 may be applied to bone and/or implant structures in a wide variety of ways. In some embodiments, a pilot hole may first be formed in the bone in which the bone-engaging threads 122 are to be engaged. A stepped pilot drill bit (not shown) may advantageously be used for this purpose. The stepped pilot drill bit may have a distal portion with a smaller diameter and a proximal portion with a larger diameter. The distal portion may have a length and position that corresponds to the location of the bone-engaging threads 122 when the bone screw 100 has been fully inserted and/or when the bone-engaging threads 122 have reached their final position in the bone.

Figure 6A:
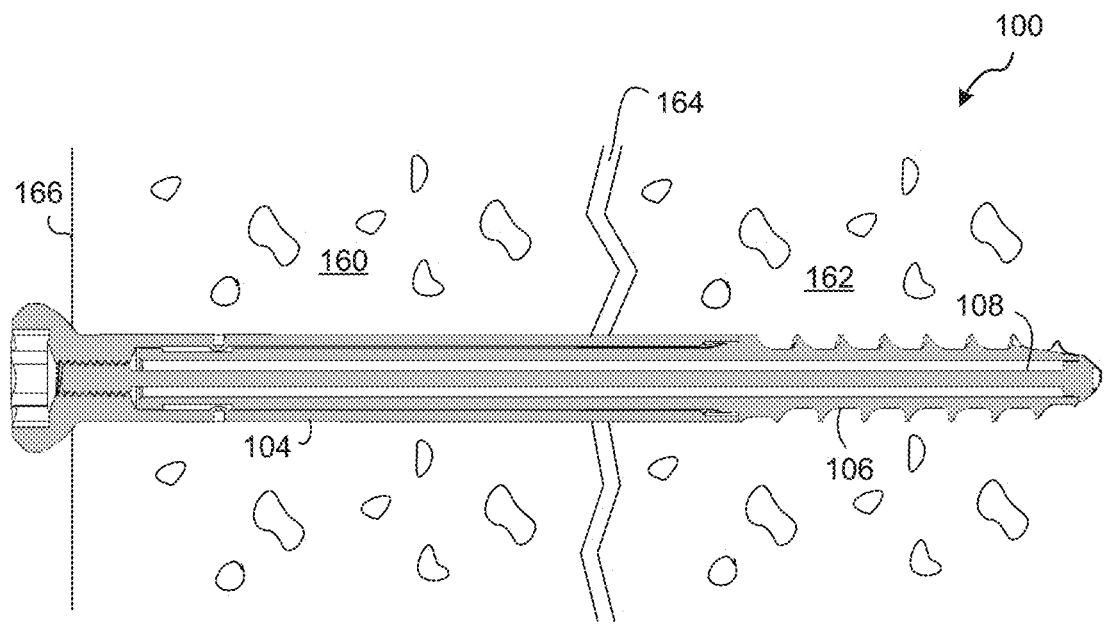
FIGS. 6A and 6B are side elevation, section views of the bone screw of FIG. 1, upon initial insertion into bone, and upon further insertion to tension the bone screw, respectively.
Figure 6B:
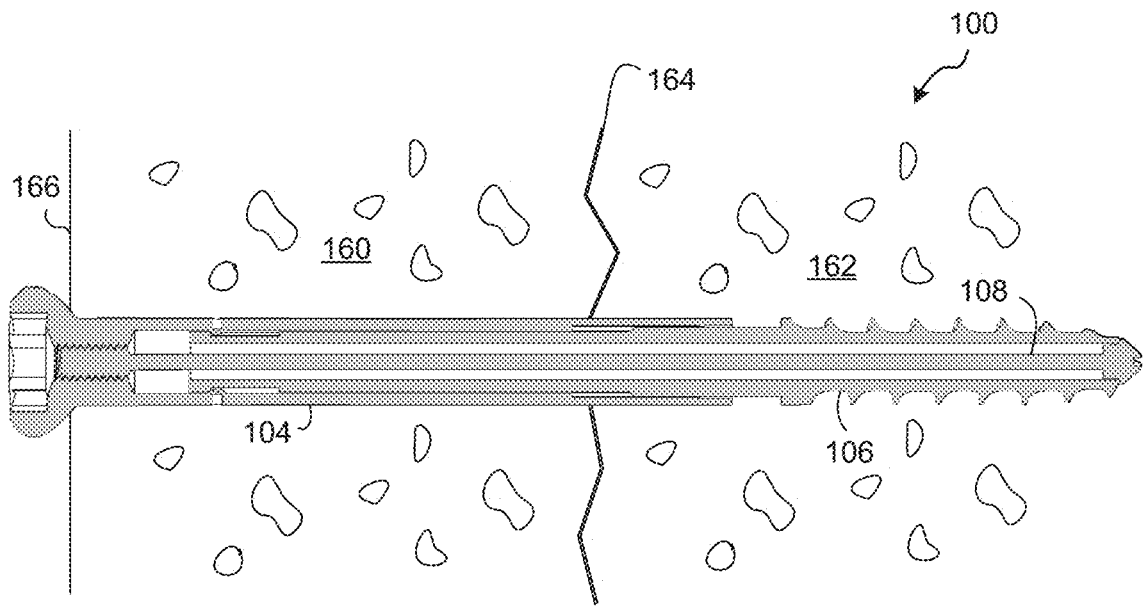

FIGS. 6A and 6B are side elevation, section views of the bone screw 100 of FIG. 1, upon initial insertion into bone, and upon further insertion to tension the bone screw, respectively. As shown, the bone screw 100 may be used, in this particular implementation, to secure a first bone portion 160 to a second bone portion 162. The first bone portion 160 and the second bone portion 162 may be fragments of a single fractured bone, or they may be previously separate bone structures that are to be brought together and fused and/or otherwise secured to each other.

As shown, the first bone portion 160 and the second bone portion 162 may initially be separated from each other by an interface 164, at which a gap exists between the first bone portion 160 and the second bone portion 162. The first bone portion 160 may be nearer the surgeon and may have an exterior cortex 66.

The bone screw 100 may first be inserted into the pilot hole. In order to reach the position shown in FIG. 6A, torque may be applied to the head 112 of the bone screw 100 such that the bone-engaging threads 122 engage the second bone portion 162. Torque may continue to be applied until the head 112 seats on the exterior cortex 166 of the first bone portion 160 as shown.

With the head 112 seated against the exterior cortex 166, further torque may be applied to the bone screw 100 in order to drive the bone-engaging threads 122 further into the second bone portion 162 and draw the second bone portion 162 toward the first bone portion 160, closing the gap at the interface 164. Leaving the bone screw 100 in this configuration may hold the second bone portion 162 and the first bone portion 160 together for a period of time, but once stress is applied to the first bone portion 160 and the second bone portion 162, or once bone proximate the interface 164 begins to subside, a gap may form again at the interface 164.

Thus, further torque may be applied to the bone screw 100 to cause the bone screw 100 to elongate, applying compression between the first bone portion 160 and the second bone portion 162 even after such motion and/or subsidence occurs. More specifically, elongation of the bone screw 100 may occur as the shank 144 of the tension member 108 elongates, resulting in the configuration shown in FIG. 6B. The tension member 108, in turn, may pull the distal member 106 back toward the proximal member 104, compressing the second bone portion 162 against the first bone portion 160. Such compression may continue as long as the tension member 108 is elongated. Use of a superelastic material to form the tension member 108 may help provide a continuous level of compression between the first bone portion 160 and the second bone portion 162 as the bone screw 100 shortens, rather than providing a high level of compression at maximum elongation, followed by lesser compression as the bone screw 100 is permitted to shorten due to motion of the first bone portion 160 and the second bone portion 162, or due to subsidence.

As discussed previously, the length of the bone screw 100, and therefore the compression applied by the tension member 108 and the compression applied by the tension member 108, may be limited by the operation of the length limiting mechanism 210. Thus, as the bone screw 100 reaches the length shown in FIG. 6B, the protrusions 212 of the proximal member 104 may abut the shoulder 216 of the distal member 106 to prevent further elongation of the bone screw 100. This limitation may help to ensure that the tension member 108 does fail in tension and does not apply excessive compression across the interface 164.

The configuration of the bone screw 100 may help control the manner in which torque is applied to the bone screw 100 to insert and then elongate the bone screw 100. A threshold torque may be required to cause the bone screw 100 to elongate: this threshold torque may generally be higher than the level of torque required to drive the bone screw 100 into the first bone portion 160 and the second bone portion 162, up until the head 112 contacts the exterior cortex 166 of the first bone portion 160.

Figure 7:
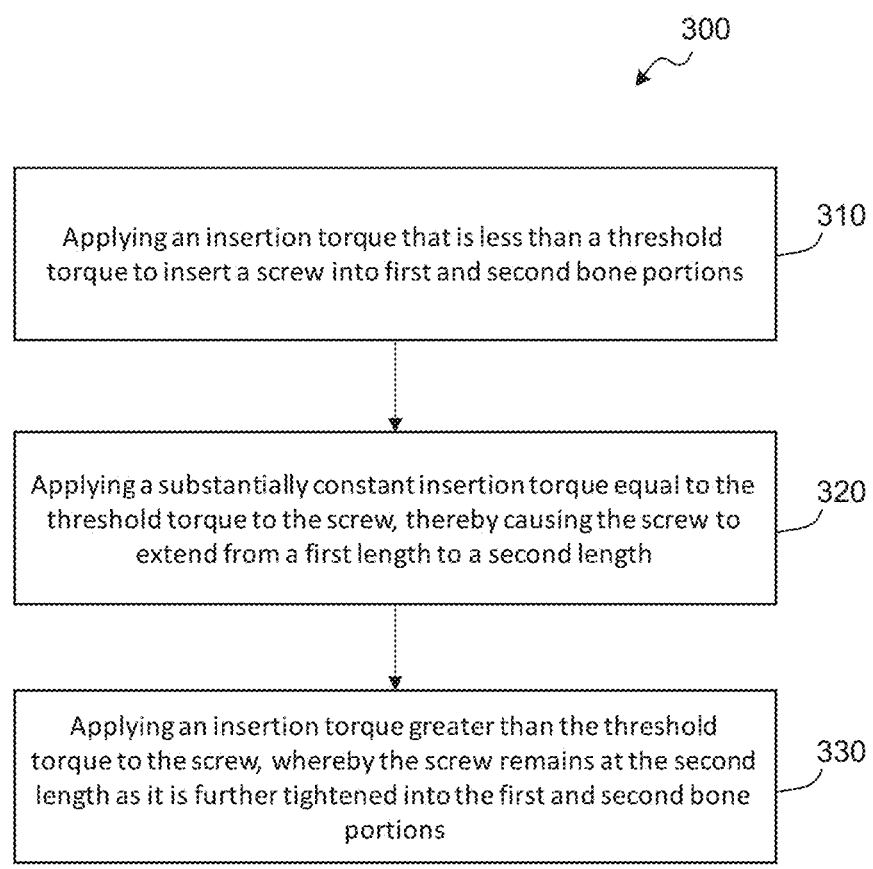
FIG. 7 is a flowchart depicting a method of inserting a bone screw into bone, according to one embodiment.

FIG. 7 is a flowchart depicting a method 300 of inserting the bone screw 100 into bone, according to one embodiment. As shown, the method 300 may commence with a step 310 in which an insertion torque is applied to the bone screw 100. As mentioned above, this insertion torque may be less than the threshold torque required to cause elongation of the bone screw 100. The step 310 may continue until the head 112 seats against the exterior cortex 166.

The method 300 may then proceed to a step 320 in which further torque is applied, at a level equal to the threshold torque required to elongate the bone screw 100, until the bone screw 100 is fully elongated. Use of a superelastic, material (such as Nitinol) in the tension member 108 may cause the threshold torque to remain generally constant as the bone screw 100 elongates. This is distinct from conventional materials, which may require an increasing level of tension (and therefore increasing torque) as strain in the material increases.

Once the bone screw 100 has elongated fully, the method 300 may proceed to a step 330 in which an insertion torque is again applied at a higher level than the threshold torque as the bone screw 100 is further tightened in the first bone portion 160 and the second bone portion 162. This tightening may not further elongate the bone screw 100, which may be at its maximum length. However it may, for example, seat the head 112 deeper in the exterior cortex 166 and apply additional compression across the interface 164 between the first bone portion 160 and the second bone portion 162.

The bone screw 100 may not be designed for insertion along a guide wire. Full assembly of the bone screw 100 prior to insertion may interfere with use of a guide wire, as the tension member 108 may occupy the variable-length cavity 130 that would otherwise receive the guide wire. However, in alternative embodiments, a bone screw may be designed for insertion along a guide wire and subsequent assembly, and elongation, in-situ. One such embodiment will be shown and described subsequently in connection with FIGS. 11 through 17.

Figure 8:
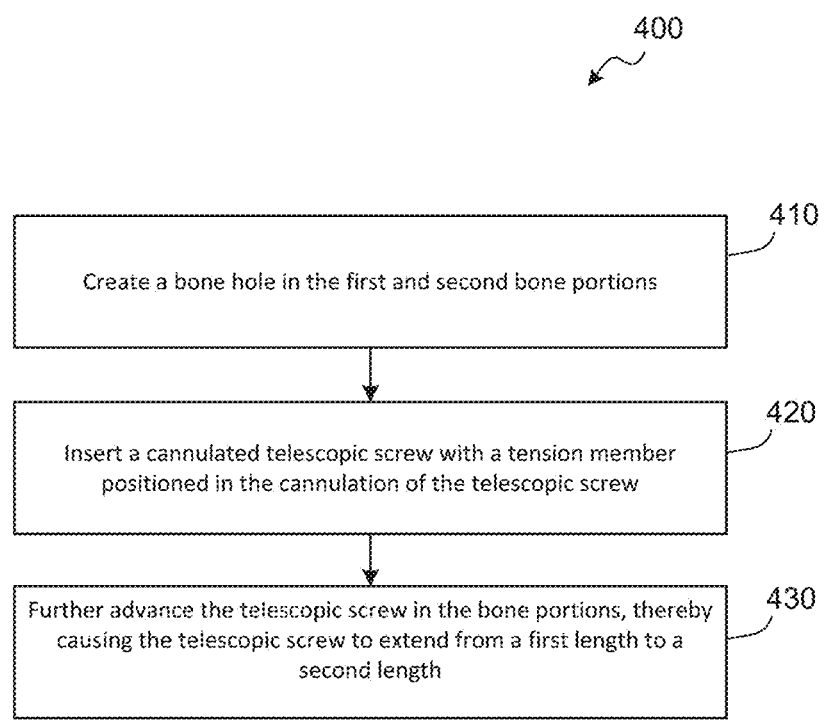
FIG. 8 is a flowchart depicting a method of inserting a bone screw into bone along a guide wire, according to one embodiment.

FIG. 8 is a flowchart depicting a method 400 of inserting a bone screw, such as the bone screw 100 of FIGS. 1A through 5, into bone according to one embodiment. The method 400 assumes that the bone screw 100 is used to secure two bone portions (for example, two fragments of a single bone to be repaired, or two bones to be locked together); similar methods may be envisioned for use of the bone screw 100 to secure an implant to bone.

As shown, the method 400 may commence with a step 410 in which a bone hole is formed in the first and second bone portions. As mentioned previously, this may be done with a stepped pilot drill bit (not shown) that forms a smaller hole in the second bone portion 162, and a larger hole in the first bone portion 160. In alternative embodiments, the bone screw 100 may be self-tapping, and the step 410 may be omitted.

The method 400 may proceed to a step 420 in which the bone screw 100, in a fully-assembled state (including the tension member 108), is inserted into the holes formed in the first bone portion and in the second bone portion 162. This may be done without using a guide wire. Insertion of the bone screw 100 may be carried out by rotating the bone screw 100 with a driver (not shown) until the head 112 of the bone screw 100 abuts the exterior cortex 166 of the first bone portion 160 (the proximal bone portion).

In a step 430, the bone screw 100 may be further advanced, causing the bone screw 100 to extend from a first length to a second length. The first length may be the base (unelongated) length of the bone screw 100, as shown in FIG. 6A. The second length may be the fully extended length of the bone screw 100, as shown in FIG. 6B. In the alternative, the second length may less than the maximum length of the bone screw 100. Elongation of the bone screw 100 pursuant to the step 430 may be carried out by further rotating the bone screw 100 with the driver such that the distal member 106 moves distally relative to the proximal member 104. This rotation may be carried out until the bone screw 100 has reached the second length.

After performance of the step 430, the tension member 108 may be under tension, and may exert compressive force urging the distal member 106 to move proximally back toward the proximal member 104. This compressive force may be propagated to the interface 164 between the first bone portion 160 and the second bone portion 162 to accelerate healing and/or fusion.

Those of skill in the art will recognize that the method 300 of FIG. 7 and the method 400 of FIG. 8 may be performed with other extendable bone screws besides the bone screw 100 of FIGS. 1A through 5. Further, the bone screw 100 may be used in connection with surgical methods besides the method 300 and the method 400.

Returning to the bone screw 100 of FIGS. 1A through 5, as mentioned previously, the tension member 108 may be formed of a superelastic material such as Nitinol. The manner in which this affects performance of the bone screw 100 will be further shown and described in connection with FIG. 9A.

Figure 9A:
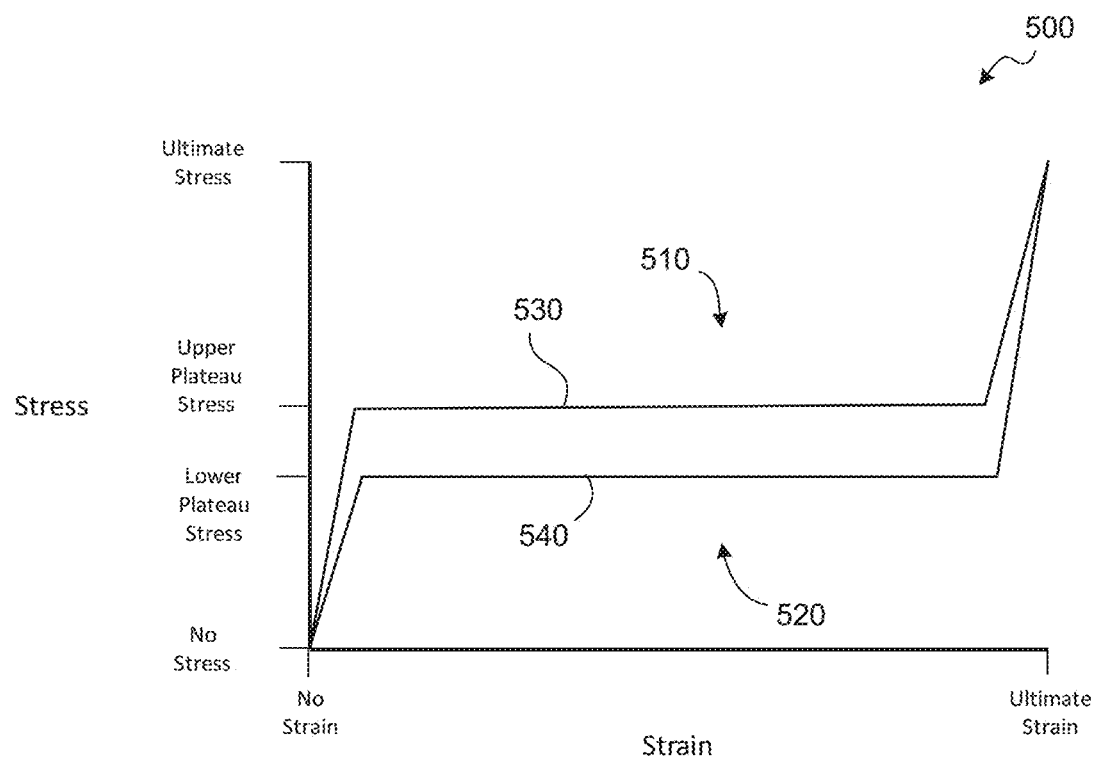
FIG. 9A is a diagram depicting stress versus strain for an exemplary superelastic material.

FIG. 9A is a diagram 500 depicting stress versus strain for an exemplary superelastic material. The diagram 500 is idealized and is only meant to indicate general properties of superelastic materials.

As shown, the diagram 500 may have a strain curve 510, showing stress versus strain under increasing stress, and a recovery curve 520, showing stress versus strain as stress is reduced. The strain curve 510 may have a horizontal portion 530, showing that the material will undergo steadily increasing strain as an upper plateau stress is applied. The strain range represented by horizontal portion 530 is referred to herein as superelastic strain. The strain at the left end of horizontal portion 530 represents the beginning of the transition of the superelastic material from a first crystal structure phase such as austenite to a second crystal structure phase such as martensite. The right end of horizontal portion 530 represents the complete transformation to the second crystal structure phase, and this represents the limit of superelastic strain. The span between the left and right ends of horizontal portion 530 is referred to herein as the superelastic zone. This upper plateau stress may be the stress experienced by the tension member 108 as the threshold level of torque is applied. The horizontal portion 530 may be generally horizontal, showing that application of torque at the threshold level (rather than at an increasing level) will cause the tension member 108 to continue to elongate.

The recovery curve 520 may also have a horizontal portion 540, showing that the material will undergo a steadily reducing strain, while a constant level of stress is maintained. This shows the performance of the bone screw 100 as the bone screw 100 is permitted to shorten again, due to shifting of the first bone portion 160 and the second bone portion 162 and/or subsidence of the first bone portion 160 and/or the second bone portion 162. The strain level experienced by the tension member 108 may equate to the compressive force applied by the bone screw 100, urging the first bone portion 160 and the second bone portion 162 together. The length and horizontal orientation of the horizontal portion 540 indicate how relatively steady compression at the lower plateau stress level may be maintained even as considerable shortening of the bone screw 100 occurs. Thus, the bone screw 100 may maintain compression to help the first bone portion 160 and the second bone portion 162 to heal and/or fuse, even while the bone screw 100 is shorter than its maximum length at the time of surgery.

Figure 9B:
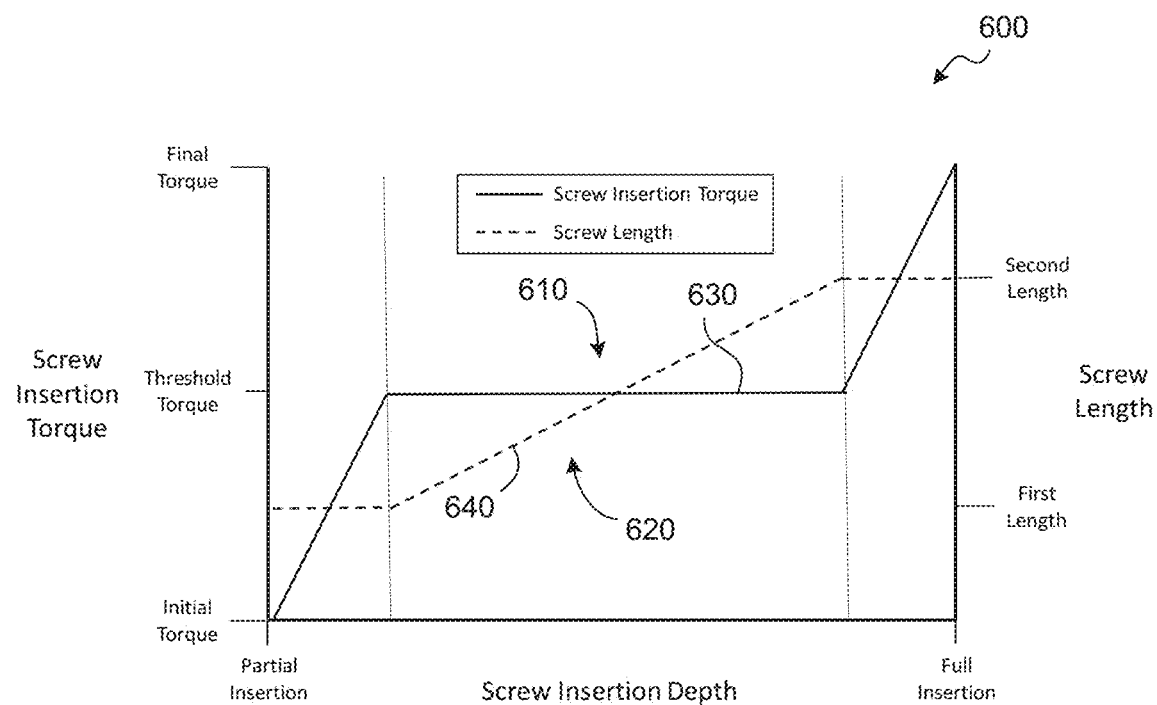
FIG. 9B is a diagram depicting changes in insertion torque and screw length during screw insertion.

FIG. 9B is a diagram 600 depicting changes in insertion torque and screw length during screw insertion. A torque curve 610 depicts the torque needed to advance the bone screw 100. A length curve 620 shows the length of the bone screw 100. The torque curve 610 may rise gradually and then level off at the threshold torque one the bone screw 100 has been fully inserted and begins to elongate. A horizontal portion 630 of the torque curve 610 may indicate how the insertion torque remains relatively constant during elongation of the bone screw 100. In the length curve, this elongation is shown by a flat portion 640 with a constant upward slope. Prior to application of the threshold torque, and after the bone screw 100 reaches its maximum length, the length curve 620 is horizontal, reflecting a lack of change in length of the bone screw 100.

Figure 10A:
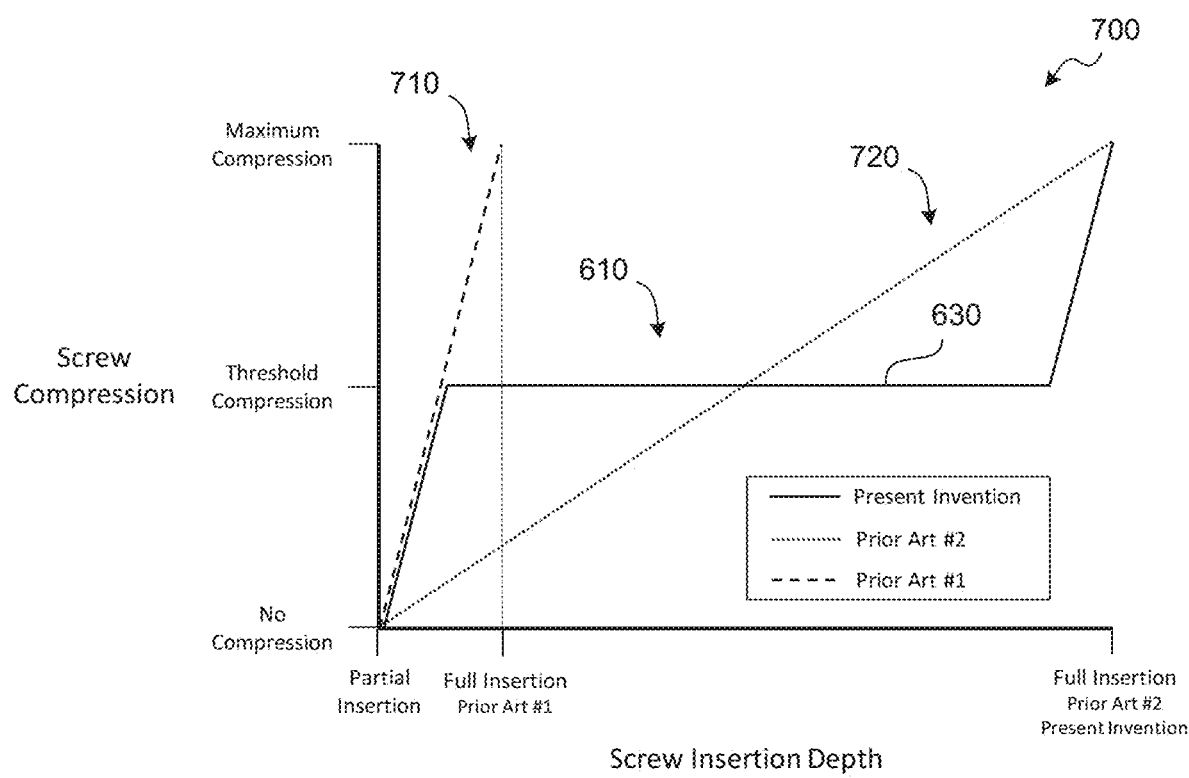
FIG. 10A is a diagram depicting changes in screw compression during screw insertion.

FIG. 10A is a diagram 700 depicting changes in screw compression during insertion of the bone screw 100, as in FIG. 9B. The torque curve 610 is compared with a torque curve 710 for "Prior Art #1," which is a standard bone screw that does not elongate, and a torque curve 720 for "Prior Art #2," which is a bone screw with elongation provided by a more conventional coil spring that is not formed of a superelastic material.

As shown, the torque curve 710 has a constant slope, which is relatively steep, reflecting the fact that a conventional bone screw does not elongate significantly. The insertion depth of the screw is thus limited by the excessively high torque required to deepen insertion of the screw, and the correspondingly high tension applied to the screw (and compression applied across the interface 164). Excessive torque may cause the screw to fail during insertion, and excessive compression may cause the bone to fail. Accordingly, insertion depth is limited, and any subsidence or motion in the first bone portion 160 and/or the second bone portion 162 may be expected to negate compression across the interface 164.

The torque curve 720 also has a constant slope, which is less steep than that of the torque curve 710. This reflects the elongation provided by the coil or other conventional spring, which provides greater elongation than a conventional screw, but still requires increasing torque to obtain greater insertion depth. Again, any relative motion and/or subsidence in the first bone portion 160 and/or the second bone portion 162 may reduce the elongation in the spring, causing the compression applied across the interface between bone portions to decrease in proportion to the slope of the torque curve 720. This concept will be further illustrated in FIG. 10B.

Figure 10B:
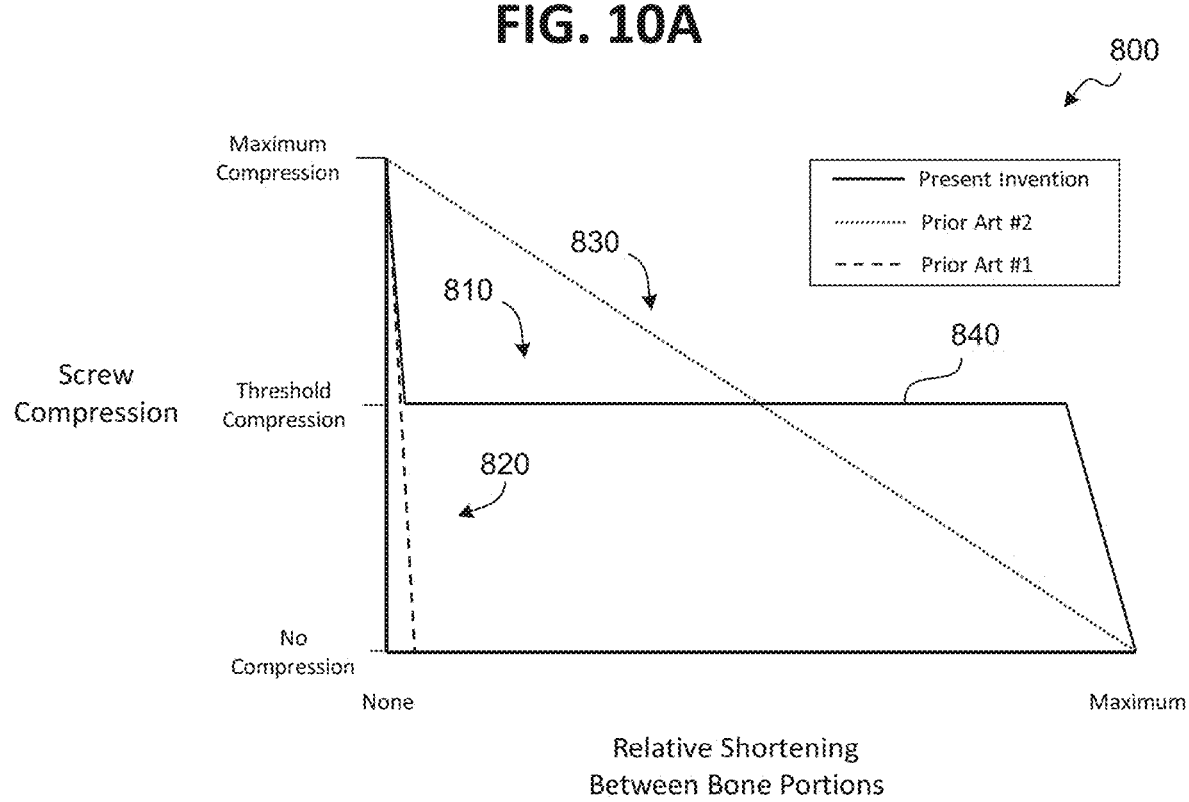
FIG. 10B is a diagram depicting changes in screw decompression during relative shortening between bone portions.
Figure 11A:
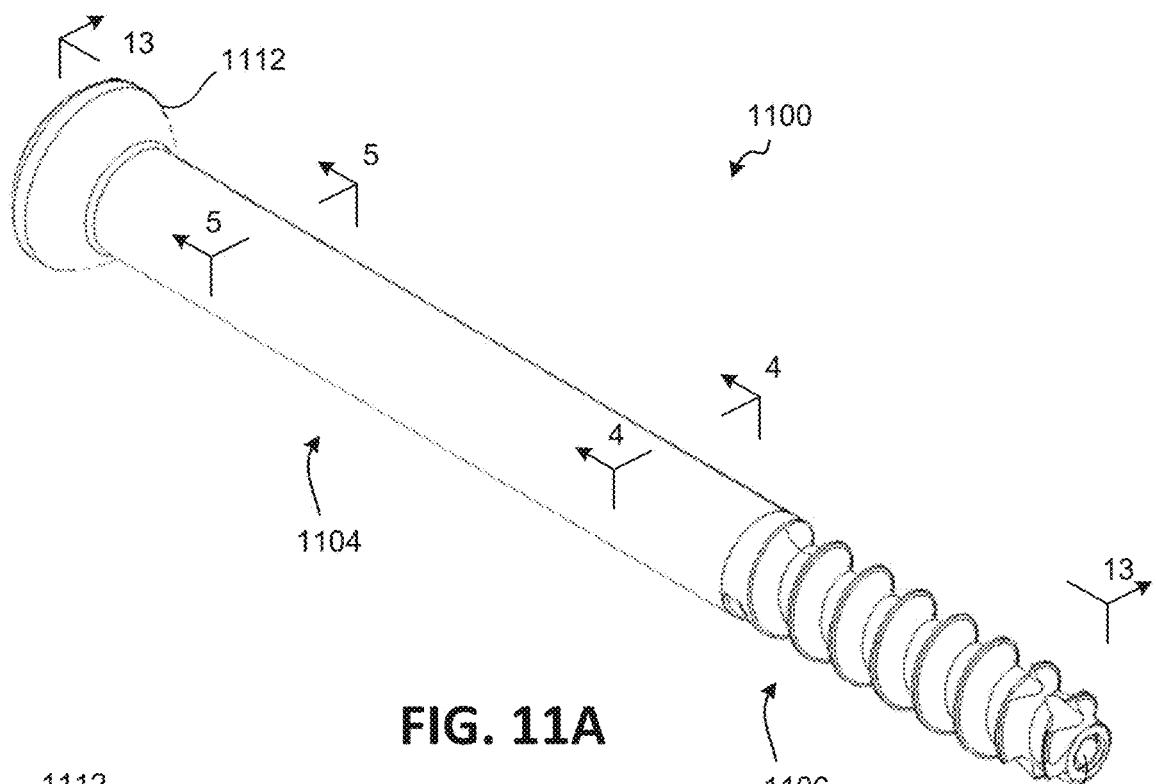
FIGS. 11A, 11B, 11C, and 11D are perspective, side elevation, front elevation, and rear elevation views, respectively, of a bone screw according to another embodiment.
Figure 11B:
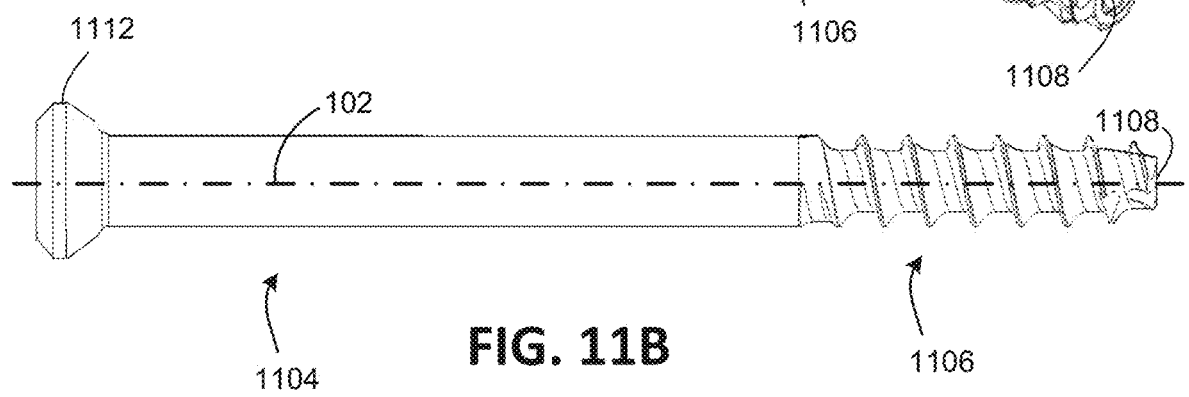
Figures 11C, 11D:
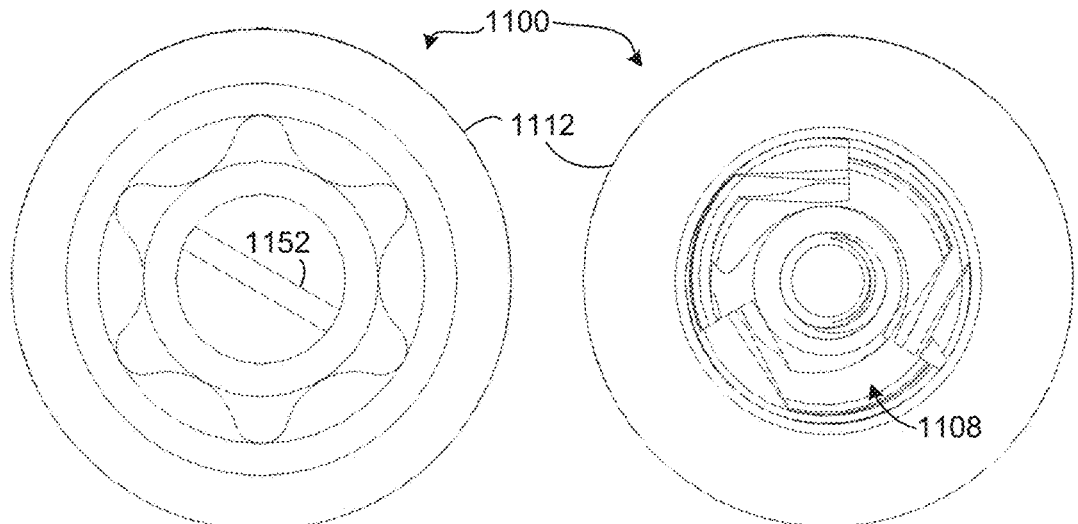

FIG. 10B is a diagram 800 depicting changes in screw decompression during relative shortening between bone portions. A decompression curve 810 is shown for the bone screw 100, as well as a decompression curve 820 for Prior Art #1 and a decompression curve 830 for Prior Art #2. The decompression curve 820 and the decompression curve 830 illustrate how compression applied across the interface 164 between the first bone portion 160 and the second bone portion 162 decreases in response to shortening of the bone screw. The decompression curve 810 may have a horizontal portion 840.

With the conventional bone screw, only a minimal amount of strain in the screw needs to be relieved before all compression across the interface 164 is lost. With the bone screw with a conventional spring, relief of strain reduces the compression across the interface 164 in relation to the slope of the decompression curve 830, which may be the inverse of the slope of the torque curve 720 of the diagram 700. Accordingly, the only way to maintain an optimal level of compression across the interface 164 (for example, a level of compression close to the "Threshold Compression" of FIG. 10B) with this screw is to apply excessive compression at the time of surgery, so that strain relief only reduces the compression applied by the screw down from the excessive compression level to the healthy compression level. As mentioned previously, application of excessive compression (i.e., by applying high torque to the screw) can result in failure of the screw and/or the surrounding bone.

By contrast, the decompression curve 810 illustrates how a broad range of strain relief in the bone screw 100 can occur without significantly changing the level of compression applied across the interface 164. The bone screw 100 need not be torqued excessively in order to accomplish this. Rather, the bone screw 100 may advantageously be inserted only far enough to remain in the horizontal portion 840 of the decompression curve 810. In some embodiments, the horizontal portion 840 may extend across a length of 0 to 5 mm. More precisely, the horizontal portion 840 may extend across a length of 1 to 4 mm. Still more precisely, the horizontal portion 840 may extend across a length of 1.5 to 3 mm. Yet more precisely, the horizontal portion 840 may extend across a length of 2 mm.

This concept may apply across all of FIGS. 9A, 9B, 10A, and 10B. For example, with reference to FIG. 9A, the tension member 108 of the bone screw 100 may be tensioned only enough that the stress and strain experienced by the tension member 108 remains in the horizontal portion 530 of the strain curve 510. This limit may be provided by the length limiting mechanism 210, which may limit elongation of the tension member 108 during insertion of the bone screw 100 to keep stress in the tension member 108 from moving beyond (i.e., to the right of) the horizontal portion 530. Relief of stress in the tension member 108 may thus only traverse the horizontal portion 540 of the recovery curve 520. This is reflected in FIG. 9B, in which further torque applied to the bone screw 100 after the bone screw 100 has traversed the horizontal portion 630 of the torque curve 610, may not cause further elongation of the bone screw 100. All of this may be transparent to the surgeon, who can simply drive the screw in a generally conventional manner.

The bone screw 100 of FIGS. 1A through 5 is only one of many embodiments of the present disclosure. Those of skill in the art will recognize that many variations could be conceived. For example, in some embodiments, the bone-engaging threads 122 may be adapted for the type of bone being penetrated. This may entail use of more or fewer bone-engaging threads 122, or bone-engaging threads 122 with different shapes and/or sizes, than those depicted in FIGS. 1A through 5. In other embodiments, the proximal member 104 and the distal member 106 may be reconfigured such that the proximal member (not shown) has a distal end that resides within the proximal end of the distal member (not shown). Further, as set forth above, a wide variety of torque transmission features, length limiting mechanisms, bending transmission features, driver engagement features, and/or the like may be used, in addition to or in place of those of the bone screw 100.

Figure 17:
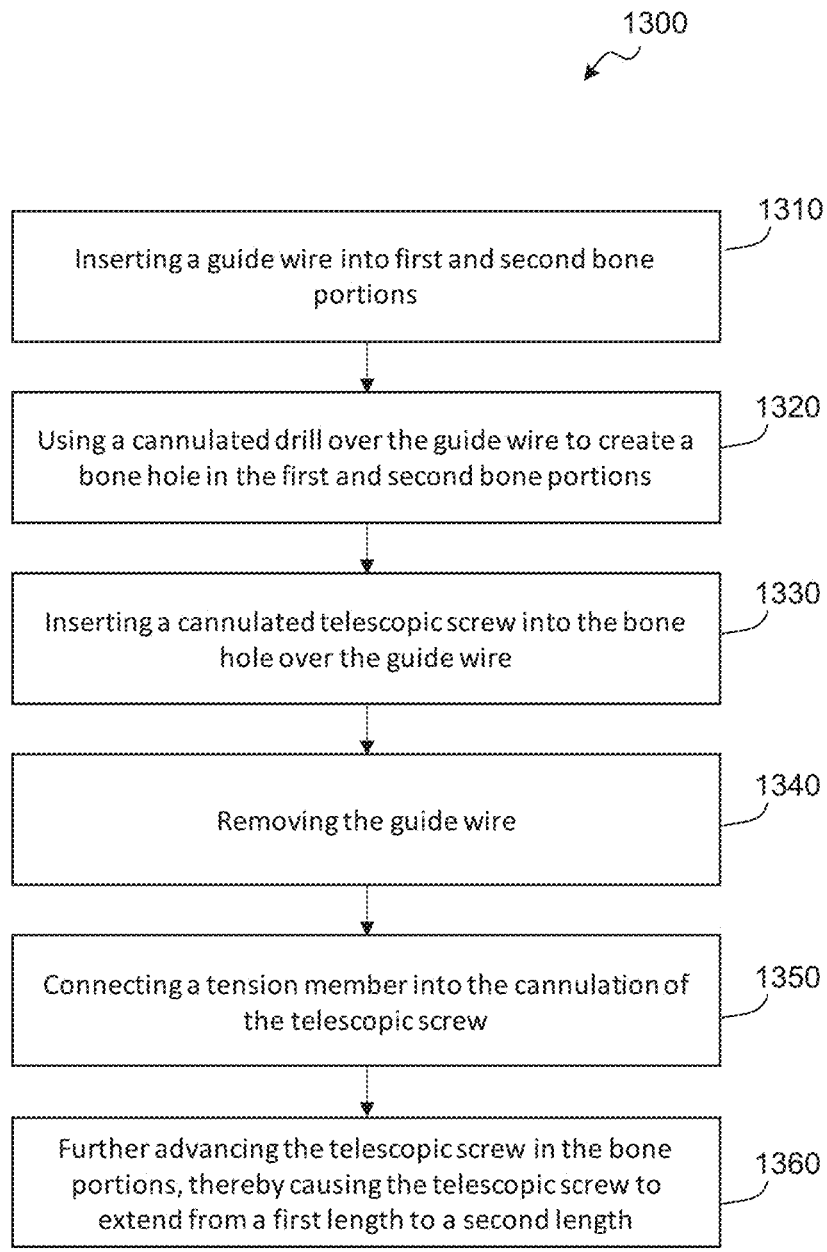
FIG. 17 is a flowchart depicting a method of inserting a bone screw into bone, according to another embodiment.

In some embodiments, it may be desirable to use a variable-length bone screw in conjunction with a guide wire, as will be set forth in the method 1300 of FIG. 17. FIGS. 11A through 15 show a bone screw 1100 that is configured to facilitate use with a guide wire.

Figure 12:
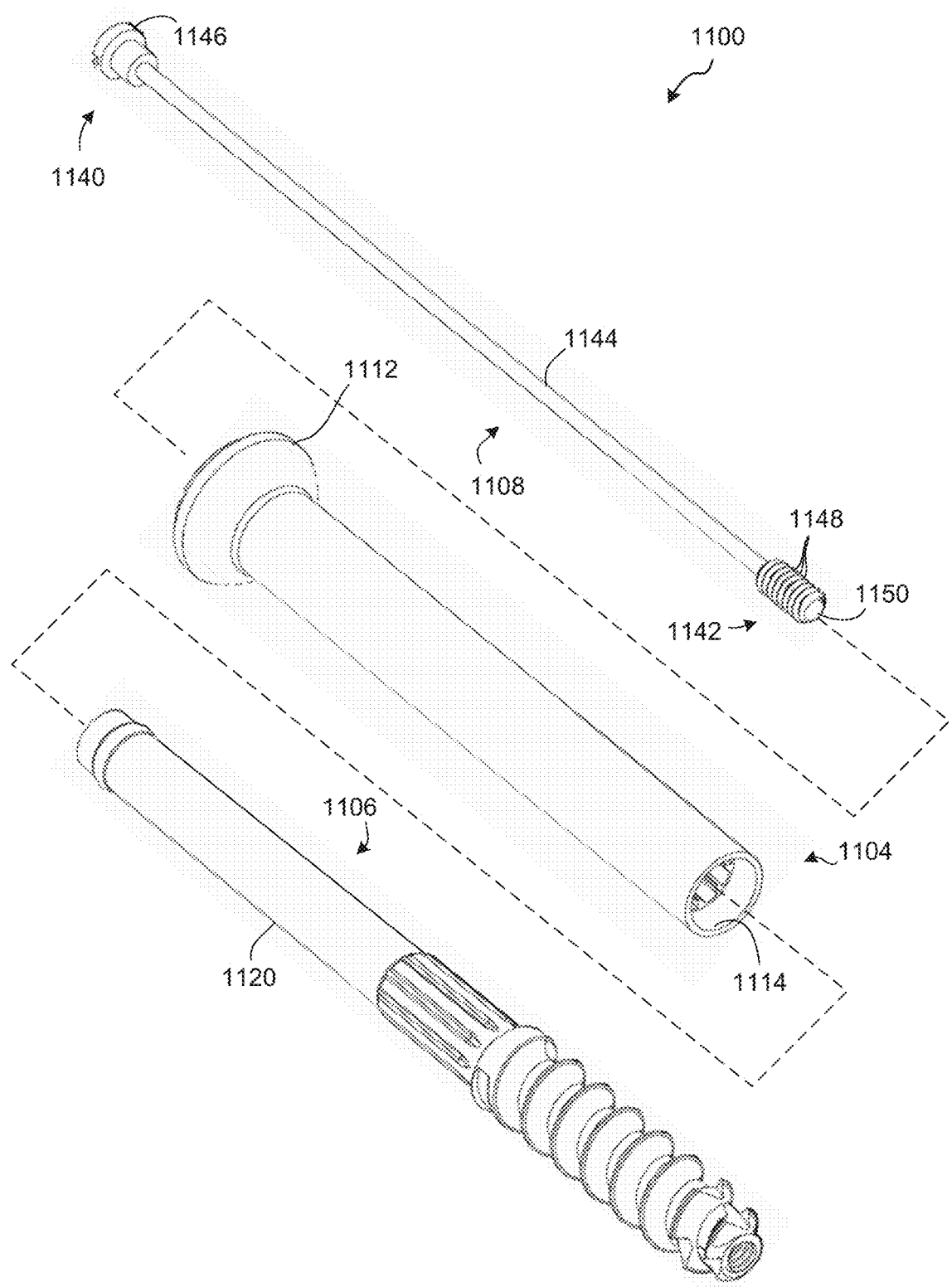
FIG. 12 is an exploded, perspective view of the bone screw of FIG. 11.
Figures 13A, 13B, 13C, 13D:
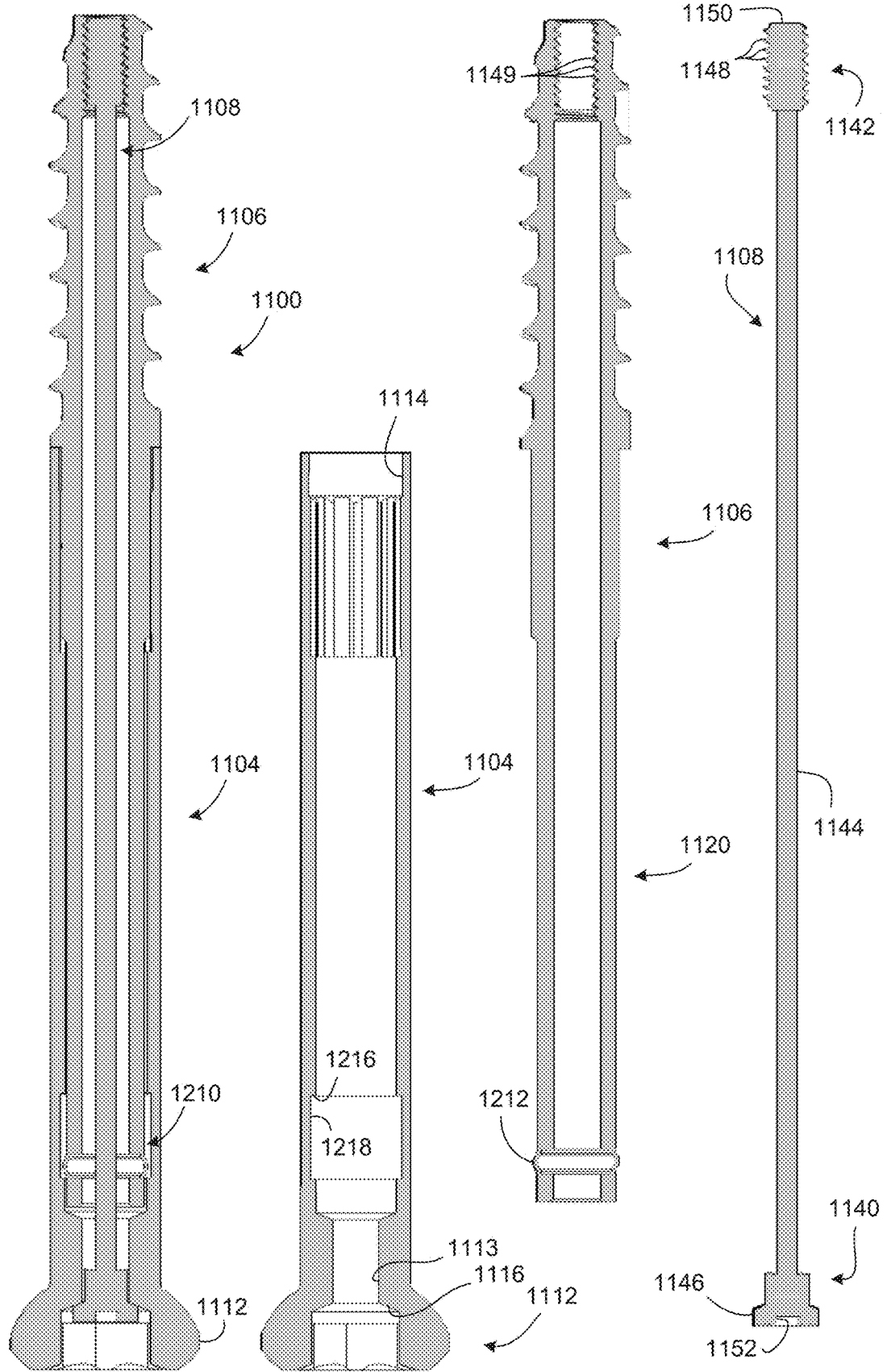
FIGS. 13A, 13B, 13C, and 13D are side elevation, section views of the bone screw, the proximal member, the distal member, and the tension member, respectively, of FIG. 11.
Figure 14:
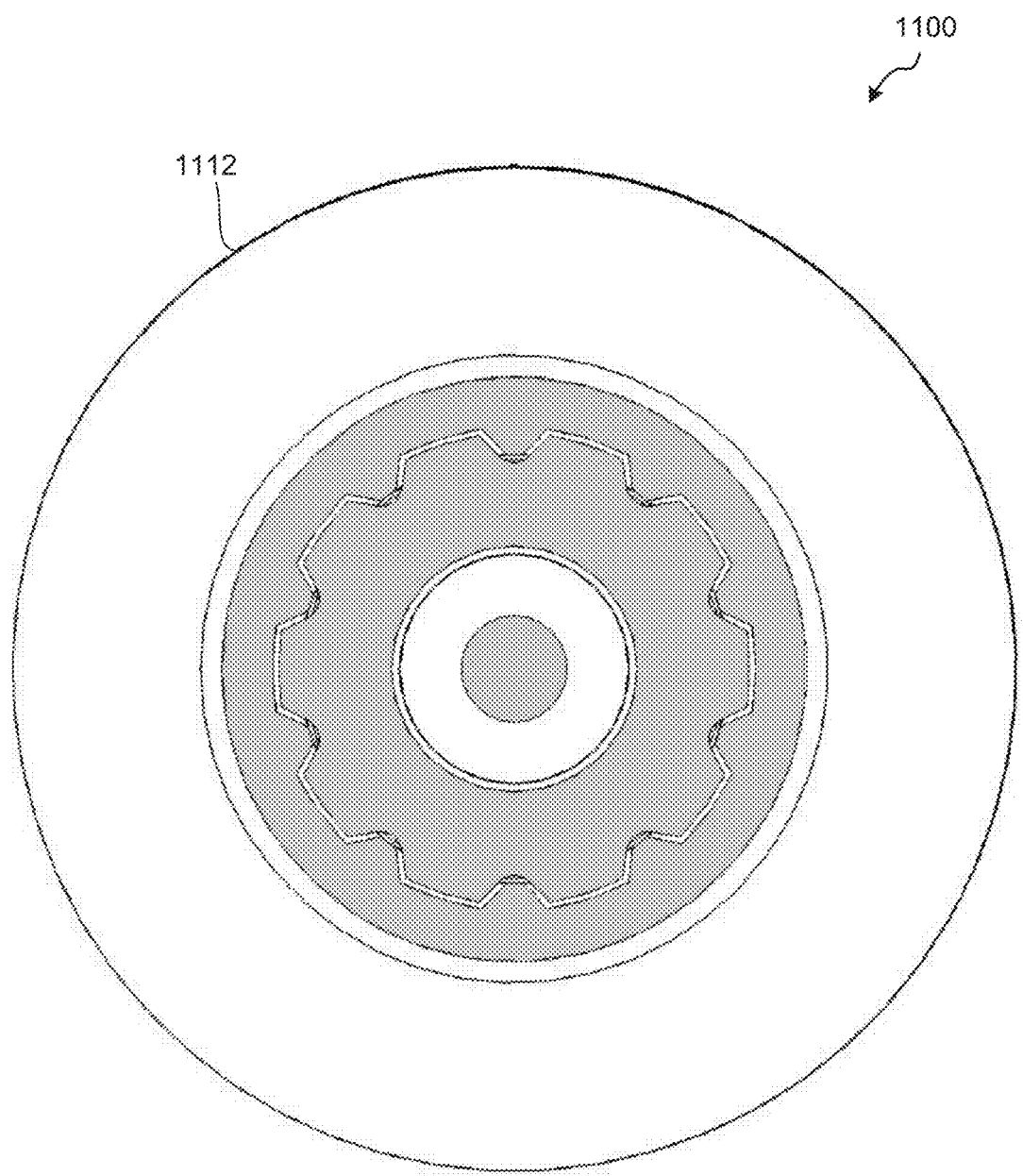
FIG. 14 is a front elevation, section view of the bone screw of FIG. 11.
Figure 15:
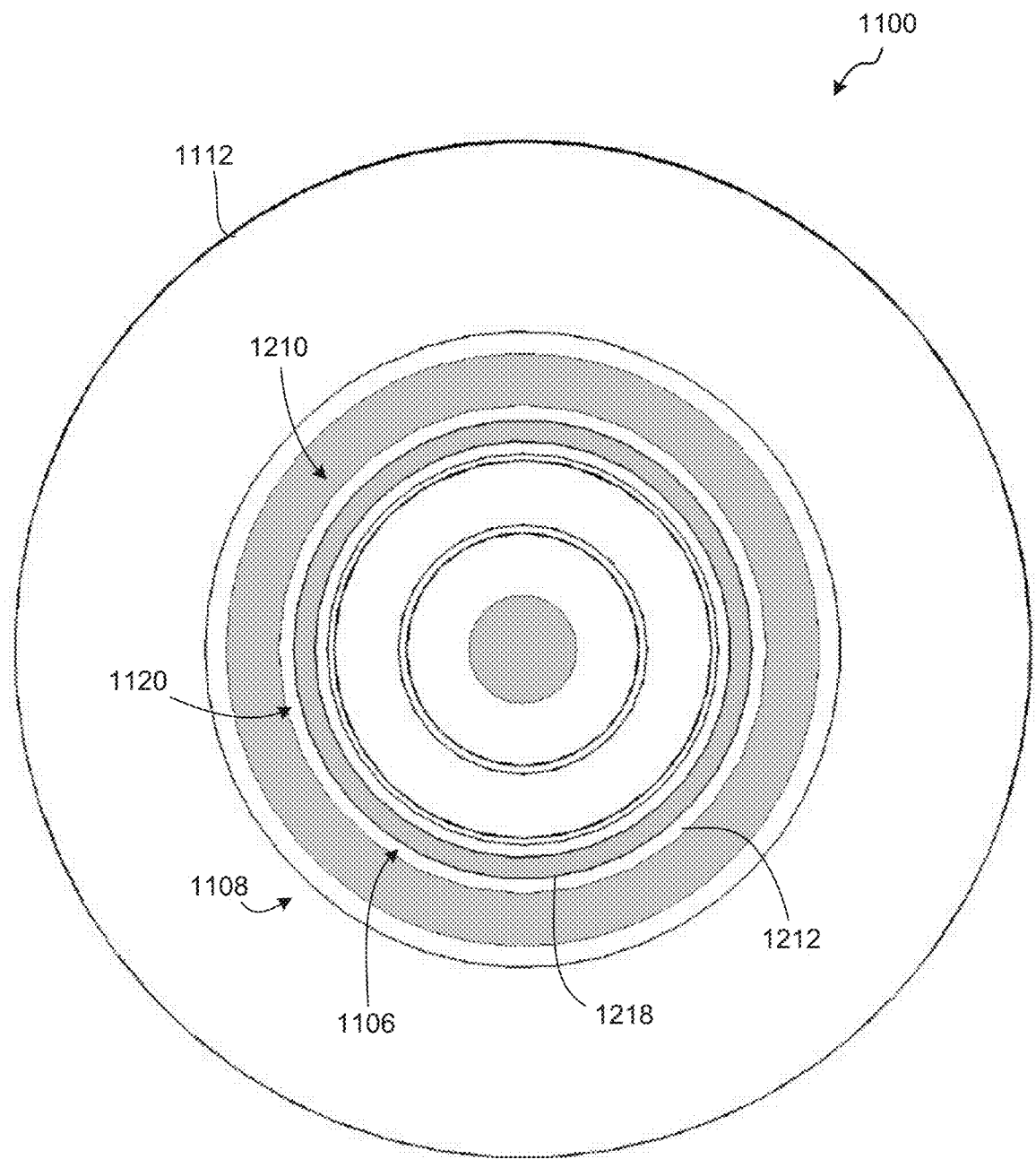
FIG. 15 is another front elevation, section view of the bone screw of FIG. 11.

The bone screw 1100 may have a longitudinal axis 102, a proximal member 1104, a distal member 1106, and a tension member 1108. FIGS. 11A, 11B, 11C, and 11D are perspective, side elevation, front elevation, and rear elevation views, respectively, of the bone screw 1100. FIG. 12 is an exploded, perspective view of the bone screw 1100. FIGS. 13A, 13B, 13C, and 13D are side elevation, section views of the bone screw 1100, the proximal member 1104, the distal member 1106, and the tension member 1108, respectively. FIG. 14 is a front elevation, section view of the bone screw 1100. FIG. 15 is another front elevation, section view of the bone screw 1100. Various parts of the bone screw 1100 may be identical or similar to their counterparts on the bone screw 100: they will not be described again here. All statements made regarding the bone screw 100 apply to the bone screw 1100, unless they would be contradicted by the differences between the two.

The bone screw 1100 may be configured to allow the tension member 1108 to be inserted into the proximal member 1104 and the distal member 1106 after the remainder of the bone screw 1100 (i.e., the proximal member 1104 and the distal member 1106) have been assembled together and inserted into the bone. The tension member 1108 may be designed to be inserted into and coupled to the proximal member 1104 and the distal member 1106 after the proximal member 1104 and the distal member 1106 have been implanted in the bone.

Specifically, like the tension member 108 of the bone screw 100 of FIGS. 1A through 5, the tension member 1108 may have a proximal end 1140, a distal end 1142, and a shank 1144, extending along the longitudinal axis 102, that connects the proximal end 1140 to the distal end 1142.

However, in place of the proximal threads 146 of the tension member 108, the proximal end 1140 of the tension member 1108 may have a head 1146 that is wider than the shank 1144. The proximal member 1104 may have a head 1112 with an aperture 1113 leading into the interior of the proximal member 1104, defining a surrounding shoulder 1116 on which the head 1146 of the tension member 1108 can rest.

The distal end 1142 may have distal threads 1148 that facilitate coupling of the tension member 1108 to the distal member 1106 engagement of the distal threads 1148 with interior threads 1149 of the distal member 1106. The distal end 1142 may further have a distal tip (not shown) that is sufficiently sharp for bone penetration, or alternatively, may have a distal tip 1150, as shown, that is blunt, as the distal tip 1150 need not penetrate the bone because the tension member 1108 may not be inserted into the bone until after penetration has already been performed via formation of the pilot hole and/or insertion of the distal member 1106 into the bone.

The head 1146 may have one or more driver engagement features that are operable independently of the driver engagement feature 230 of the head 1112. For example, the head 1146 may have a slot 1152 (shown in FIG. 11C) that facilitates rotation of the tension member 1108 with a driver such as a flat-head screwdriver.

In use, the proximal member 1104 and the distal member 1106 may be assembled and driven into the bone over a guide wire, as will be set forth in the method 1300 of FIG. 17. Then the guide wire may be removed, and the tension member 1108 may be inserted into the proximal member 1104 and the distal member 1106 by inserting the distal end 1142 through the aperture 1113, through the proximal member 1104, and into the distal member 1106 such that the distal threads 1148 of the distal end 1142 reach the interior threads 1149 of the distal member 1106. A driver may be used to rotate the tension member 1108, causing the distal threads 1148 to engage the interior threads 1149. When the distal threads 1148 have been fully received in the interior threads 1149, the head 1146 of the proximal end 1140 of the tension member 1108 may rest on the shoulder 1116 of the head 1112 of the proximal member 1104, preventing further distal motion of the head 1146.

With the tension member 1108 in place within the proximal member 1104 and the distal member 1106, the bone screw 100 may be further driven into the bone to move the distal member 1106 distally relative to the proximal member 1104, causing the tension member 1108 to elongate. The head 1146 of the tension member 1108 may continue to press against the shoulder 1116 of the proximal member 1104 as the interior threads 1149 of the distal member 1106 move distally.

Like the bone screw 100, the bone screw 1100 may have a length limiting mechanism 1210 that controls the extent to which the bone screw 1100 can increase in length. The length limiting mechanism 1210 may function in a manner similar to that of the length limiting mechanism 210 of the bone screw 100.

Specifically, the length limiting mechanism 1210 may have a distal stop feature and a proximal stop feature that engage each other when the distal member 1106 has reached its maximum displacement relative to the proximal member 1104 to prevent further distal motion of the distal member 1106 relative to the proximal member 1104. The distal stop feature may be a protrusion 1212 on a distal shank 1120 of the distal member 1106. The protrusion 1212 may extend radially outwardly, away from the longitudinal axis 102 of the bone screw 1100. The proximal stop feature may be a shoulder 1216 defined at the distal end of a relief 1218 formed in a proximal interior surface 1114 of the proximal member 1104. The protrusion 1212 may extend radially into the relief 1218 such that distal motion of the distal member 1106 causes the protrusion 1212 to abut the shoulder 1216, arresting further distal motion of the distal member 1106 relative to the proximal member 1104.

Figure 16A:
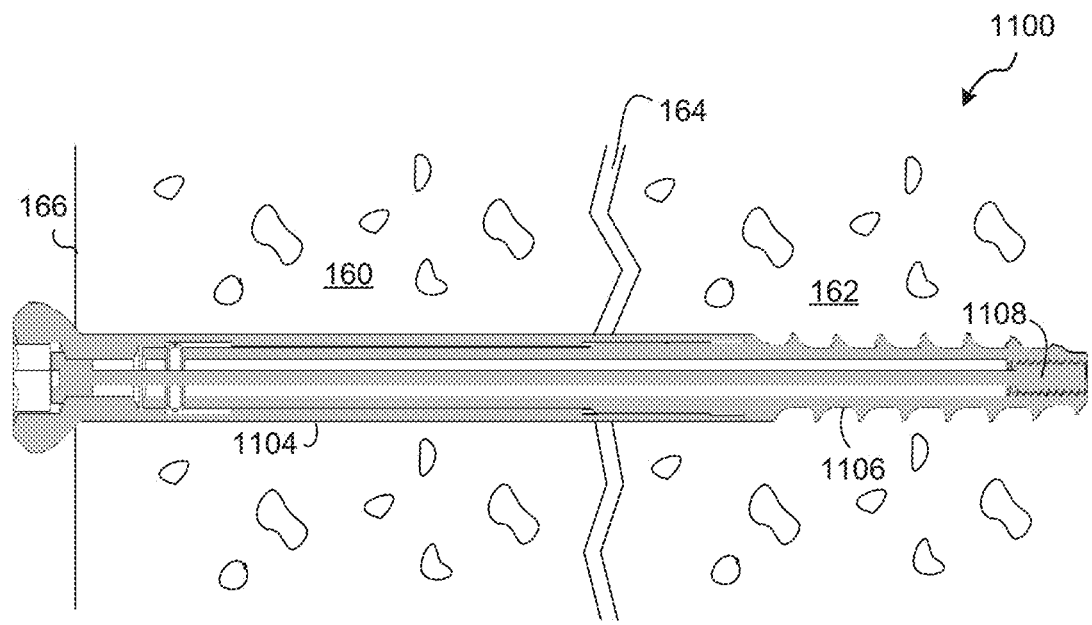
FIGS. 16A and 16B are side elevation, section views of the bone screw of FIG. 11, upon initial insertion into bone, and upon further insertion to tension the bone screw, respectively.
Figure 16B:
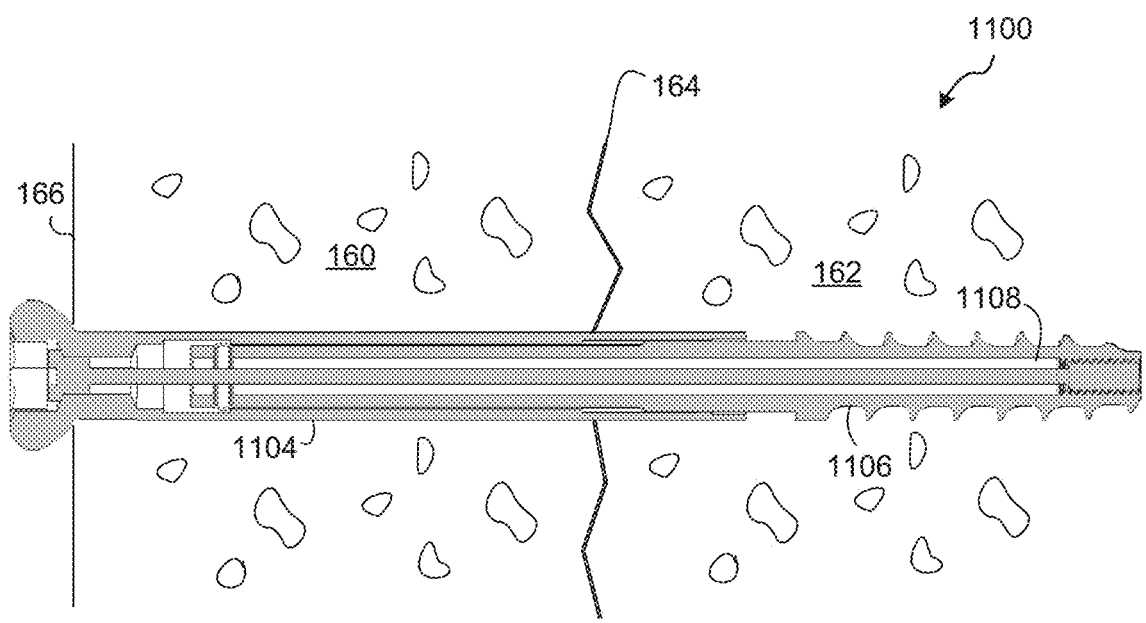

FIGS. 16A and 16B are side elevation, section views of the bone screw 1100 of FIG. 11, upon initial insertion into bone, and upon further insertion to tension the bone screw, respectively. FIG. 16A may depict the bone screw 1100 immediately after performance of the step 1350 of the method 1300 of FIG. 17, i.e., after the tension member 1108 has been inserted into and coupled to the proximal member 1104 and the distal member 1106, but before further torque has been applied to the bone screw 1100 to drive the distal member 1106 further into the second bone portion 162. FIG. 16B may depict the bone screw 1100 after performance of the step 1360 of the method 1300 of FIG. 17, after the bone screw 1100 has been elongated to its maximum length. Again, the interface 164 has been closed by the compression applied between the first bone portion 160 and the second bone portion 162 by the bone screw 1100 in its elongated form.

Notably, the bone screw 100 and the bone screw 1100 may not always be elongated to their maximum lengths. In some embodiments, it may be beneficial to stop applying torque to the bone screw 100 and/or the bone screw 1100 before maximum length has been reached.

FIG. 17 is a flowchart depicting a method 1300 of inserting a bone screw into bone along a guide wire, according to one embodiment. As shown, the method 1300 may commence with a step 1310 in which the guide wire is inserted into the two bone portions, such as the first bone portion 160 and the second bone portion 162 of FIGS. 6A and 6B, at the desired location for the bone screw. Then the method 1300 may proceed to a step 1320 in which a cannulated drill (for example, with a stepped diameter as mentioned above), is inserted over the guide wire and used to form the pilot hole at the desired location.

With the pilot hole formed, the method 1300 may proceed to a step 1330 in which the bone screw is inserted over the guide wire, without the tension member. The bone screw may partially or fully inserted into the bone at this stage, with the guide wire in place. The step 1330 may be similar to the step 310 of the method 300. Then, in a step 1340, the guide wire may be removed, leaving the variable-length cavity of the bone screw vacant.

In a step 1350, the tension member may be inserted into the variable-length cavity of the bone screw; and connected to the proximal and distal members of the bone screw to undergo tension as the screw elongates. Then, in a step 1360, further torque may be applied to the fully-assembled bone screw so that the bone screw elongates and places the tension member under tension, as in the step 320 of the method 300. Optionally, in a further step (not shown), further torque may be applied to the bone screw, as in the step 330 of the method 300.

Notably, in some alternative embodiments, an elongating bone screw may have a head designed to embed partially or fully in the proximal bone portion. In such embodiments, threading may be provided on the screw head. One such example will be shown and described in connection with FIG. 18.

Figure 18:
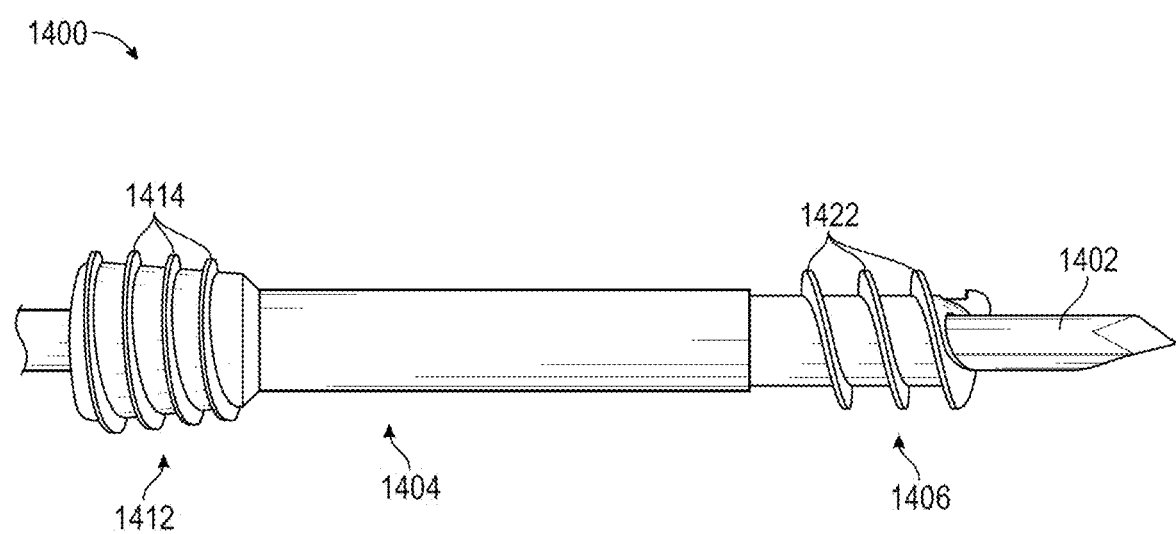
FIG. 18 is a side elevation view of a bone screw according to yet another embodiment.

FIG. 18 is a side elevation view of a bone screw 1400 according to another embodiment of the present disclosure. Like the bone screw 1100 of FIGS. 11A through 15, the bone screw 1400 may be insertable into the bone over a guide wire 1402. The bone screw 1400 may also have a proximal member 1404, a distal member 1406, and a tension member (not shown) that is functionally similar to the tension member 1108 of FIGS. 11A through 15.

The proximal member 1404 may have a head 1412 with a generally conical shape, tapered such that the head 1412 has a diameter that decreases along the distal direction. The head 1412 may have proximal threads 1414. The proximal threads 1414 may also have a tapered major diameter and a tapered minor diameter, and may have a pitch that is smaller than the pitch of bone-engaging threads 1422 of the distal member 1406.

Thus, as the proximal threads 1414 engage the proximal bone portion and the bone-engaging threads 1422 of the distal member 1406, the proximal member 1404 may advance more slowly than the distal member 1406. This differential in rates of advancement may cause the bone screw 1400 to elongate, even as the head 1412 is being embedded in the proximal bone portion.

Such an embodiment may help distribute compressive stress from the head 1412 over a larger volume of bone, and may also avoid leaving any portion of the head 1412 protruding proximally from the proximal bone. More precisely, if desired, the head 1412 may be fully embedded in the proximal bone portion. If desired, the differential pitch between the proximal threads 1414 and the bone-engaging threads 1422 may be selected such that the bone screw 1400 reaches maximum length as the proximal surface of the head 1412 becomes flush with the exterior cortex of the proximal bone portion.

Figure 33:
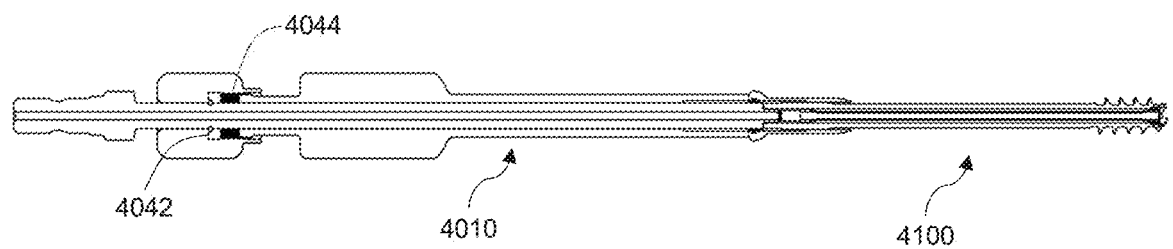
FIG. 33 is a side elevation, section view of the bone screw and the pre-stretch driver shown in FIG. 31.

In some embodiments, it may be desirable to use a variable-length bone screw with a portion of an exterior diameter similar in size to a minor diameter of distal bone engaging threads with the ability to be implantable over a guide wire, as will be set forth in the method 2500 of FIGS. 33. FIGS. 19A through 23 show a bone screw 2100 that is configured to facilitate use with a guide wire and that has a portion of an exterior diameter that is similar in size to a minor diameter of distal bone engaging threads.

The bone screw 2100 may have a longitudinal axis 2102, a proximal member 2104, a distal member 2106, a nut 2004, and a tension member 2108. As shown, the longitudinal axis 2102 of the bone screw 2100 may be an axis extending along the geometric center and/or axis of radial symmetry of the bone screw 2100, along the longest length of the bone screw 2100. The terms "proximal" and "distal" are generally used with reference to displacement along the longitudinal axis 2102, although they are sometimes used as adjectives to describe features of a proximal or distal member, such as the proximal member 2104 and the distal member 2106.

Figure 19A:
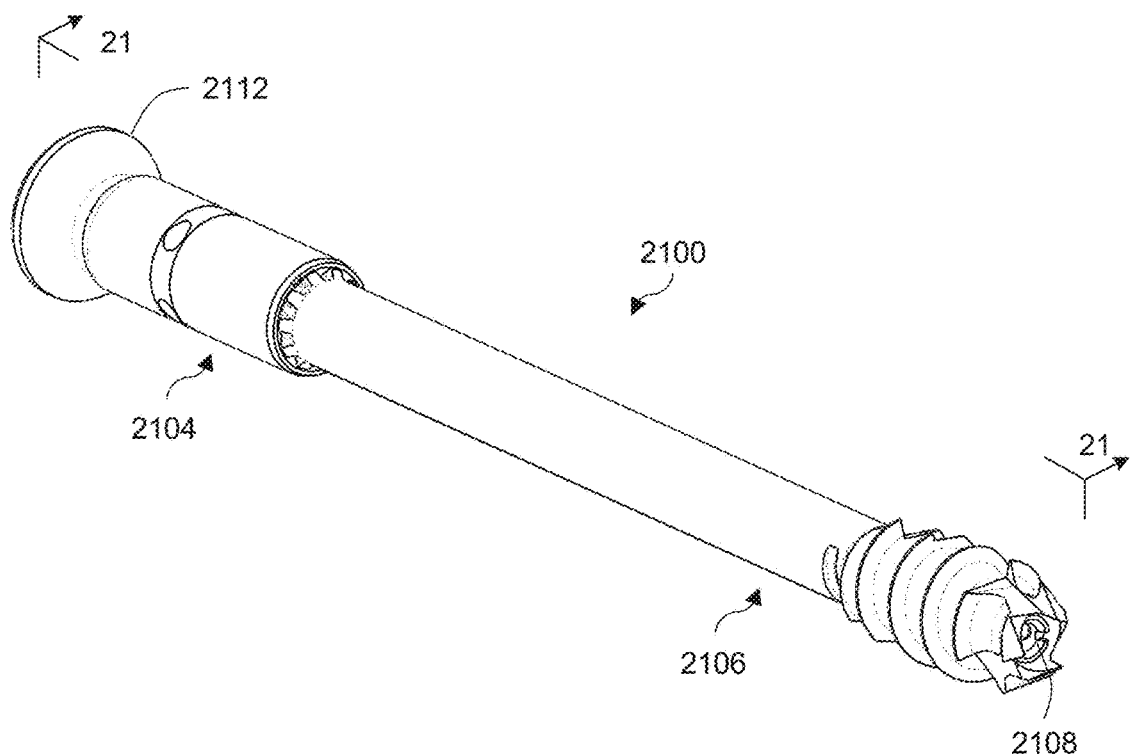
FIG. 19A is a perspective view of a bone screw according to one embodiment.
Figure 19B:
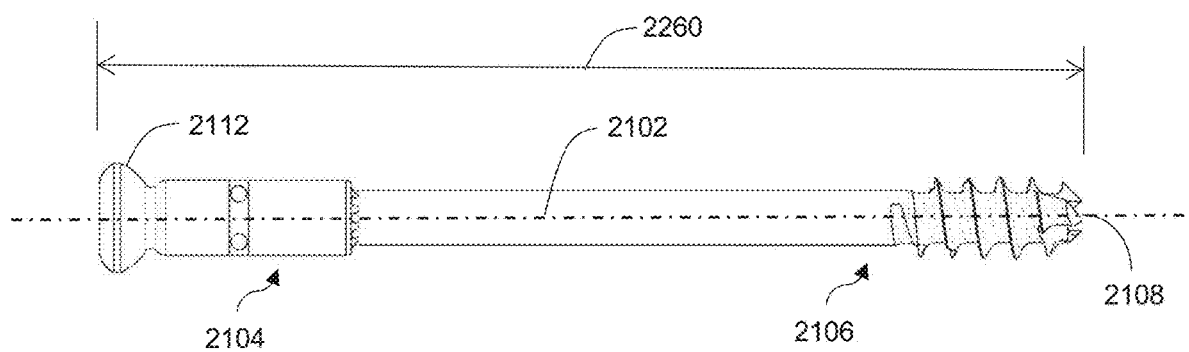
FIG. 19B is a side elevation view of the bone screw shown in FIG. 19A in a shortened state.
Figure 19C:
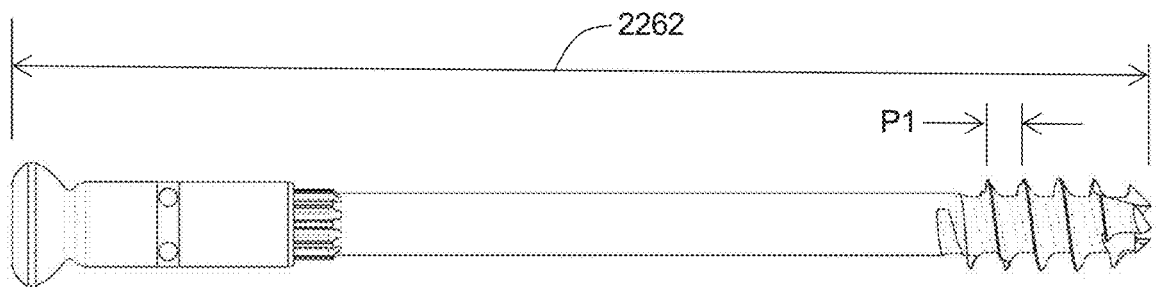
FIG. 19C is a side elevation view of the bone screw shown in FIG. 19A in a lengthened state.
Figure 20:
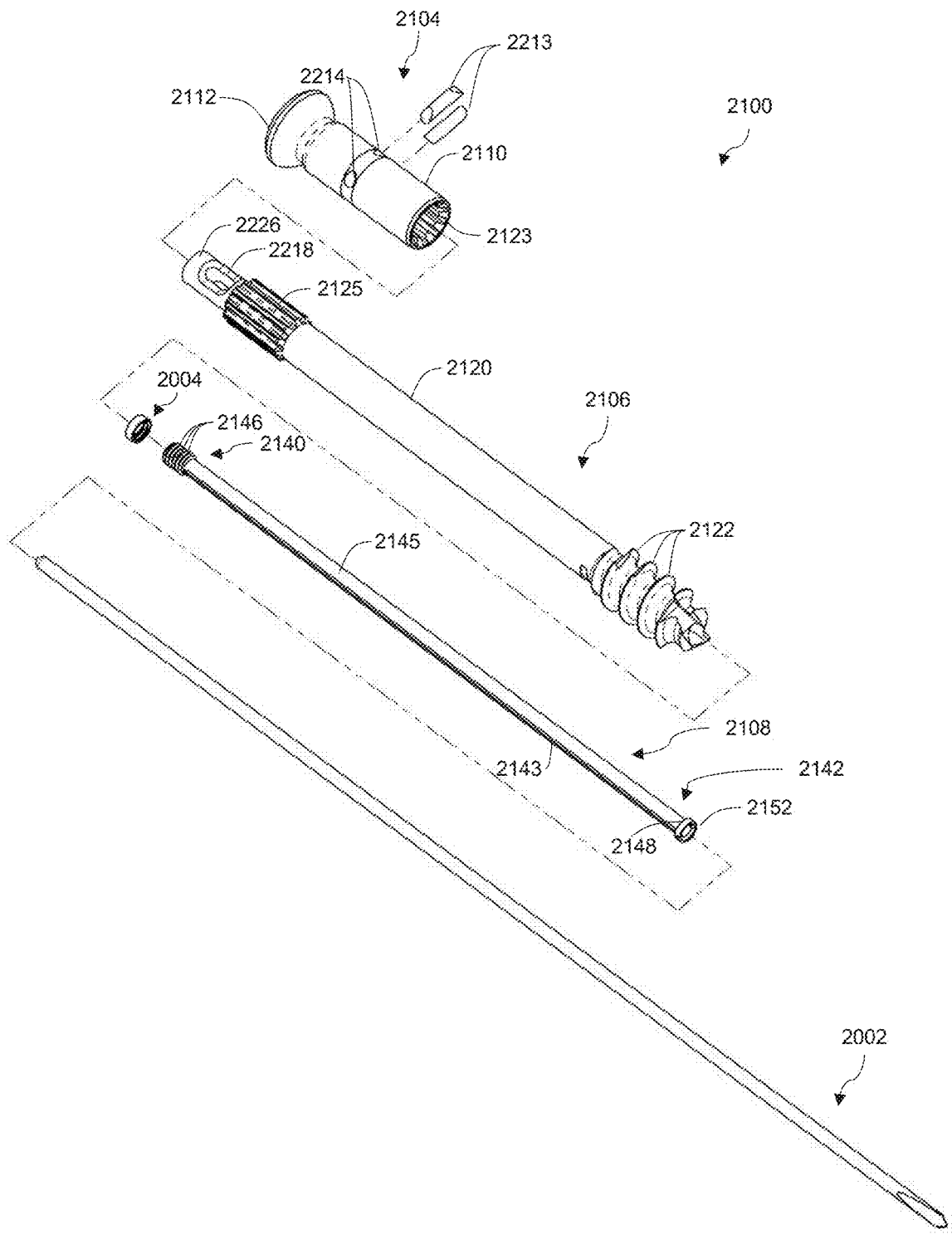
FIG. 20 is an exploded perspective view of the bone screw shown in FIG. 19A with a guidewire.
Figure 22:
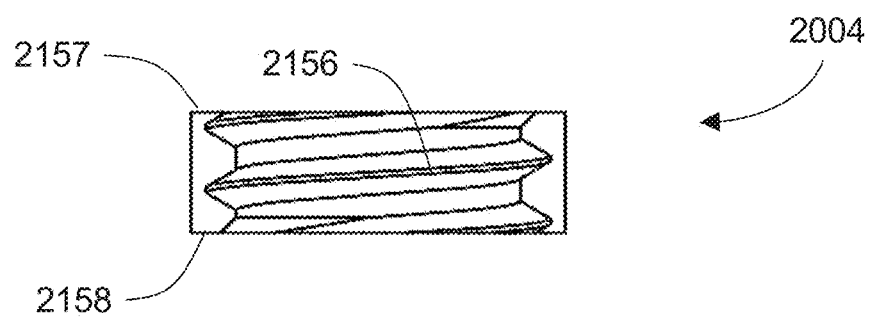
FIG. 22 is a side elevation, section view the nut shown in FIG. 20.
Figure 23:
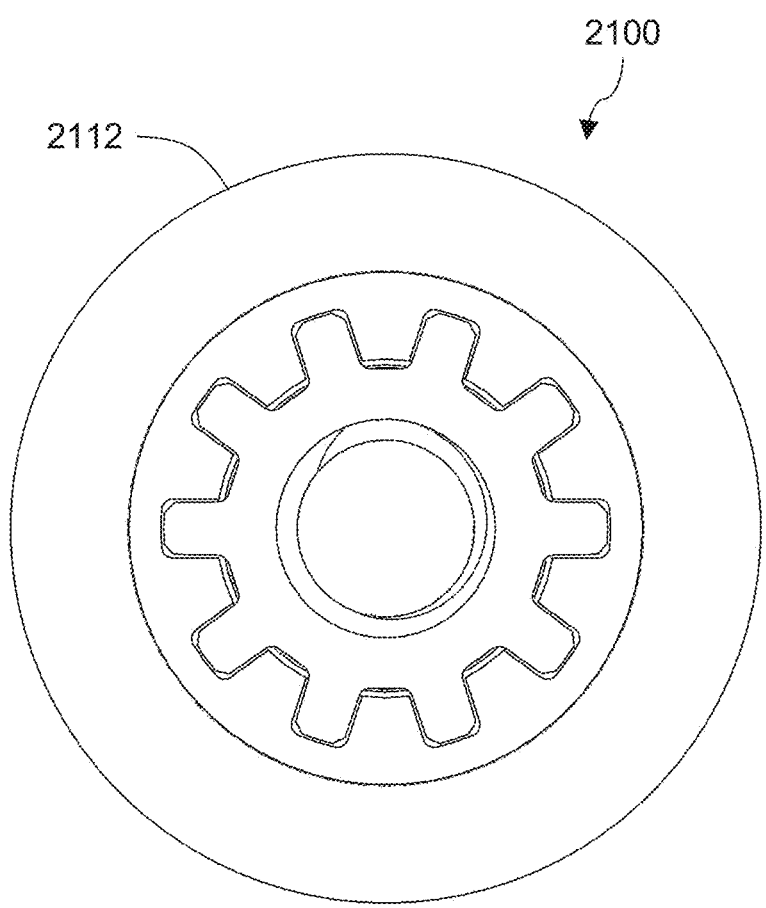
FIG. 23 is a front elevation, section view of the bone screw shown in FIG. 19A, taken along the section lines shown in FIG. 19B.

FIG. 19A is a perspective view of the bone screw 2100, according to one embodiment. FIG. 19B is a side elevation view of the bone screw 2100 shown in FIG. 19A in a shortened state. FIG. 19C is a side elevation view of the bone screw 2100 shown in FIG. 19A in a lengthened state. FIG. 20 is an exploded perspective view of the bone screw 2100 shown in FIG. 19A with a guidewire 2002. FIGS. 21A, 21B, 21C, and 21D are side elevation, section views of the bone screw, a proximal member, a distal member, and a tension member, respectively, of the bone screw 2100 shown in FIG. 19A. FIG. 22 is a side elevation, section view the nut 2004 shown in FIG. 20. FIG. 23 is a front elevation, section view of the bone screw 2100 shown in FIG. 19A, taken along the section lines shown in FIG. 19B.

Various parts of the bone screw 2100 may be identical or similar to their counterparts on the bone screw 100 and/or the bone screw 1100: the descriptions of components of the bone screw 100 and the bone screw 1100 are applicable to their counterparts in the bone screw 2100. All statements made regarding the bone screw 100 and/or the bone screw 1100 may be applied to the bone screw 2100, unless they would be contradicted by the differences between the bone screw 2100 and the bone screw 100 and/or the bone screw 1100.

The tension member 2108 may be coupled to the proximal member 2104 and the distal member 2106 and may be positioned in a variable-length cavity 2130 in a manner similar to that of coupling of the tension member 108 to the proximal member 104 and the distal member 106 of bone screw 100, and positioning of the tension member 108 in the variable-length cavity 130. The tension member 2108 may have a proximal end 2140, a distal end 2142, and a tube 2145 that connects the proximal end 2140 to the distal end 2142. The tube 2145 may define a cannulation 2141 extending from the proximal end 2140 to the distal end 2142. Tube 2145 may have a slot 2143, extending along the longitudinal axis 2102. Slot 2143 may be on one side of tube 2145: alternatively, multiple slots 2143 (not shown) may be on multiple sides of tube 2145, and may optionally be spaced apart in radially symmetrical fashion. Slot 2143 may have a width, and slot 2143 may extend along a partial or a full length of tube 2145. The number of slots 2143, the width and the length of each slot 2143, along with a wall thickness of tube 2145, may be selected to provide a predetermined cross-sectional area such that a predetermined amount of force (e.g., tension) may yield a desired change in length of tension member 2108 (i.e., providing a predetermined stiffness for the tension member 2108). The slot 2143 is optional and may be omitted if the tension member 2108 is to have a greater stiffness.

The proximal end 2140 of tension member 2108 may have proximal threads 2146 that facilitate coupling of the tension member 2108 to the proximal member 2104 via threaded engagement with interior threads 2147 within the proximal member 2104. The distal end 2142 of tension member 2108 may have a distal flange 2148 that facilitates coupling of the tension member 2108 to the nut 2004 via abutment of the distal flange 2148 on a distal surface 2157 of nut 2004. The nut 2004 may have a proximal surface 2158 that facilitates coupling of the nut 2004 to the distal member 2106 via abutment of the proximal surface 2158 on a corresponding surface 2149 of the distal member 2106. The nut 2004 may have interior threads 2156 that engage proximal threads 2146 to facilitate passing nut 2004 over the proximal end 2140 of the tension member 2108. In alternative embodiments (not shown), the interior threads 2156 may be omitted, leaving an interior surface (not shown) sized to slide over the proximal threads 2146 of the proximal member 2104. The distal end 2142 of the tension member 2108 may have a slot 2152 that facilitates rotation of the tension member 2108 with a driver such as a flat-head screwdriver to facilitate engagement of proximal thread 2146 of tension member 2108 and interior threads 2147 of proximal member 2104.

Alternatively, the nut 2004 and the tension member 2108 may be made as a unitary component (not shown). By making nut 2004 discrete from the tension member 2108, the tension member 2108 may be made from smaller diameter tubing material, which may decrease manufacturing cost. However, a nut 2004 and tension member 2108 may be assembled into bone screw 2100 in the same manner as shown in FIG. 20, and bone screw 2100 may otherwise function as described herein.

The proximal member 2104 may have a head 2112 at a proximal end of proximal member 2104, a proximal shank 2110 at a distal end of proximal member 2104, and a proximal interior surface 2114 that defines a proximal portion 2132 of variable-length cavity 2130. The proximal interior surface 2114 may include a proximal engagement surface 2222 that interacts with a distal engagement surface 2226 on distal member 2106 to share loads (in particular, bending loads) between proximal member 2104 and distal member 2106 in a similar fashion as described previously for proximal engagement surface 222 and distal engagement surface 226 of bone screw 100.

Proximal engagement surface 2222 and distal engagement surface 2226 may beneficially be displaced (for example, proximally) from torque transmission socket 2123 and torque transmission protrusion 2125. Torque transmission socket 2123 and torque transmission protrusion 2125 may act a fulcrum about which bending loads are applied between proximal member 2104 and distal member 2106. Thus, displacement of the proximal and distal load sharing features (for example, proximal engagement surface 2222 and distal engagement surface 2226) along longitudinal axis 2102 away from torque transmission socket 2123 and torque transmission protrusion 2125 may provide a longer moment arm to resist bending loads, and thereby resist undesired deformation of proximal member 2104 and/or distal member 2106.

Proximal member 2104 may have apertures 2214 that receive pins 2213 that extend transverse to longitudinal axis 2102. The pins 2213 may keep the proximal member 2104 and the distal member 2106 assembled and/or serve as motion stops for motion of the proximal end of the distal member 2106 within the proximal portion 2132 of the variable-length cavity 2130, as will be described subsequently. Optionally, the pins 2213 may be shaped such that they are flush with an exterior surface of proximal shank 2110. More particularly, the ends of the pins 2213 may be beveled, rounded, and/or otherwise shaped to provide sufficient surface area to secure the pins 2213 within the apertures 2214 without extending beyond the generally cylindrical exterior of the proximal shank 2110.

Distal member 2106 may have distal bone-engaging threads 2122 located on a distal end of distal member 2106, and may have a distal shank 2120 located proximal to distal bone-engaging threads 2122. Distal bone-engaging threads 2122 may have a major diameter 2244 and a minor diameter 2242. Advantageously, distal shank 2120 of distal member 2106 may have an exterior diameter 2252 that is similar in size to minor diameter 2242 to facilitate insertion of bone screw 2100 into bone. Distal member 2016 may have a distal interior surface 2124 that defines a distal portion 2134 of variable-length cavity 2130.

Like the bone screw 100, the bone screw 2100 may have a length limiting mechanism 2210 that controls the extent to which the bone screw 2100 can increase or decrease in length. Pins 2213 positioned in apertures 2214 on proximal member 2104 may interact with a proximal shoulder 2216, a distal shoulder 2217 and a relief 2218 located therebetween on distal member 2106 to form the length limiting mechanism 2210 in a similar fashion as described previously for length limiting mechanism 210.

Specifically, the length limiting mechanism 2210 may cause the bone screw 2100 to have a minimum length 2260 and a maximum length 2262 when the distal member 2106 has reached its minimum and maximum displacement along longitudinal axis 2102, respectively, relative to the proximal member 2104. The length limiting mechanism 2210 may include pins 2213 positioned in apertures 2214 of proximal member 2104, a distal shoulder 2217 of distal member 2106, and/or a proximal shoulder 2216 of distal member 2106. The pins 2213 may act as a stop feature, moving between the proximal shoulder 2216 and the distal shoulder 2217 to define the range of extension of the bone screw 2100.

Figures 21A, 21B, 21C, 21D:
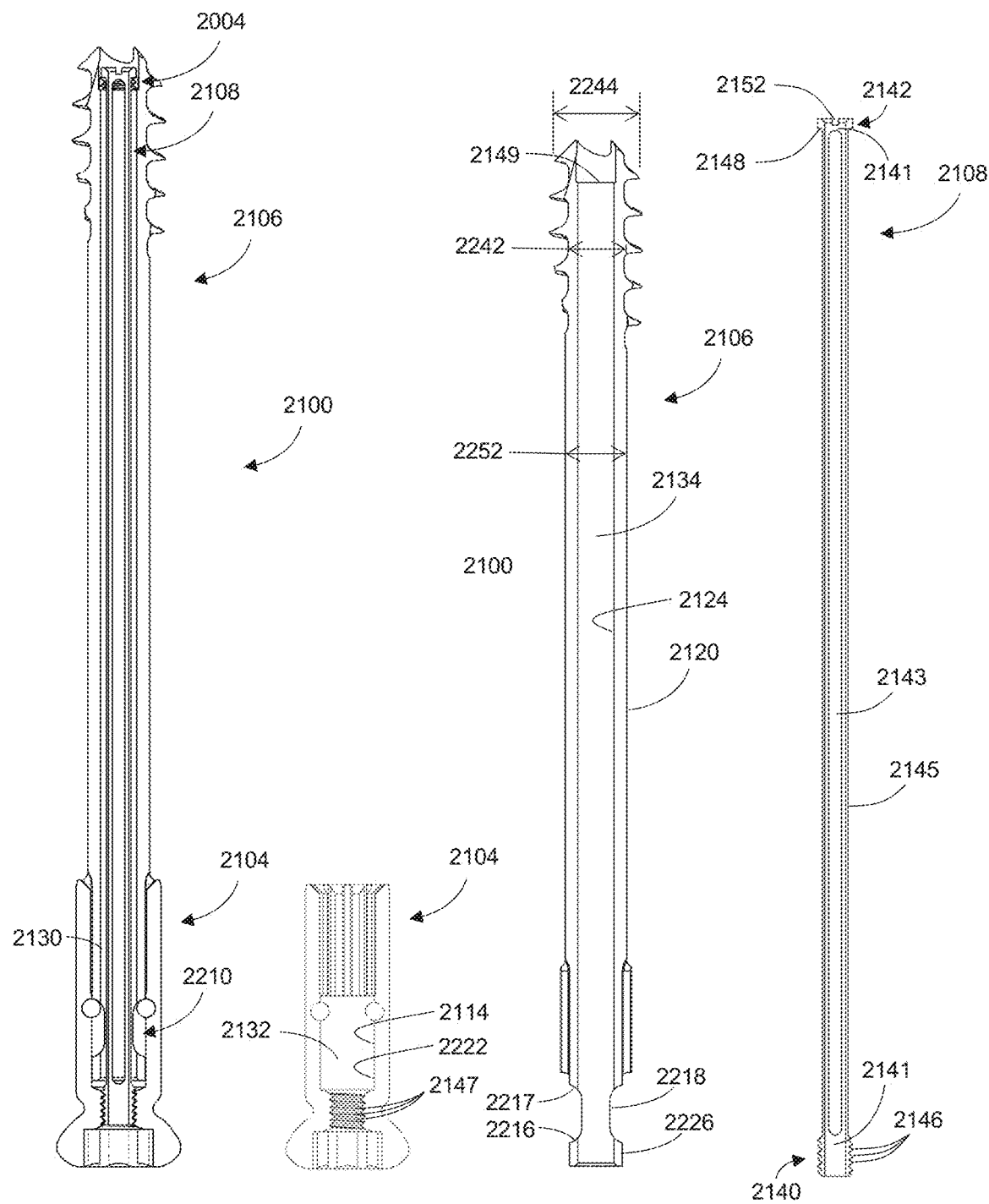
FIGS. 21A, 21B, 21C, and 21D are side elevation, section views of the bone screw, a proximal member, a distal member, and a tension member, respectively, of the bone screw shown in FIG. 19A.

Specifically, the minimum length 2260 may be caused by the abutment of pins 2213 against distal shoulder 2217 as shown in FIG. 21A. The maximum length 2262 may be caused by the abutment of pins 2213 against the proximal shoulder 2216. The minimum length 2260 and the maximum length 2262 may serve to provide a predetermined amount of minimum and maximum tension, respectively, in tension member 2108.

Beneficially, the minimum length 2260 and the maximum length 2262 may be determined with the same length limiting mechanism 2210, for example, as two opposing abutting surfaces (e.g. the distal shoulder 2217 and the proximal shoulder 2216) that define opposing ends the range of relative motion of a single intervening part (e.g., the pins 2213). Thus, the displacement between the current length of the bone screw 2100 and the minimum length 2260 or the maximum length 2262 may easily be referenced (for example, via fluoroscopic visualization) from the displacement between the pins 2213 and the distal shoulder 2217 and the proximal shoulder 2216, respectively.

Further, having both motion stops (for the minimum length 2260 and the maximum length 2262) be part of a single mechanism may facilitate variation in providing different bone screws 2100 with different length displacements (i.e., different displacements between the minimum length 2260 and the maximum length 2262). For example, distal engagement surface 2226 and/or proximal engagement surface 2222 may be shortened or lengthened to adjust the provide different length displacements.

Like the bone screw 100, the bone screw 2100 may have a torque transmission feature that facilitates the transmission of torque between proximal member 2104 and distal member 2016. The torque transmission feature may include a torque transmission socket 2123 on proximal member 2104 and a torque transmission protrusion 2125 on distal member 2106, such that the torque transmission protrusion 2125 may engage the torque transmission socket 2123 to transmit torque between the proximal member 2104 and the distal member 2106. Beneficially, the torque transmission socket 2123 and the torque transmission protrusion 2125 may include female and male spline shapes, respectively, that help to minimize hoop stresses incident to torque transmission, in a manner similar to that of embodiments described previously.

The torque transmission protrusion 2125 may advantageously have a torque transmission feature (e.g., the spline shapes mentioned above or other shapes designed to receive torque) with a larger diameter than the distal shank 2120 of the distal member 2106. In other words, the torque transmission feature may exist as a positive feature extending beyond the envelope of the distal shank 2120, rather than existing as a reduced cross-sectional size relative to the distal shank 2120. This may help the torque transmission protrusion 2125 and/or the torque transmission socket 2123 have sufficient mechanical strength to withstand the torsional, tensile, and/or bending loads that may be applied across the interface between the proximal member 2104 and the distal member 2106 during insertion in the bone and/or subsequent operation of the bone screw 2100 within the patient's body.

Various head configurations may be used for the bone screw 2100, or indeed for any of the bone screws in the present disclosure. Some examples will be shown and described in connection with FIGS. 24A, 24B, and 24C.

Figure 24A:
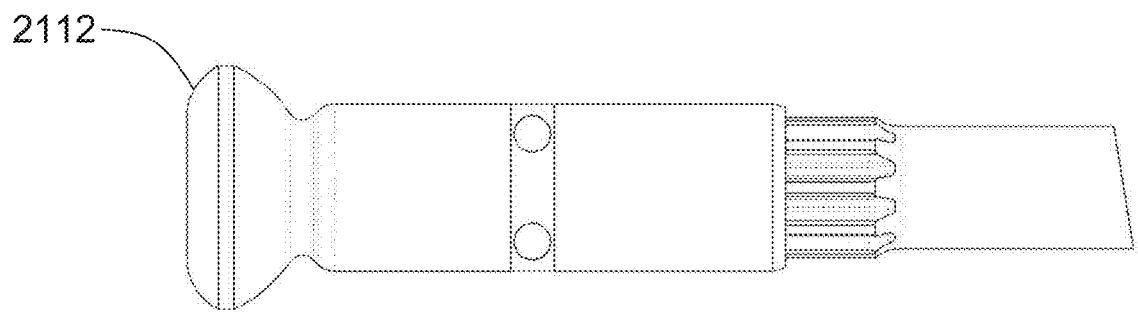
FIG. 24A is a side elevation view of a head of a bone screw according to one embodiment.
Figure 24B:
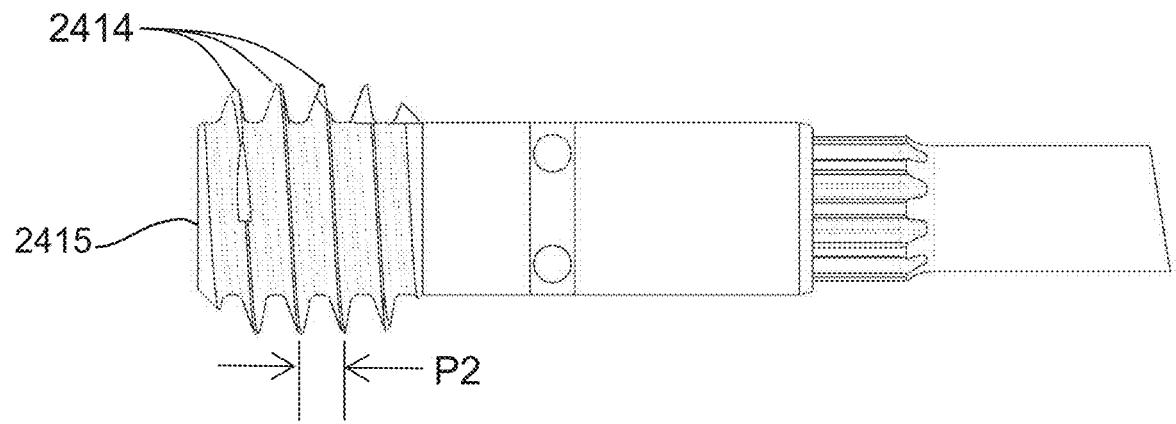
FIG. 24B is a side elevation view of a head of a bone screw according to another embodiment.
Figure 24C:
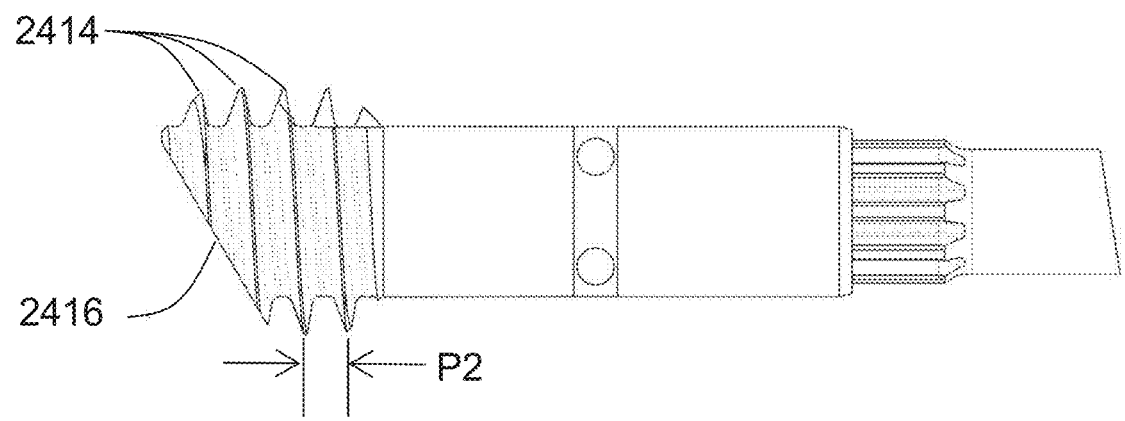
FIG. 24C is a side elevation view of a head of a bone screw according to yet another embodiment.

FIG. 24A is a side elevation view of a head of a bone screw according to one embodiment. FIG. 24B is a side elevation view of a head of a bone screw according to another embodiment. FIG. 24C is a side elevation view of a head of a bone screw according to yet another embodiment.

The variable length bone screw (for example, the bone screw 2100 or any other bone screw disclosed herein) may have a rounded head, such as head 2112 of FIG. 24A, adapted to contact a bone surface. The head 2112 may be configured to reside on the exterior of the bone. The rounded shape shown in FIG. 24A may help avoid damage to surrounding soft tissues. In alternative embodiments, an exterior head may have any shape known in the art, including but not limited to domed shapes. In some embodiments, a head may be shaped to reside in a countersink, counterbore, or other enlargement (not shown) formed in the hole that is to receive the bone screw 2100.

Alternatively, the bone screw 2100 (or any other bone screw disclosed herein) may have a threaded head a shown in FIG. 24B, with proximal bone-engaging threads 2414, adapted to engage a bone so that a proximal surface 2415 of the threaded head may not protrude beyond the surface of the bone in which it is embedded. In some embodiments, the proximal surface 2415 may be flush with the bone surface. In others, it may be recessed within the bone.

Furthermore in yet other alternative embodiments, the threaded head of any bone screw disclosed herein may have bevel 2416 on a proximal end of the threaded head (i.e., a proximal-most surface), as shown in FIG. 24C. The bevel 2416 may facilitate insertion of the bone screw 2100 at an angle that is nonperpendicular to the surface of the bone. In some embodiments, upon full insertion of the bone screw 2100 into bone at an oblique angle to a bone surface, the bevel 2416 may cause the proximal end of the threaded head to be parallel to, and flush with, the bone surface. Once the bone screw 2100 has been inserted to the desired depth, the surgeon may further rotate (or back out) the bone screw 2100 until the bevel 2416 has reached an orientation that is generally coplanar with the surrounding bone.

Distal bone-engaging threads 2122 may have a first pitch P1, or a thread crest-to-thread crest distance, as shown in FIG. 19A. Proximal bone-engaging threads 2414 may have a second pitch P2 as shown in FIGS. 24B and 24C. First pitch P1 and second pitch P2 may be selected to that as the bone screw 2100 is fully inserted into bone, the bone screw 2100 is stretched from a minimum length to a length greater than the minimum length. For example, first pitch P1 may be 3 mm, and second pitch P2 may be 2 mm. Upon the proximal bone-engaging threads engaging a proximal portion of a bore within the bone, a full revolution of the bone screw 2100 may result in a 1 mm increase in length of the bone screw 2100, since the distal member 2106 will advance 1 more millimeter than proximal member 2104. As an example, proximal bone-engaging threads 2414 may have five full threads, and distal bone-engaging threads 2122 may have five or more full threads. Thus, after five full revolutions that result in all five of the proximal threads being fully engaged in a bone, the bone screw 2100 may increase in length by 5 mm. If desired, the bone screw 2100 may be designed such that length increase brings the bone screw 2100 to its maximum length 2262. In alternative embodiments, the increase in length that occurs with full insertion of the bone screw 2100 may be less (for example, 25%, 50%, or 75%) of the maximum elongation permitted by the bone screw 2100.

The values of first pitch P1 and second pitch P2, along with the number of proximal bone-engaging threads 2414, may be selected to provide a predetermined amount of lengthening of the bone screw 2100 upon full insertion into a bone. In some embodiments, the number of proximal bone-engaging threads 2414 may be between 3 and 6, inclusive. More precisely, in some embodiments, the number of proximal bone-engaging threads 2414 may be 4, 5, or a number between 4 and 5 (for example, resulting from a residual thread that only extends partway around the longitudinal axis of the bone screw 2100).

In some embodiments, the difference between the values of first pitch P1 and second pitch P2 may be between 0.25 mm and 1.25 mm, inclusive. Further, in some embodiments, the difference in pitch may be between 0.5 mm and 1.0 mm, inclusive.

In one embodiment, a 3.5 mm diameter by 50 mm minimum length bone screw 2100 may have a first pitch P1 of 1.3 mm, a second pitch P2 of 0.8 mm, and 5 proximal bone-engaging threads 2414, resulting in 2.5 mm of potential length increase during implantation. In another embodiment, a 7.5 mm diameter by 100 mm minimum length bone screw 2100 may have a first pitch P1 of 3 mm, a second pitch P2 of 2 mm, and have 5 proximal bone-engaging threads 2414, resulting in 5 mm of potential length increase.

In some embodiments, it may be desirable to use a variable-length bone screw with a proximal drive feature on a distal member containing distal bone-engaging threads and that can work in conjunction with a guide wire, as set forth in the method 2500 of FIG. 33. FIGS. 25A through 30 show a bone screw 3100 that is configured to facilitate use with a guidewire 3002 and that has a proximal drive feature on a distal member containing distal bone-engaging threads. The bone screw 3100 may have a longitudinal axis 3102, a proximal member 3104, a distal member 3106, a tension member 3108, a nut 3004, a support ring 3006, and a retaining ring 3008.

Figure 25A:
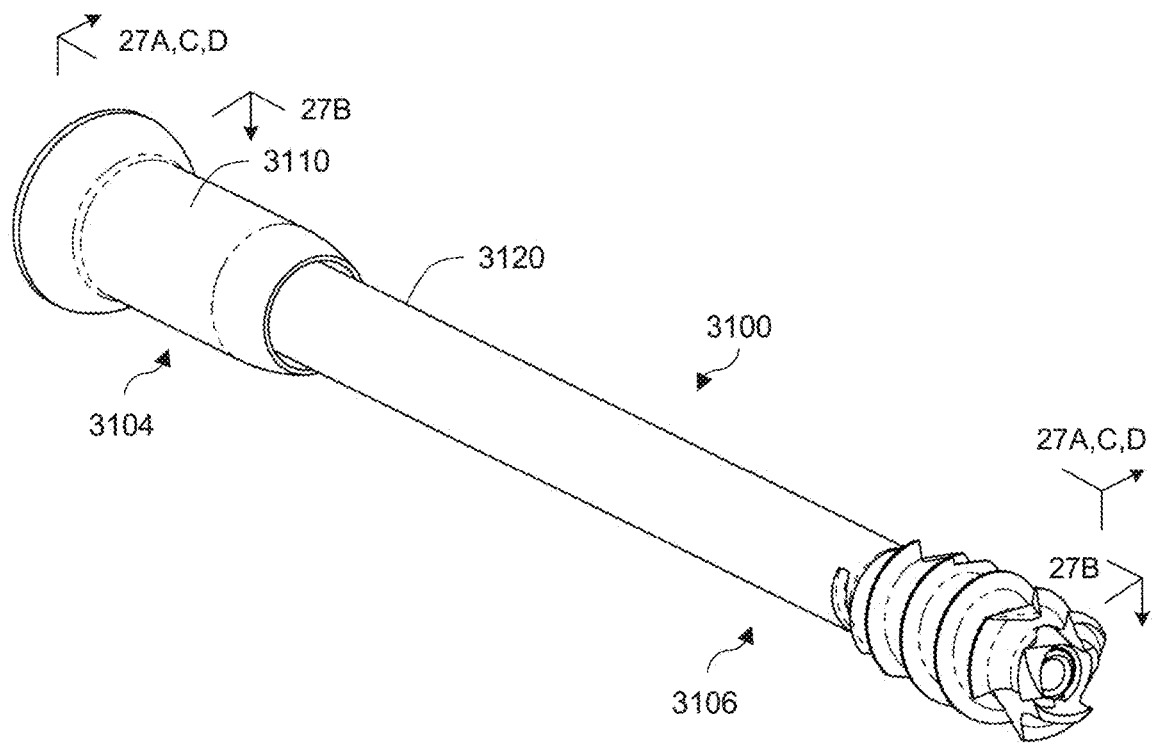
FIG. 25A is a perspective view of a bone screw according to one embodiment.
Figure 25B:
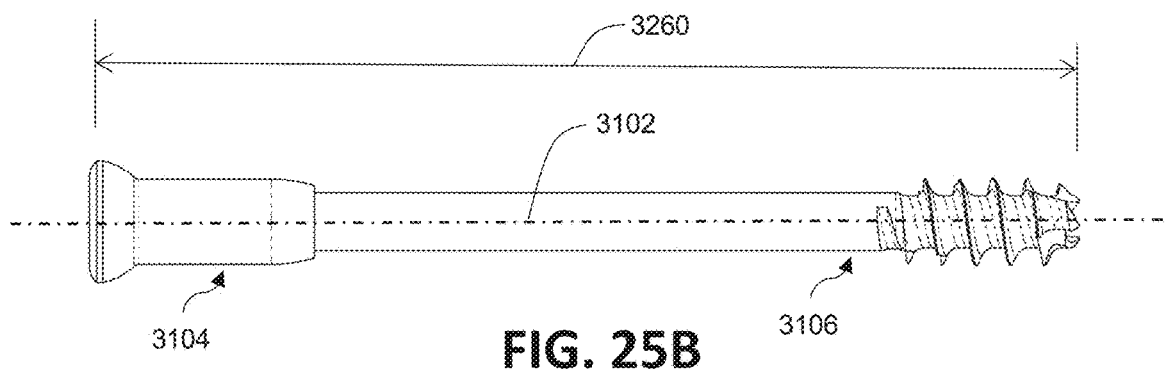
FIG. 25B is a side elevation view of the bone screw shown in FIG. 25A in a shortened state.
Figure 25C:
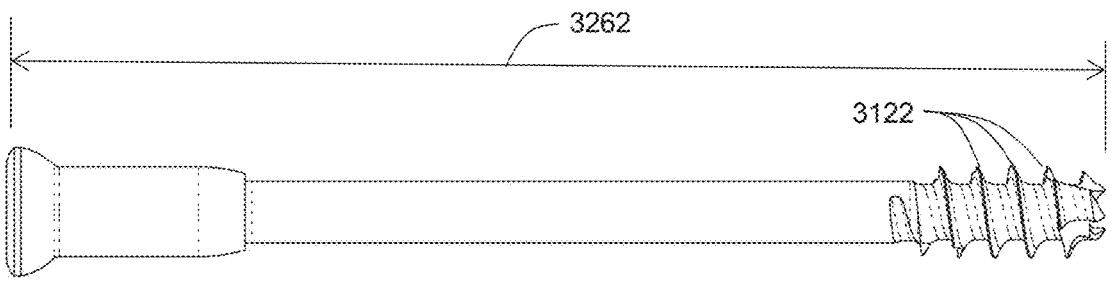
FIG. 25C is a side elevation view of the bone screw shown in FIG. 25A in a lengthened state.
Figure 26:
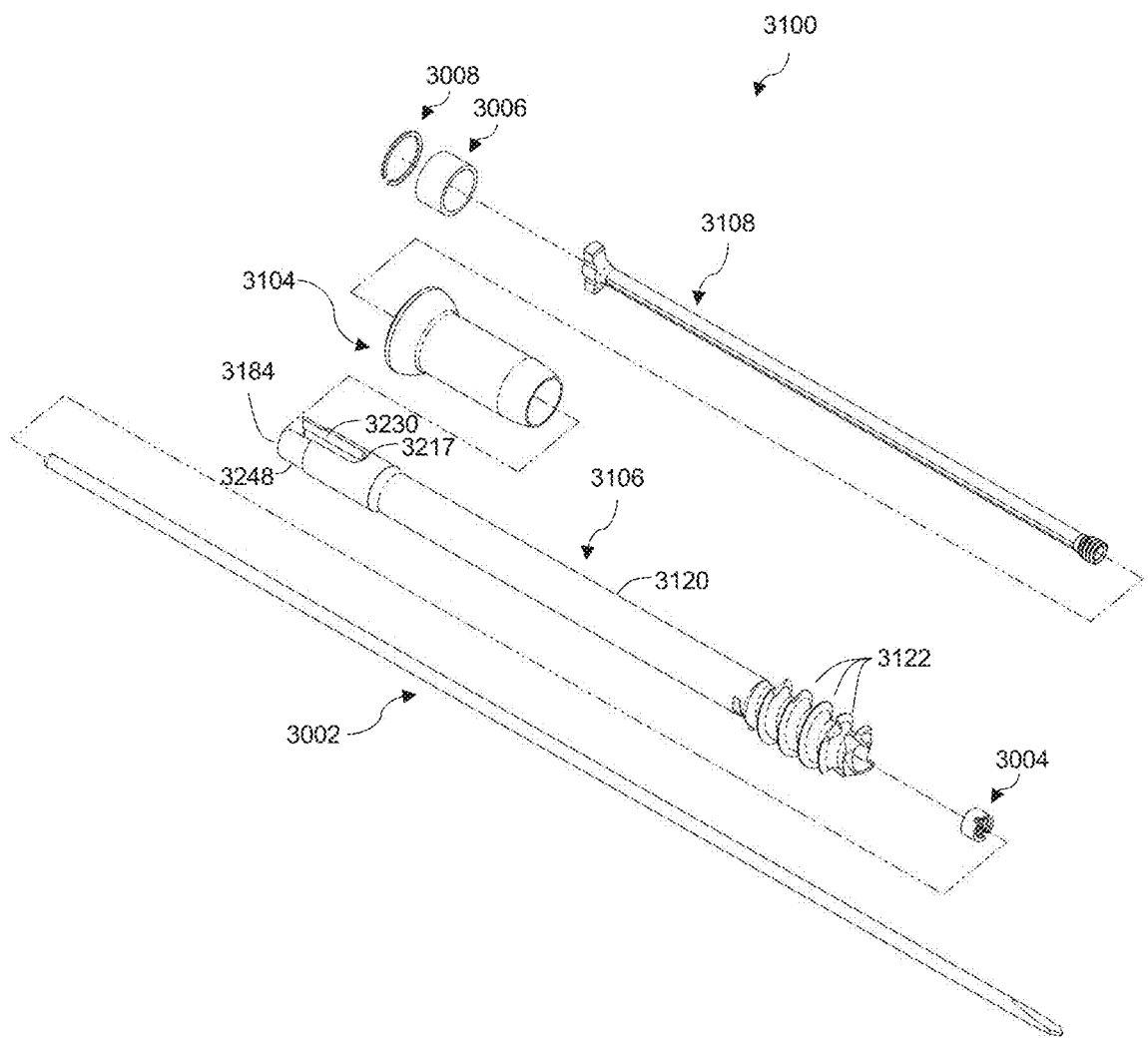
FIG. 26 is an exploded perspective view of the bone screw shown in FIG. 25A with a guidewire.
Figures 27A, 27B, 27C, 27D:
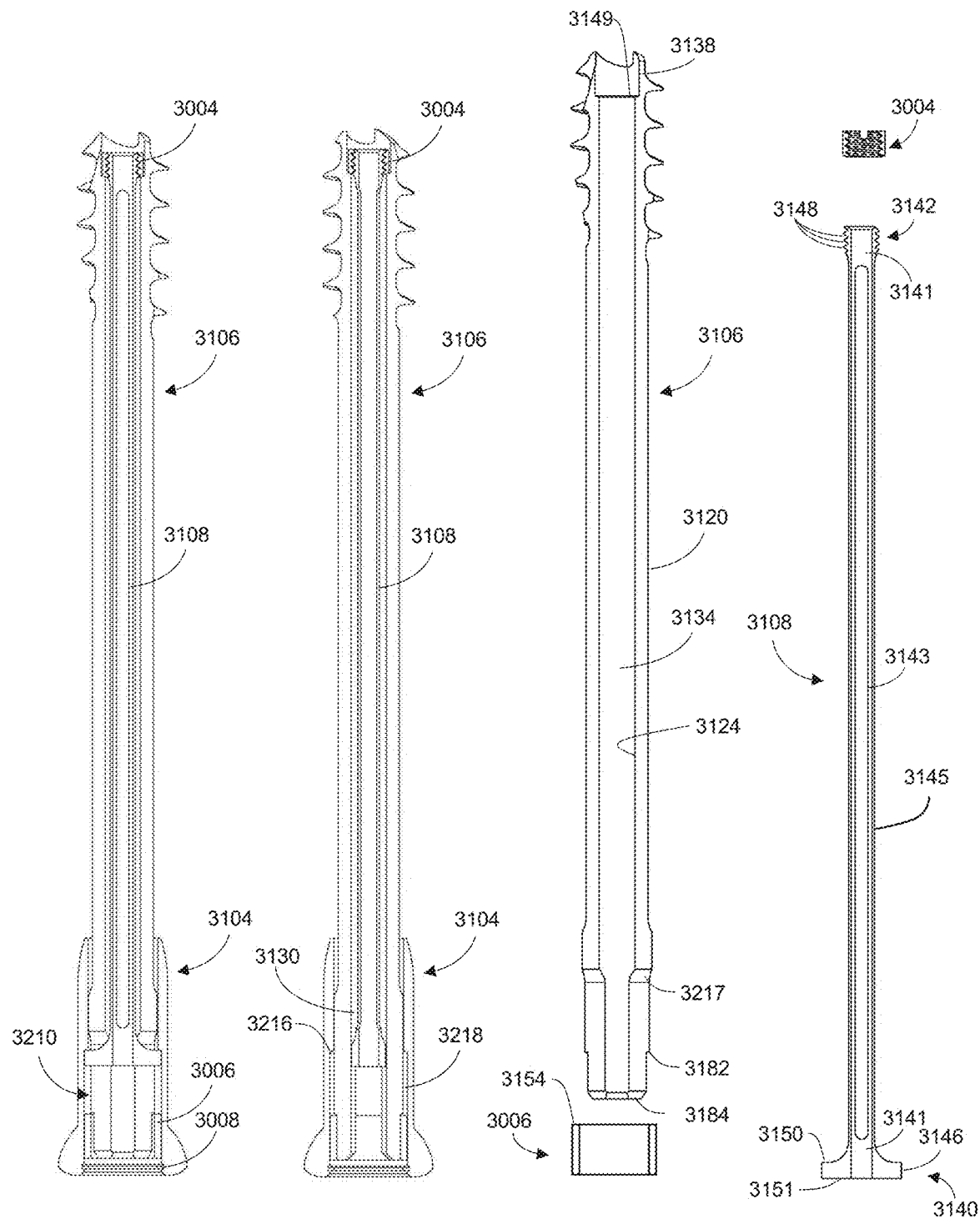
FIGS. 27A, 27B, 27C, and 27D are side elevation, section views of the bone screw in a first plane, the bone screw in a second plane orthogonal to the first plane, a support ring and a distal member, and a tension member and a nut, respectively, of FIG. 25A.
Figure 28:
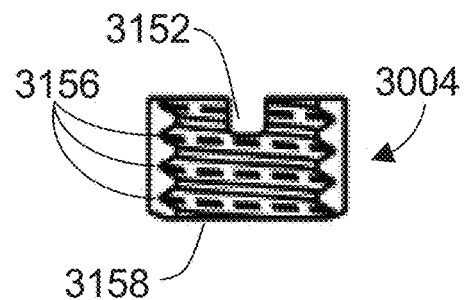
FIG. 28 is a side elevation, section view of the nut shown in FIG. 26.
Figure 29:
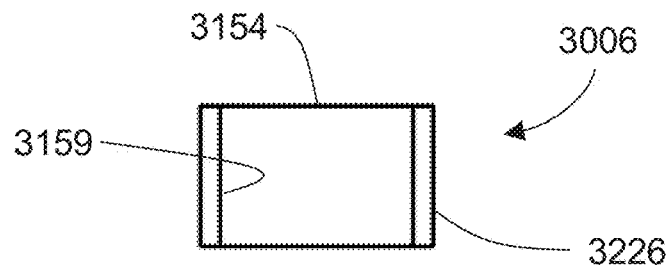
FIG. 29 is a side elevation, section view of the support ring shown in FIG. 26.
Figure 30:
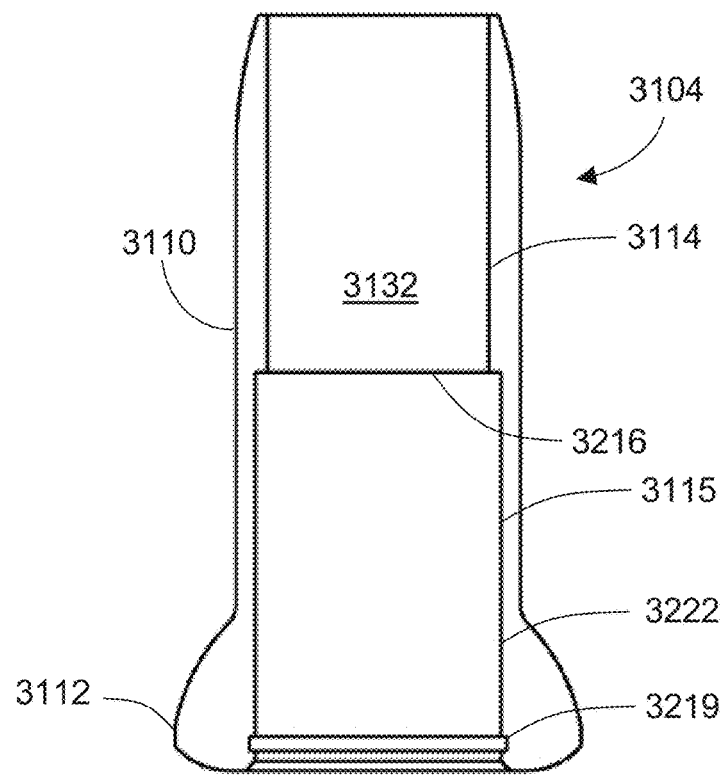
FIG. 30 is a side elevation, section view of the proximal member shown in FIG. 26.

FIG. 25A is a perspective view of bone screw 3100 according to one embodiment. FIG. 25B is a side elevation view of the bone screw 3100 shown in FIG. 25A in a shortened state. FIG. 25C is a side elevation view of the bone screw 3100 shown in FIG. 25A in a lengthened state. FIG. 26 is an exploded perspective view of the bone screw 3100 shown in FIG. 25A with a guidewire 3002. FIGS. 27A, 27B, 27C, and 27D are side elevation, section views of the bone screw 3100 in a first plane (FIGS. 27A, 27C, and 27D), the bone screw 3100 in a second plane orthogonal to the first plane (FIG. 27B), a support ring 3006, a distal member 3106, a tension member 3108, and a nut 3004. FIGS. 28, 29, and 30 are side elevations, section views of the nut 3004, the support ring 3006, and proximal member 3104, respectively, shown in FIG. 26.

Various parts of the bone screw 3100 may be identical or similar to their counterparts on the bone screw 2100 and/or other bone screw embodiments presented herein: these parts may not be described again here. All statements made regarding the bone screw 2100 apply to the bone screw 3100 unless they would be contradicted by the differences between the two.

The bone screw 3100 may be configured to allow the proximal member 3104 to be assembled over the proximal end of the distal member 3106. Then, tension member 3108 may be inserted through the proximal member 3104, into the distal member 3106, and into the nut 3004. The support ring 3006 may then be attached to the proximal end of the distal member 3106, and a retaining ring 3008 may then be inserted into an internal groove 3219 in proximal member 3104 to form an assembly that is inserted into the bone over guidewire 3002.

The assembled bone screw 3100, also referred to as bone screw 3100, may have interior threads 3156 of nut 3004 engaged with distal threads 3148 of tension member 3108. The nut 3004 may have a slot 3152 that serves as a drive feature by engaging a driver, such as a flat blade screwdriver (not shown), to facilitate engagement of interior threads 3156 with distal threads 3148.

The support ring 3006 may have an inner surface 3159 that is a coupled to a proximal exterior surface 3248 of distal member 3106 by a coupling mechanism known in the art such as threading, retention with a retaining ring, crimping, swaging, pinning, press fitting, adhesive or chemical bonding, soldering, brazing, welding, or combinations thereof. The support ring 3006 may be positioned on the distal member 3106 such that a distal surface 3154 of support ring 3006 abuts the shoulder 3182 on distal member 3106, and a distal engagement surface 3226 of support ring 3006 is generally fitted around the proximal end of distal member 3106, extending between the proximal surface 3184 of distal member 3106 and the shoulder 3182.

The tension member 3108 may be coupled to the proximal member 3104 and the distal member 3106 and may be positioned in a variable-length cavity 3130 similar to the way that tension member 108 is coupled to the proximal member 104 and the distal member 106 of bone screw 100 and positioned in variable-length cavity 130. The tension member 3108 may have a proximal end 3140, a distal end 3142, and a tube 3145 that connects the proximal end 3140 to the distal end 3142, and a cannulation 3141 that extends from the proximal end 3140 to the distal end 3142. Tube 3145 may have a slot 3143, extending along the longitudinal axis 3102. Slot 3143 and tube 3145 may have the same features and operation as previously described for slot 2143 and tube 2145.

The proximal end 3140 of tension member 3108 may have a head 3146 that facilitates coupling of the tension member 3108 to the proximal member 3104 via abutment of a distal surface 3150 of head 3146 with a shoulder 3216 inside proximal member 3104. The distal end 3142 of tension member 3108 may have distal threads 3148 that engage interior threads 3156 of nut 3004. The nut 3004 may have a proximal surface 3158 that facilitates coupling of the nut 3004 to the distal member 3106 via abutment of the proximal surface 3158 on a corresponding surface 3149 of the distal member 3106. The surface 3149 may reside in a distal socket 3138 at the distal end of the distal member 3106. The distal socket 3138 may be sized to receive and contain part or all of the nut 3004.

The proximal member 3104 may have a head 3112 at a proximal end of proximal member 3104, a proximal shank 3110 at a distal end of proximal member 3104, a proximal interior surface 3114, and an interior surface 3115 adjacent to and proximal to proximal interior surface 3114. Together, proximal interior surface 3114 and interior surface 3115 may define a proximal portion 3132 of variable-length cavity 3130. The interior surface 3115 may include a proximal engagement surface 3222 that interacts with a distal engagement surface 3226 on support ring 3006 in a similar fashion as described previously for proximal engagement surface 222 and distal engagement surface 226 of bone screw 100, defining a bending transmission feature or load sharing feature similar in function to those described in connection with previous embodiments.

Distal member 3106 may have distal bone-engaging threads 3122 located on a distal end of distal member 3106 and may have a distal shank 3120 located proximal to distal bone-engaging threads 3122. Distal member 3106 may have a distal interior surface 3124 that defines a distal portion 3134 of variable-length cavity 3130.

A driver engagement feature 3230 may be advantageously located on a proximal end of distal member 3106 so that bone screw 3100 may be driven by a driver, such as a flat blade screwdriver (not shown), that engages driver engagement feature 3230 so that torque is transmitted directly to the distal bone-engaging threads 3122 via the distal shank 3120. Thus, torque may be transmitted directly through a monolithic structure to provide the most efficient method (i.e., lowest input torque) for inserting distal bone-engaging threads 3122 into bone and causing the bone screw 3100 to lengthen from a minimum length 3260 to a maximum length 3262, when compared to transmitting torque through a torque transmission mechanism, such as a torque transmission protrusion 2125 engaged in a torque transmission socket 2123, where additional input torque is required to overcome frictional forces aligned with the longitudinal axis 2102 therebetween.

Further to the foregoing, in known elongating bone screws, a torque transmission feature may be the source of significant resistance to screw elongation, as the torque imparted to the bone screw may induce significant friction (and thence, resistance to the relative sliding motion needed for elongation) between the proximal and distal members. Thus, it may be a benefit to have the driver engagement feature 3230 present on distal member 3106. This placement of driver engagement feature 3230 may enable proximal member 3104 to be rotatably and slidably coupled to distal member 3106. Permitting relative rotation between proximal member 3104 and distal member 3106 may facilitate assembly and/or facilitate implantation of bone screw 3100, particularly in embodiments in which the proximal member 3104 has bone-engaging threads like those of FIGS. 24A and/or 24B. In such embodiments, if desired, proximal member 3104 may have its own driver engagement feature (not shown) so that proximal member 3104 can be rotated into engagement with the bone independently of rotation of distal member 3106 to engage bone with the distal bone-engaging threads 3122.

Driver engagement feature 3230 is shown in FIG. 26 in the form of a slot, but any other shape for transmitting torque between a driver and a socket may be used as known in the art. For example, a cruciate shape, a square shape, polygonal shape, a hexalobular shape, and/or the like may be used. It may be beneficial to retain side openings like those of the driver engagement feature 3230 in the drive socket to allow head 3146 of tension member 3108 to extend outwardly to engage abutment features of the proximal member 3104, as described previously.

Like the bone screw 100, the bone screw 3100 may have a length limiting mechanism 3210 that controls the extent to which the bone screw 3100 can increase or decrease in length. Distal surface 3150 and a proximal surface 3151 of head 3146 of tension member 3108 may interact with a shoulder 3216 of proximal member 3104 and/or a distal shoulder 3217 of driver engagement feature 3230, and a distal surface 3154 of support ring 3006, respectively, to form a length limiting mechanism 3210 similar in function to the length limiting mechanism 210 described previously.

Specifically, the length limiting mechanism 3210 may cause the bone screw 3100 to have a minimum length 3260 and a maximum length 3262 when the distal member 3106 has reached its minimum and maximum displacement along longitudinal axis 3102, respectively, relative to the proximal member 3104. The minimum length 3260 may be caused by the abutment of distal surface 3150 of head 3146 against shoulder 3216 of proximal member 3104 and/or distal shoulder 3217 of driver engagement feature 3230. The maximum length 2262 may be caused by the abutment of proximal surface 3151 of head 3146 of tension member 3108 against distal surface 3154 of support ring 3006. A relief 3218 defined by the interior surface 3115 of proximal member 3104, located between the shoulder 3216 of proximal member 3104 and the distal surface 3154 of support ring 3006, may provide space for the head 3146 of tension member 3108 to move from a maximal spacing away from distal surface 3154 when bone screw 3100 is at minimum length 3260 to making contact with distal surface 3154 when bone screw 3100 is at maximum length 3262.

Advantageously, during the insertion of bone screw 3100 into a bone, the amount of remaining lengthening (e.g., the distance between the current length and the maximum length) may be directly visualized by radiograph when bone screw 3100 is comprised of components made of metal. The remaining length may be determined by observing the distance between 1) the proximal surface 3151 of head 3146 of tension member 3108, and 2) distal surface 3154 of support ring 3006 connected to distal member 3106. Additionally or alternatively, the amount of stretch may be determined by using a screwdriver (not shown) that has axially sliding first and second contact surfaces that contain features such as markings or grooves that register against the proximal end of the proximal member and the proximal end of the distal member, respectively. In either case, etchings and/or other radiographic markings may be applied to proximal member 3104 and/or distal member 3106 to help measure the length of the bone screw 3100 radiographically during insertion.

As another advantage, the distal shank 3120 of the distal member 3106 may have a constant cross-sectional shape from the distal-most end of the proximal member 3104 to the proximal end of the distal bone-engaging threads 3122 of the distal member 3106. This may provide smoother insertion of the bone screw 3100 into the bone, as the distal shank 3120 may lack any feature that would snag on the bone. The bone screw 3100 may lengthen during the insertion process as in previous embodiments, and the constant cross-sectional shape of the distal shank 3120 may help avoid resistance to expansion. Further, the constant cross-sectional shape of the distal shank 3120 may help avoid trapping bone encircling the distal shank 3120 as the bone screw 3100 shortens during bone compression incident to the healing process.

The minimum length 3260 and the maximum length 3262 may serve to provide a predetermined amount of minimum and maximum tension, respectively, in tension member 3108. For example, the minimum length 3260 may be selected so that the corresponding strain in tension member 3108 corresponds to point A in diagram 2700, and the maximum length may be selected so that the corresponding strain in tension member 3108 corresponds to point C or point C' in diagram 2700, as will be described subsequently.

Tension member 3108 may be pre-stretched, thereby inducing pre-strain, during assembly of nut 3004 to tension member 3108 when tension member 3108 is positioned in the variable-length cavity 3130 by further tightening nut 3004 after distal surface 3150 of head 3146 engages shoulder 3216 of proximal member 3104 (or alternatively, after distal surface 3150 of head 3146 engages distal shoulder 3217 of driver engagement feature 3230). The amount of pre-strain may be selected to correspond to point A shown in diagram 2700. Alternatively or additionally, tension member 3108 may be pre-stretched, thereby inducing pre-strain, by thermal processing, as described below.

In some embodiments, it may be desirable to releasably pre-stretch a variable-length bone screw, such as the bone screw 3100 or any of the other bone screw embodiments disclosed herein, prior to insertion into a first bone portion and a second bone portion. Then, the variable-length bone screw may be inserted into the bone portions, and then the pre-stretch may be released so that the variable-length bone screw imparts compression between the bone portions without the need for elongation of the bone screw during insertion of the bone screw into the bone. An embodiment of pre-stretch and release of a variable-length bone screw is provided in FIG. 31 through FIG. 36.

Figure 31:
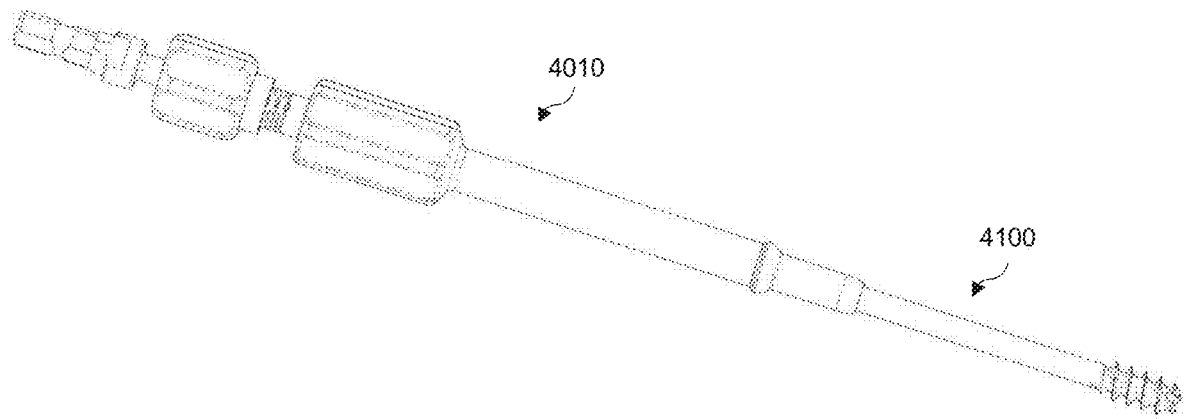
FIG. 31 is a perspective view of a bone screw and a pre-stretch driver according to one embodiment.
Figure 32:
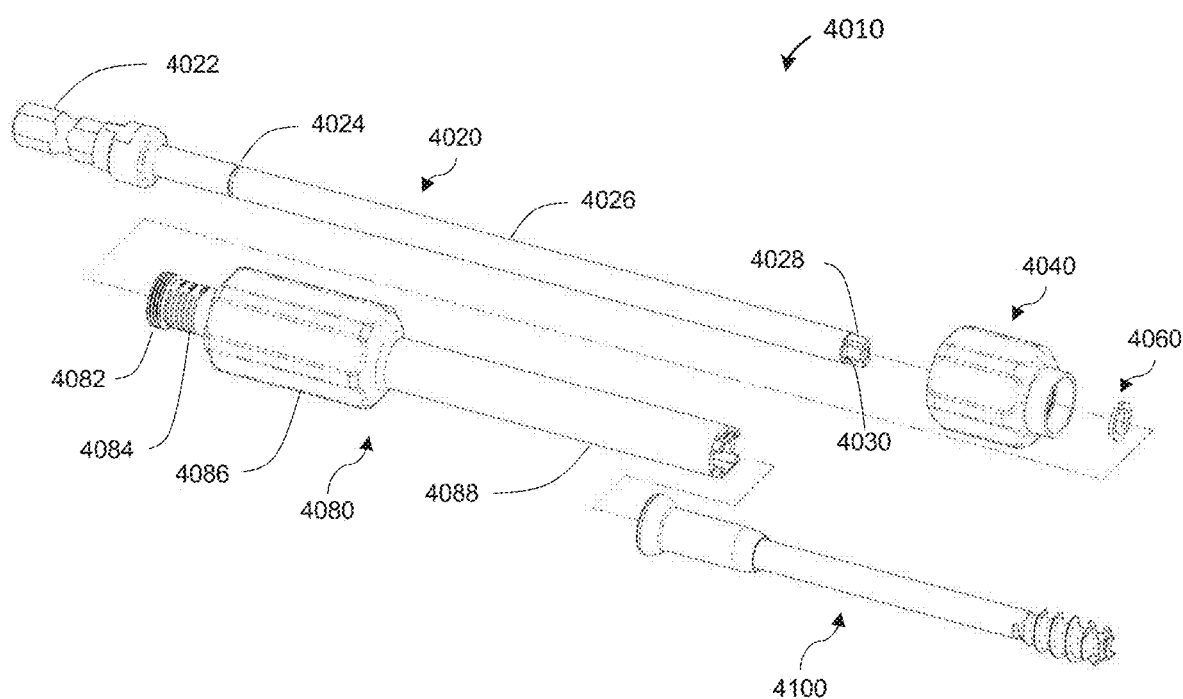
FIG. 32 is an exploded perspective view of the bone screw and the pre-stretch driver shown in FIG. 31.
Figure 34A:
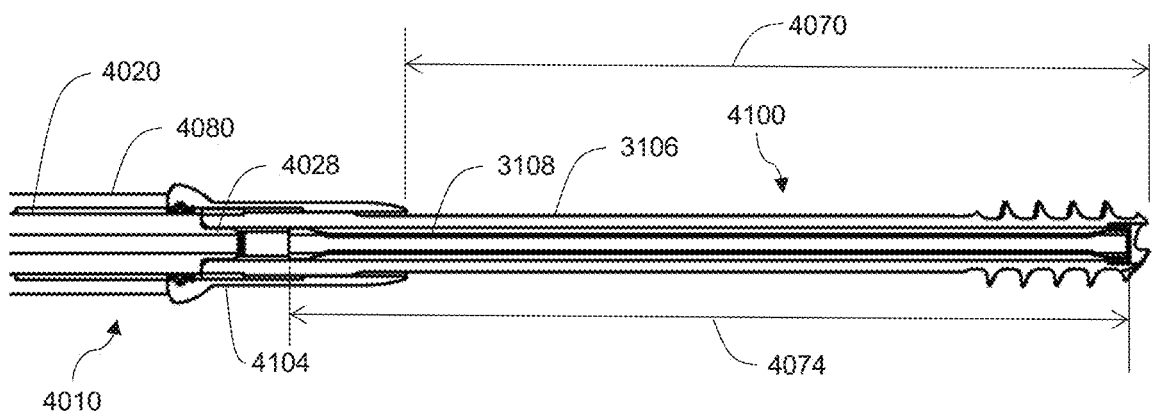
FIGS. 34A and 34B are side elevation, section views of the bone screw and the pre-stretch driver shown in FIG. 31 in unstretched and stretched state, respectively.
Figure 34B:
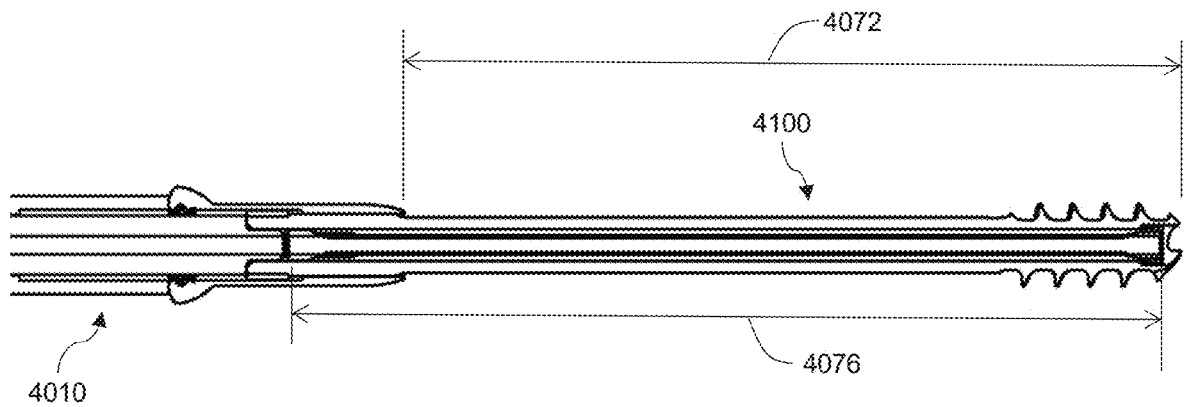
Figure 35A:
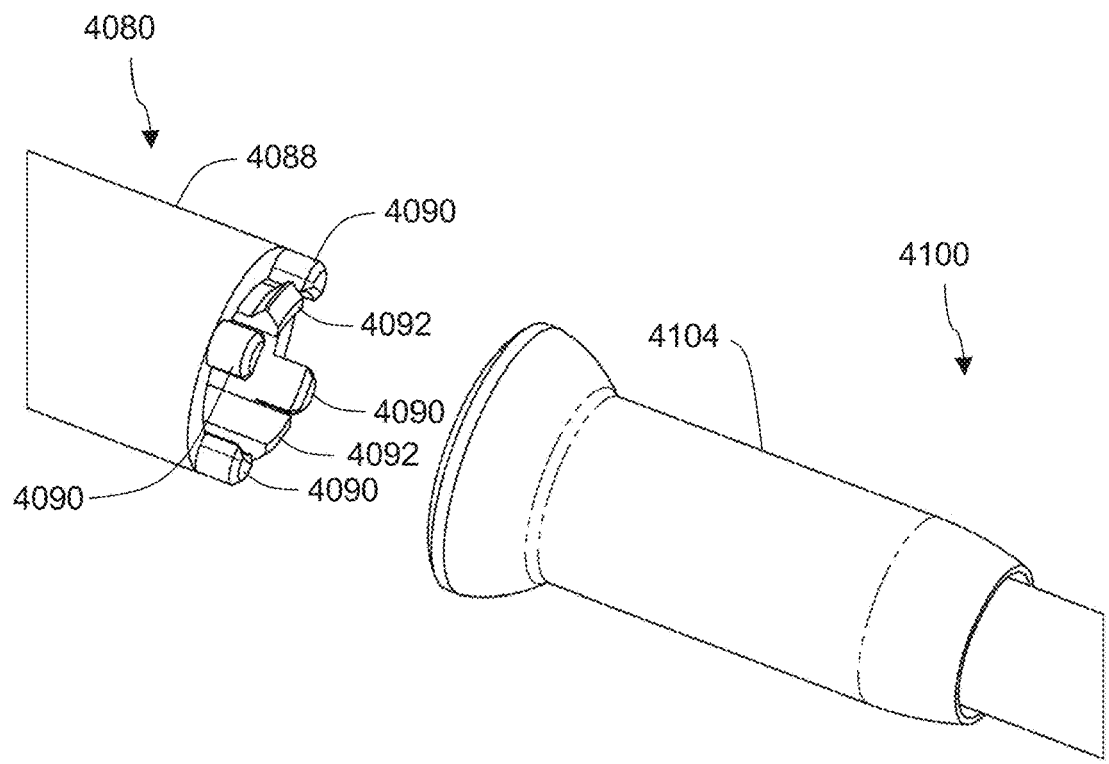
FIGS. 35A and 35B are exploded perspective views of the proximal end of the bone screw and the distal end of a sleeve of the pre-stretch driver shown in FIG. 31.
Figure 35B:
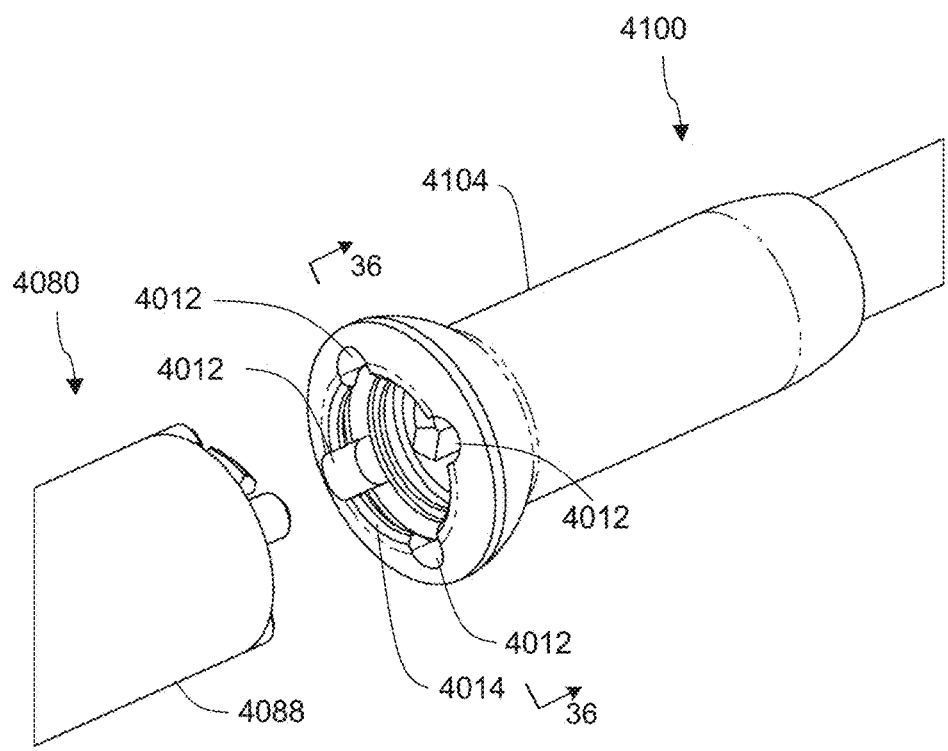
Figure 36:
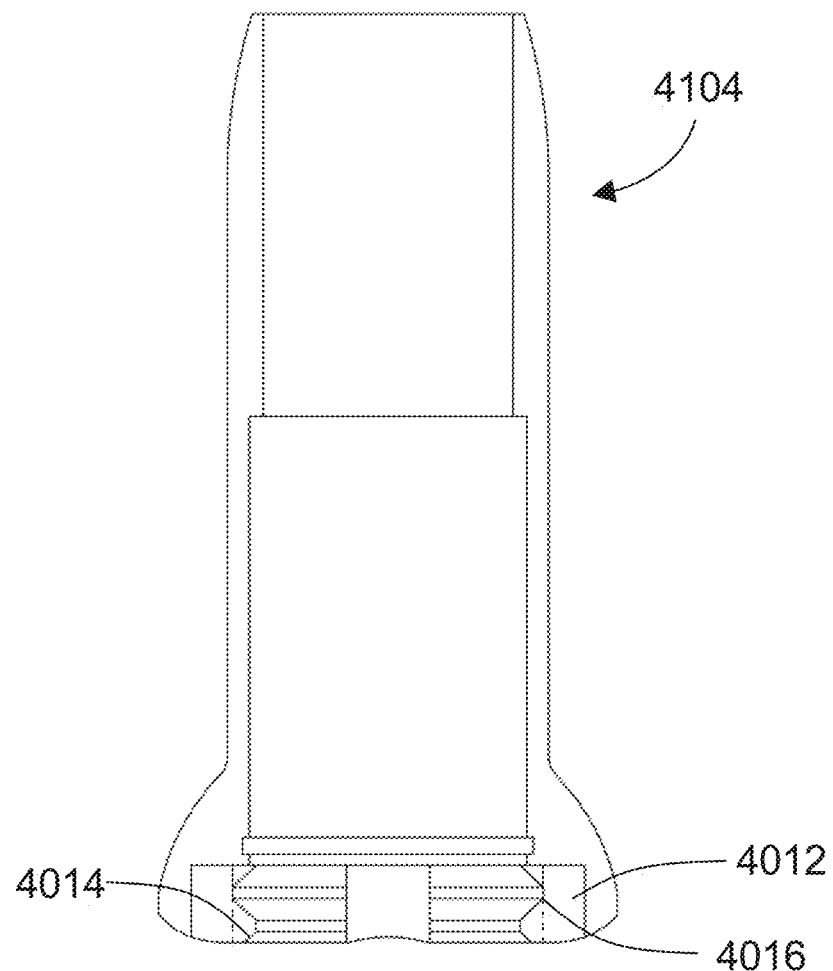
FIG. 36 is a side elevation, section view of the proximal member shown in FIG. 31.

FIG. 31 is a perspective view of a bone screw 4100 and a pre-stretch driver 4010 according to one embodiment. FIG. 32 is an exploded perspective view of the bone screw 4100 and the pre-stretch driver 4010 shown in FIG. 31. FIG. 33 is a side elevation, section view of the bone screw 4100 and the pre-stretch driver 4010 shown in FIG. 31. FIGS. 34A and 34B are side elevation, section views of the bone screw 4100 and the pre-stretch driver 4010 shown in FIG. 31 in unstretched and stretched state, respectively. FIGS. 35A and 35B are exploded perspective views of the proximal end of the bone screw 4100 and the distal end of a sleeve of the pre-stretch driver 4010 shown in FIG. 31. FIG. 36 is a side elevation, section view of the proximal member 4104 shown in FIG. 31.

FIG. 31 shows a pre-stretch driver 4010 attached to a variable-length bone screw, or bone screw 4100. Bone screw 4100 may share the same components as bone screw 3100, except that bone screw 4100 comprises proximal member 4104 in place of proximal member 3104. Therefore, bone screw 4100 may include proximal member 4104, distal member 3106, tension member 3108, nut 3004, support ring 3006 and retaining ring 3008.

Proximal member 4104 may have the same features and may have the same operation as proximal member 3104 and may include the following additional features. As shown in FIGS. 35B and 36, proximal member 4104 may include recesses 4012 and a countersink 4014 on the proximal end of proximal member 4104. An internal groove 4016 may be located immediately distal to countersink 4014.

In this embodiment, recesses 4012, countersink 4014, internal groove 4016, and driver engagement feature 3230 may all, combined, constitute a driver engagement feature. The driver engagement feature may be configured to mate with the pre-stretch driver 4010 such that the pre-stretch driver 4010 is actuatable to urge the proximal member 4104 to move proximally relative to the distal member 3106 to cause elongation of the tension member 3108 independently of engagement of the bone screw 4100 with the bone.

Driver engagement feature 3230 may act as a push feature in addition to a torque-receiving feature, as the torque output feature 4028 of the pre-stretch driver 4010 may engage the slot of the driver engagement feature 3230 in a manner that allows the torque output feature 4028 to rotate the driver engagement feature 3230 and urge the driver engagement feature 3230 to move distally relative to the remaining elements of the driver engagement feature of the bone screw 4100 (i.e., recesses 4012, countersink 4014, and internal groove 4016). Internal groove 4016 may act as a retention feature that can be retained (e.g., by the clips 4092) to keep the proximal member 4104 from moving distally while the distal member 3106 is urged distally by the torque output feature 4028.

The ability of the distal member 3106 to rotate relative to the proximal member 4104 may provide greater flexibility during insertion of the bone screw 4100 into the bone. Specifically, in some embodiments, the pre-stretch driver 4010 may be used to tension the bone screw 4100 fully (i.e., to the maximum length 4072 and the maximum length 4076). However, in alternative embodiments, the pre-stretch driver 4010 may be used to tension the bone screw 4100 only partway (i.e., to a length between the minimum length 4070 and the maximum length 4072, and between the minimum length 4074 and the maximum length 4076). The bone screw 4100 may then be inserted into the bone in such a partially-stretched state. The torque output feature 4028 may be used to rotate the distal member 3106, causing further elongation of the bone screw 4100 during insertion. The proximal member 4104 may not rotate during this process, reducing friction with the surrounding bone, and enabling the pre-stretch driver 4010 to maintain the desired level of pre-stretch until the tension on the bone screw 4100 imparted by insertion into the bone exceeds the tension applied by the pre-stretch driver 4010.

Advantageously, the slot shape of the driver engagement feature 3230 may enable the driver engagement feature 3230 to slide distally, relative to the torque output feature 4028, allowing the bone screw 4100 to elongate further than the level of pre-stretch provided by the pre-stretch driver 4010, without disengaging the bone screw 4100 from the pre-stretch driver 4010.

As shown in FIG. 32, the pre-stretch driver 4010 may include a driver shaft 4020, a knob 4040, a retaining ring 4060, and a sleeve 4080. Driver shaft 4020 may have a torque input feature 4022 near its proximal end, a torque output feature 4028 near its distal end, and a shaft 4026 extending therebetween. An external groove 4024 may be located on the shaft 4026, and a distal shoulder 4030 may be located immediately proximal to torque output feature 4028.

Torque output feature 4028 is shown generally in the form of a blade-shape to engage the driver engagement feature 3230 of distal member 3106 that is generally in the form of a pair of slots formed in opposing sidewalls of the proximal end of the distal member 3106 of the bone screw 4100. However, as mentioned previously, other shapes for transmitting torque between a driver and an implant are known in the art, including but not limited to cruciate shapes, polygonal shapes, hexalobular shapes, and/or the like; any of the foregoing may be used in alternative embodiments.

Sleeve 4080 may have external threads 4082 located near its proximal end, a shaft 4088 located near its distal end, and a handle 4086 extending therebetween. Scale 4084 may be located just distal to external threads 4082 on sleeve 4080. Protrusions 4090 and clips 4092 extend from the distal end of sleeve 4080. Clips 4092 may have elastic resiliency in a radial direction transverse to a long axis of the sleeve 4080.

When the pre-stretch driver 4010 is connected to the bone screw 4100, protrusions 4090 are engaged in recesses 4012 to facilitate transmission of torque (or counter-torque). The protrusions 4090 and recesses 4012 are shown in a radial pattern of four instances, but any complementary positive and negative shape that effectively transmits torque may be used. Protrusions can reside on either pre-stretch driver 4010 or bone screw 4100, with complementary recesses on the other of pre-stretch driver 4010 and bone screw 4100.

As in previous embodiments, the proximal end (e.g., the "head") of proximal member 4104 may take any of the forms shown in FIGS. 24A, 24B, and 24C. Thus, in some embodiments, proximal member 4104 may be modified to have threading and/or a proximal-facing surface that is nonperpendicular to the longitudinal axis of the bone screw 4100. If needed, the interfacing features of the pre-stretch driver 4010 may be modified to accommodate such a design change, allowing pre-stretch of such bone screw embodiments.

Returning to FIG. 32, when the pre-stretch driver 4010 is connected to the bone screw 4100, clips 4092 may be engaged in internal groove 4016. To facilitate assembly of the pre-stretch driver 4010 to the bone screw 4100, countersink 4014 on proximal member 4104 may include an angled surface that will urge the clips 4092 to deflect inward radially, until the clips 4092 spring back outward radially to engage internal groove 4016 when the pre-stretch driver 4010 is fully seated against the proximal end of bone screw 4100 and protrusions 4090 of sleeve 4080 are received in recesses 4012 of proximal member 4104.

The knob 4040 may be pre-assembled to driver shaft 4020 by sliding the knob 4040 over the distal end of driver shaft 4020 and then positioning the knob 4040 adjacent to torque input feature 4022. Then, retaining ring 4060 may be assembled to external groove 4024 on driver shaft 4020 to retain knob 4040 on driver shaft 4020.

To attach the pre-stretch driver 4010 to the bone screw 4100, the sleeve 4080 may be attached to the proximal member 4104 of bone screw 4100 so that clips 4092 are engaged in internal groove 4016 and protrusions 4090 of sleeve 4080 are received in recesses 4012 of proximal member 4104, as described above. Then, driver shaft 4020 with knob 4040 (for example, pre-assembled on driver shaft 4020) may be inserted into the proximal end of sleeve 4080 and advanced distally until torque output feature 4028 is engaged in driver engagement feature 3230 of distal member 3106. Then, internal threads 4044 of knob 4040 may be engaged with external threads 4082 to couple the driver shaft 4020, knob 4040, and sleeve 4080 together.

This assembly of the pre-stretch driver 4010 may retain pre-stretch driver 4010 to bone screw 4100. Specifically, shaft 4026 extends through the space between clips 4092 when the pre-stretch driver 4010 is assembled to bone screw 4100, clips 4092 are prevented from flexing radially inward and from releasing from internal groove 4016, so that the attachment between the pre-stretch driver 4010 and the bone screw 4100 is secured. The distal end of knob 4040 can then be referenced against scale 4084 to indicate the remaining amount of linear change, or stretch, of an overall length of bone screw 4100.

When the pre-stretch driver 4010 is attached to the bone screw 4100 with the bone screw 4100 at its shortest length as shown in FIG. 34A, the distance between the distal end of the proximal member 4104 and the distal end of the distal member 3106 may be at minimum length 4070 and the length of tension member may be at minimum length 4074. To stretch the bone screw 4100, knob 4040 may be rotated clockwise to advance the external threads 4082 distally relative to internal threads 4044, causing inner shoulder 4042 of knob 4040 to bear against assembled retaining ring 4060, thus causing sleeve 4080 and attached proximal member 4104 to advance proximally relative to distal member 3106 and thus stretching tension member 3108. Scale 4084 may show increasing stretch (for example, from the "0" marking of FIG. 32 to the "2" marking, to the "4"

marking, with intervening markings to show smaller increments). The markings of the scale 4084 may represent millimeters of stretch.

Continued relative rotation of knob 4040 with respect to driver shaft 4020 may continue to stretch the variable length screw until length limiting mechanism 3210 is engaged so that maximum length 3262 is achieved, resulting in a distance between the distal end of the proximal member 4104 and distal member 3106 is at maximum length 4072 and the length of tension member is at maximum length 4076. In some embodiments, pre-stretch driver 4010 may be used to pre-stretch bone screw 4100 to the maximum length 3262. In alternative embodiments (for example, where compression over a smaller displacement is sufficient), pre-stretch driver 4010 may be used to pre-stretch bone screw 4100 to an intermediate length between minimum length 3260 and maximum length 3262.

Pre-stretch driver 4010 may operate to not only pre-stretch bone screw 4100, but also to facilitate insertion of bone screw 4100 into bone in the pre-stretched configuration. With bone screw 4100 at the desired pre-stretch length, pre-stretch driver 4010 and bone screw 4100 may be retained together, as described above, until pre-stretch driver 4010 has been activated to release pre-stretch of bone screw 4100. Torque input feature 4022 of pre-stretch driver 4010 may be connected to a torquing device, such a chuck on a motorized drill or manual handle. The torquing device may be used to rotate bone screw 4100, in the pre-stretched configuration, into the hole in the first and second bone portions, until the screw 4100 has reached its desired position. Then, pre-stretch driver 4010 may be disconnected from the torquing device and activated to release the pre-stretch.

To release the pre-stretch driver 4010 from bone screw 4100, such as after placement of pre-stretched bone screw 4100 into bone portions, knob 4040 may be rotated counterclockwise relative to driver shaft 4020 until internal threads 4044 are disengaged from external threads 4082. This may cause the pre-stretch driver 4010 to cease maintaining pre-stretch of the bone screw 4100, allowing bone screw 4100 to apply compression to the bone (i.e., compressing the first and second bone portions together as in previous embodiments). However, bone screw 4100 may still retain pre-stretch to the extent that reactionary forces in the first and second bone portions urge it to remain elongated. As with other bone screws disclosed herein, the bone screw 4100 may be inserted incrementally, with visual, fluoroscopic, and/or other verification of the position of the bone screw 4100 used between advancements to confirm its position.

With the bone screw 4100 inserted to the desired depth within the first and second bone portions and with the pre-stretch released as described above, pre-stretch driver may be disassembled and removed from bone screw 4100. With the internal threads 4044 disengaged from external threads 4082, driver shaft 4020 may be withdrawn from sleeve 4080. Sleeve 4080 may then be disengaged from proximal member 4104 by pulling sleeve 4080 proximally away from proximal member 4104, causing clips 4092 to flex radially inward to release from internal groove 4016.

When the pre-stretch driver 4010 is assembled and in engagement with bone screw 4100, distal shoulder 4030 of driver shaft 4020 may bear directly on the proximal surface 3184 of distal member 3106, which may advantageously directly transmit end loads applied by the user to the pre-stretch driver 4010 (e.g. compressive loads applied by pushing the pre-stretch driver 4010 distally) to distal bone-engaging threads 3122 to facilitate insertion of distal bone-engaging threads 3122 into the bone. This direct transmission of compressive load may help the surgeon to more directly apply pressure to the distal bone-engaging threads 3122 and/or receive tactile feedback indicating how the bone screw 4100 is seating in the bone, whether the insertion depth is appropriate, etc.

Of course, pre-stretching is optional. In some embodiments (for example, bone screw 3100), a more conventional driver without pre-stretch capability may be used. For example, a driver (not shown) may have a shaft terminating at a flat head (for example, resembling torque output feature 4028 of driver shaft 4020) that directly engages and rotates driver engagement feature 3230 of distal member 3106. Such a driver may also provide direct transmission of compressive loads from the driver to the distal member 3106, and thence to the distal bone-engaging threads 3122, providing the benefits cited above for direct load transmission.

The following discussion regarding FIGS. 37-40 uses bone screw 2100 as an example, but the discussion is equally applicable to all embodiments of bones screws described herein, including bone screw 3100 and bone screw 4100.

Figure 37:
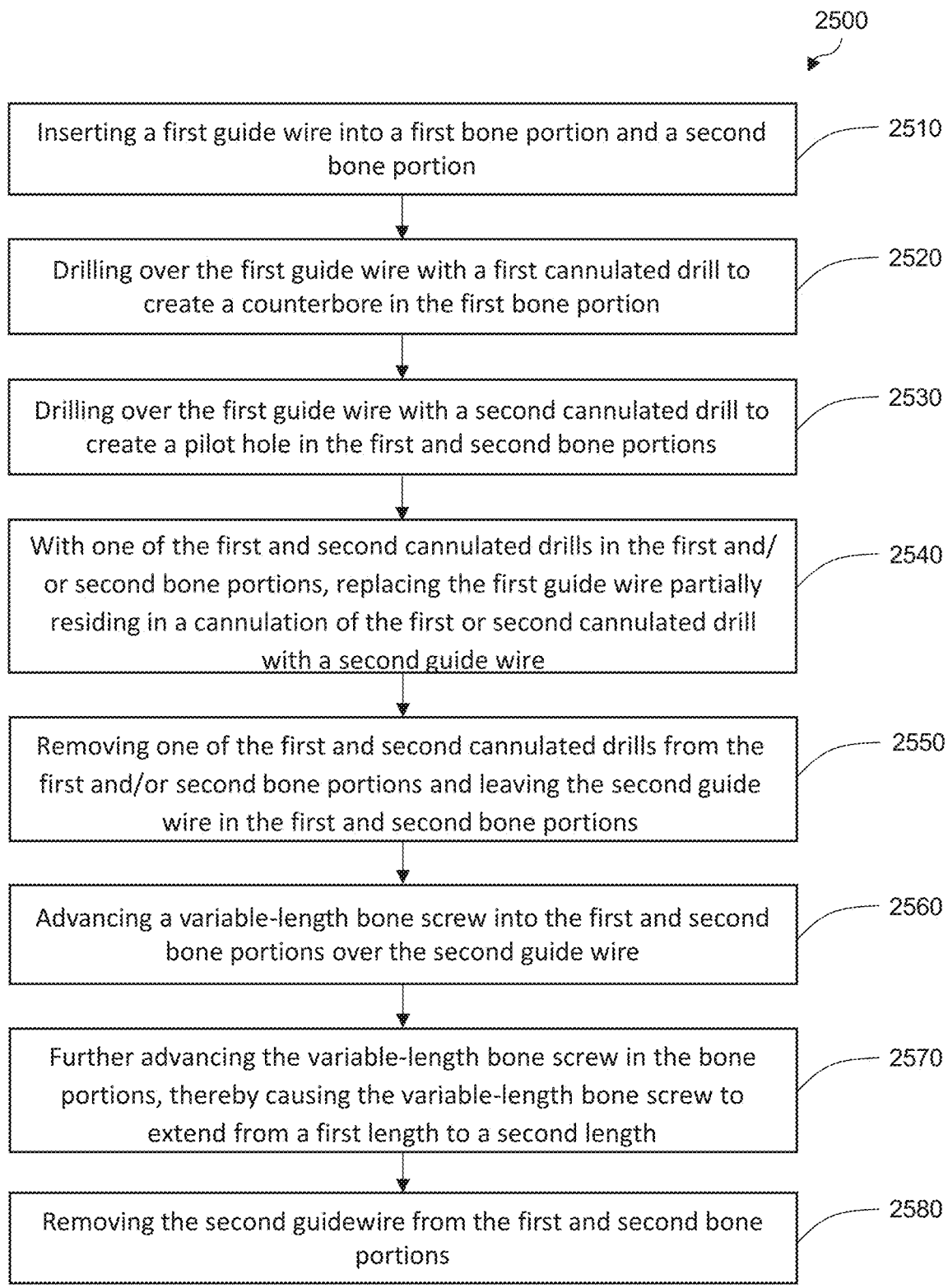
FIG. 37 is a flowchart depicting a method of inserting a variable-length bone screw into bone, according to one embodiment.

FIG. 37 is a flowchart depicting a method of inserting a variable-length bone screw into bone, according to one embodiment. As shown, the method 2500 may commence with a step 2510 in which a first guide wire is inserted into a first bone portion and a second bone portion. Then, in a step 2520, a first cannulated drill may be used to drill over the first guide wire to create a counterbore in the first bone portion. In a step 2530, a second cannulated drill may be used to drill over the first guide wire to create a pilot hole in the first and second bone portions. With one of the first or second cannulated drills in the first and/or second bone portions, step 2540 may be performed in which the first guide wire, partially residing in a cannulation of the first or second cannulated drill, is replaced with a second guide wire, such as a guidewire 2002.

After step 2540, step 2550 may commence, in which one of the first and second cannulated drills is removed from the first and/or second bone portions, thus leaving the second guide wire in the first and second bone portions. Then, a step 2560 may follow, in which a variable-length screw, such as bone screw 2100, is advanced in the first and second bone portions over the second guide wire. Then, a step 2570 may provide for further advancement of the variable-length screw in the bone portions, thereby causing the variable-length screw to extend from a first length, such as minimum length 2260, to a second length, such as maximum length 2262, wherein the second length is longer than the first length. After step 2570, step 2580 may provide for removal of the second guidewire from the first and second bone portions.

Figure 38:
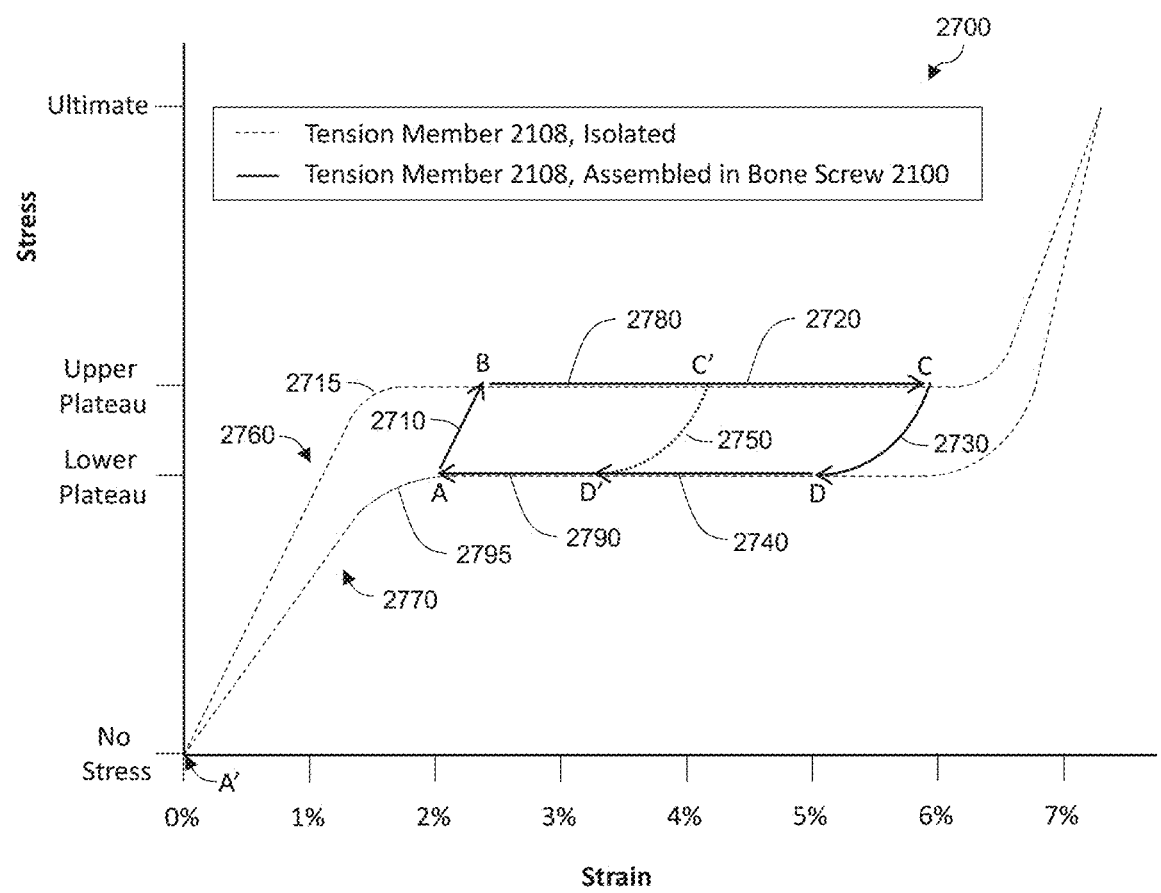
FIG. 38 is a diagram depicting stress versus strain behavior of a tension member according to one embodiment.

FIG. 38 is a diagram 2700 depicting stress versus strain behavior of a tension member according to one embodiment. Diagram 2700 depicts the stress versus strain behavior of tension member 2108 in an isolated state, and as assembled in bone screw 2100 (as shown in FIG. 21A). Upper curve 2760 depicts the stress versus strain behavior of the isolated tension member 2108, such as tension member 2108, as it is loaded from no stress to a stress level just below its ultimate, or failure, stress. Upper curve 2760 may also be called a loading curve. Lower curve 2770 depicts the stress versus strain behavior of the isolated tension member 2108 as it is unloaded from a stress level just below its ultimate stress to zero stress. Lower curve 2770 may also be called an unloading curve.

Tension member 2108, as assembled in bone screw 2100 as shown in FIG. 21A, may have a stress versus strain behavior as depicted by the combination of curve segment A-B 2710, curve segment B-C 2720, curve segment C-D 2730, and curve segment D-A 2740. Point A, also called pre-strain, may represent bone screw 2100 in its minimum length 2260, and point C may represent bone screw 2100 in its maximum length 2262. Point A may be advantageously selected to be in proximity to the left end of the lower plateau stress, or in the range of 1.5% to 2.5% strain as shown in diagram 2700, and more specifically around 2% strain. Point C may be advantageously selected to be in proximity to the right end of the upper plateau stress, or in range of 5.5% to 6.5% strain as shown in diagram 2700, and more specifically around 6% strain.

Advantageously, path shown in FIG. 38 may retain the bone screw in the superelastic range of the tension member 2108. The minimum length 2260 and the maximum length 2262 may be calibrated to accomplish this. Other screws known in the art are inserted with the resilient member unloaded (for example, at point A). Then, the screw must undergo significant elongation (the strain from point A' to point B) before there is appreciable compression on the bone. Then, after the bone screw has compressed the fracture, the bone screw may shorten until the compressive load again falls off (between point A and point A') so that the bone is no longer loaded. The healing benefits of compression may thus not be obtained.

Conversely, the bone screw 2100 may optionally be calibrated such that the bone screw 2100 begins with some pre-tensioning of the tension member 2108. Thus, the bone screw 2100 may begin at or near point A or point B, rather than at point A'. Even if the bone screw 2100 compresses a fracture (or union) enough to reduce the bone screw 2100 back to the minimum length 2260, the bone screw 2100 may continue to apply compression to the bone, at least at or near the lower plateau level. Beneficially, the maximum length 2262 may be selected such that the tension member 2108 cannot be tensioned beyond point C, which could lead to plastic deformation and/or failure of the tension member 2108.

Thus, the tension member 2108 may impart a first compressive force (for example, the lower plateau stress as at point A) between the proximal member and the distal member when the tension member is at the minimum length and a second compression force (for example, the upper plateau stress as at point C) between the proximal member and the distal member when the tension member is at the maximum length. Since point A and point C are at the lower and upper plateau stresses, respectively, the first compression force divided by the second compression force may be similar in value to the lower plateau stress divided by the upper plateau stress.

Alternatively, tension member 2108, as assembled in bone screw 2100 as shown in FIG. 21A, may have a stress versus strain behavior as depicted by the combination of curve segments A-B 2710, curve segment B-C' 2780, curve segment C'-D' 2750, and curve segment D'-A 2790. Point C' may be advantageously selected to be in proximity to the mid-range strain of the upper plateau stress, or in range of 3% to 5% strain as shown in diagram 2700, and preferably around 4% strain. Alternatively, if no pre-strain in the tension member is desired, then tension member 2108, as assembled in bone screw 2100 as shown in FIG. 21A, may have a stress versus strain behavior as depicted by the combination of curve segments A-B 2715, curve segment B-C' 2780, curve segment C'-D' 2750, and curve segment D'-A' 2795.

Bone screw 2100 with a tension member 2108 that is at 0% strain at minimum length 2260 is referred to as a relaxed bone screw (such as a point A' at the origin in diagram 2700), and bone screw 2100 with a tension member 2108 that is at a strain that is in proximity to the left-hand end of a lower plateau stress (such as point A in diagram 2700) at minimum length 2260 is referred to as a pre-strained bone screw. An advantage of a pre-strained bone screw over a relaxed bone screw is that the pre-strained bone screw operates within a much narrower range of stress in the tension member between its minimum length and maximum length, providing more consistent stress over the operable length range. Another advantage of a pre-strained bone screw over a relaxed bone screw is that the pre-strained bone screw has a high level of stress in the tension member even at lengths that are very close to the minimum length, whereas the relaxed bone screw has almost no stress in the tension member at lengths that are very close to the minimum length. Stress in the tension member 2108 is directly proportional to the compression force imparted between the proximal member 2104 and the distal member 2106, which in turn impart that compression between first bone portion 160 and second bone portion 162 as shown in FIGS. 6A and 6B. Thus, compared to a relaxed bone screw, a pre-strained bone screw may provide more consistent compression over its operable length, and may provide a much higher level of compression at lengths that are very close to the minimum length.

Methods of creating pre-strain in tension member 2108 include, but are not limited to, stretching and thermal processing. To create pre-strain by stretching, tension member 2108 may be dimensioned and assembled into bone screw 2100 as shown in FIG. 21A such that, with the tension member in a relaxed state, apertures 2214 in proximal member 2104 are distal to distal shoulder 2217 in distal member 2106 such that pins 2213 cannot be inserted into apertures 2214. Distal member 2106 may be moved distally relative to proximal member 2104 to cause the tension member 2108 to stretch and to cause the distal shoulder 2217 to move distal to apertures 2214, so that pins 2213 may be inserted into the apertures 2214 and into the space on distal member 2106 created by relief 2218, which may then pre-strain the tension member 2108 with a pre-determined amount of strain (for example, the 1.5% to 2.5% strain level referenced above for Point A of FIG. 38).

To create pre-strain by thermal processing, the tension member 2108 with a first length can be made from nitinol and cooled below its martensitic finish temperature. While in the martensitic state, the tension member can be stretched to a second length that is longer than the first length. Because the nitinol is in the martensitic state, deformation may be achieved by a crystal structure twinning effect and the nitinol may remain in its deformed state after it is stretched and released while it remains below the martensitic finish temperature. With the tension member 2108 deformed at the second length and while remaining a temperature below the martensitic finish temperature, the tension member may be assembled into bone screw 2100 as shown in FIG. 21A. After assembly, bone screw 2100 may be heated above its austenitic finish temperature, causing tension member 2108 to attempt to return to its first length, thereby inducing a strain that will be related to the difference in length between the second length and the first length when the bone screw is at minimum length 2260. This induced strain may be the pre-strain identified as point A in diagram 2700 (for example, again amounting to the 1.5% to 2.5% strain level referenced above for Point A of FIG. 38).

Thermal processing may additionally or alternatively be used to help even out insertion and healing compression levels provided by the bone screw 2100. The diagram 2700 shows how hysteresis may cause the bone screw 2100 to apply a lower level of compression to the first and second bone portions after installation, than the level experienced by the surgeon during installation of the bone screw 2100. This may not be desirable, as it may be optimal to maintain a minimum level of compression between the first and second bone portions during the healing process, but with the loss in compressive stress incident to hysteresis, it may not be safe to apply the higher insertion compression needed to obtain the desired level of compression during healing. Thermal processing may be used to help obtain a compression stress that is close to or the same as the insertion stress experienced by the tension member 2108 during insertion, as will be set forth below.

Figure 39:
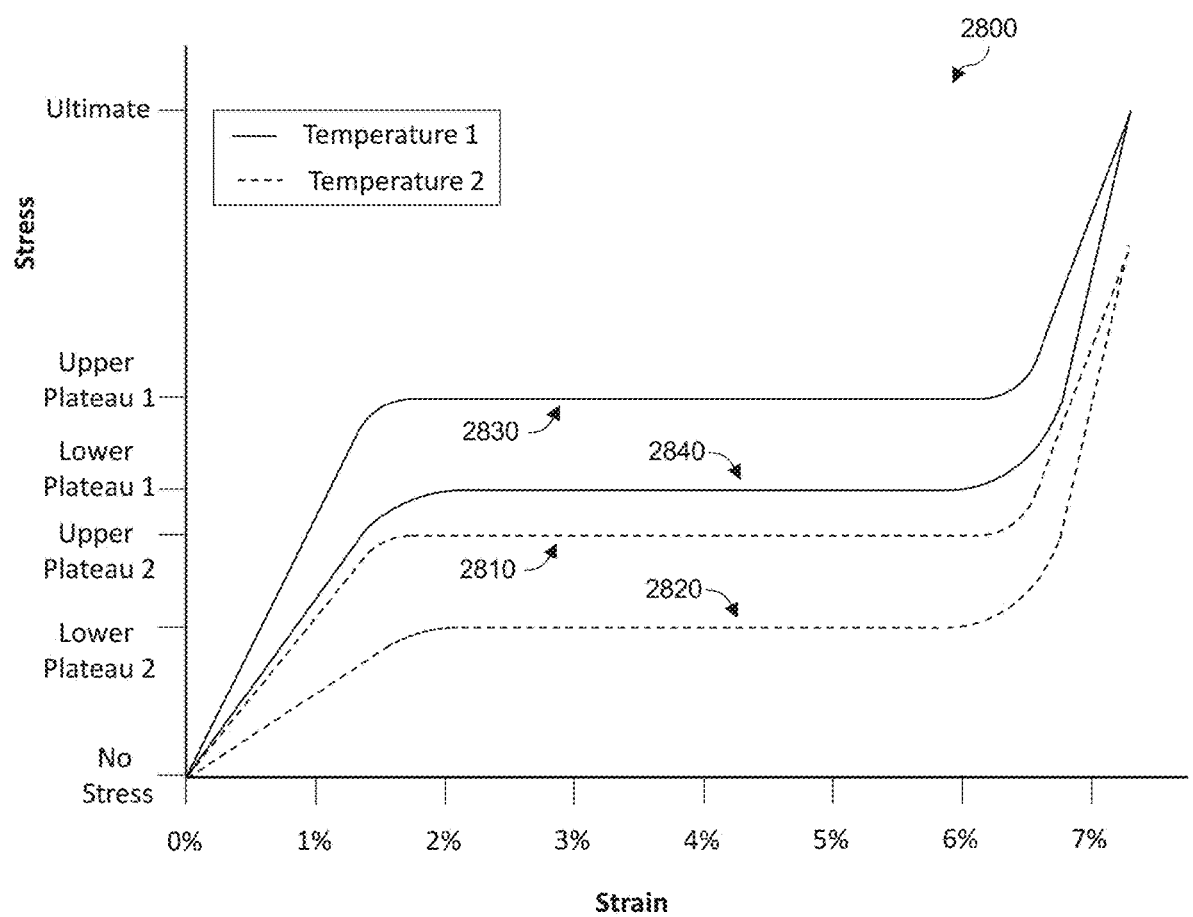
FIG. 39 is a diagram depicting stress versus strain behavior of exemplary superelastic material at two different temperatures.

FIG. 39 is a diagram depicting stress versus strain behavior of exemplary superelastic material at two different temperatures. Superelastic materials, such as nitinol, may have a temperature-dependent stress strain behavior as depicted in diagram 2800. Upper curve 2810 depicts the loading and lower curve 2820 depicts the unloading of a superelastic material at a temperature 2. Upper curve 2830 depicts the loading and lower curve 2840 depicts the unloading of the superelastic material at a temperature 1. Temperature 1 is higher than Temperature 2. For example, experiments performed with a tension member made from superelastic nitinol demonstrated the following upper and lower plateau stresses at 6% strain: at 37° C., 68,000 psi and 46,000 psi (Upper Plateau 1 and Lower Plateau 1, respectively); at 8° ° C., 44,000 psi and 23,000 psi (Upper Plateau 2 and Lower Plateau 2, respectively). Thus, by cooling the tension member 2108 from 37° C. to 8° C., the stress/strain curve may shift from Upper Plateau 2 to Lower Plateau 1 because the 44,000 psi upper plateau stress at the lower temperature is close in value to the 46,000 psi lower plateau stress at the higher temperature (i.e., body temperature).

By inserting bone screw 2100 at 8° C. into first and second bone portions and causing bone screw 2100 to lengthen from minimum length 2260 to a longer length, up to maximum length 2262, the tension member 2108 may stretch at the upper plateau stress of 44,000 psi. After warming to body temperature, tension member 2108 may urge the proximal member 2104 and the distal member 2106 to move toward each other at the lower plateau stress of 46,000 psi. Thus, a compression force, which is proportional to the stress in tension member 2108, imparted by bone screw 2100 on first and second bone portions may be similar, or close in value, for insertion and for maintaining compression between first and second bone portions.

Figure 40:
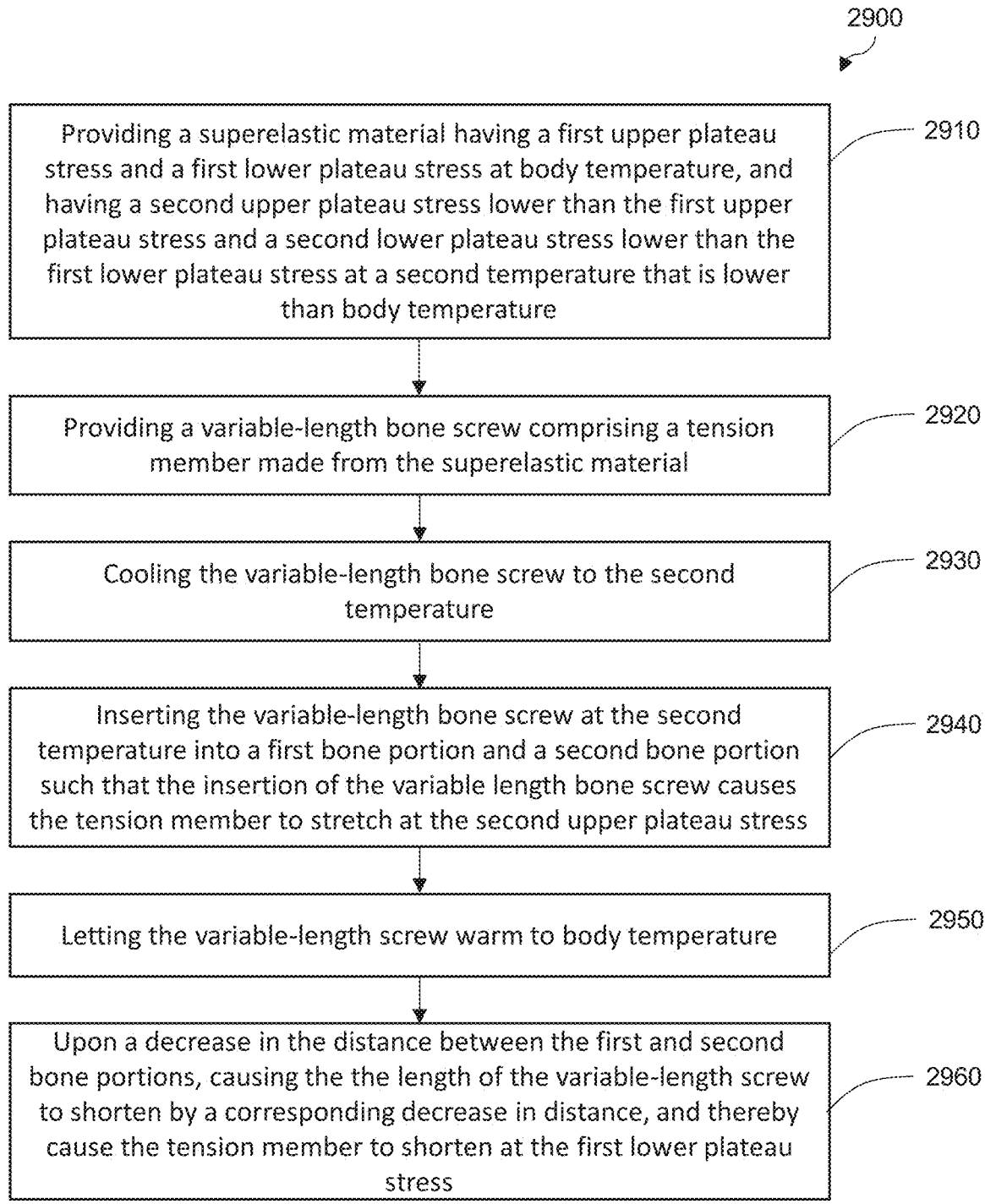
FIG. 40 is a flowchart depicting a method of inserting a variable-length bone screw into bone, according to one embodiment.

FIG. 40 is a flowchart depicting a method of inserting a variable-length bone screw into bone, such as bone screw 2100, according to one embodiment. As shown, the method 2900 may commence with a step 2910 of providing a superelastic material having a first upper plateau stress and a first lower plateau stress at body temperature, and having a second upper plateau stress lower than the first upper plateau stress and a second lower plateau stress lower than the first lower plateau stress at a second temperature that is lower than body temperature. Then, in a step 2920, bone screw 2100 may be provided, with a tension member 2108 made from the superelastic material. The bone screw 2100 may be cooled to the second temperature in step 2930. Once cooled, the bone screw 2100 may be inserted into a first bone portion and a second bone portion such that the insertion of the variable length bone screw causes the tension member 2108 to stretch at the second upper plateau stress in step 2940. Following insertion, the bone screw 2100 may be warmed to body temperature in step 2950 (for example, by natural heat transfer within the body). Once at body temperature, in a step 2960, the bone screw 2100 may shorten by an amount corresponding to the amount of decrease in the distance between first and second bone portions, causing the tension member 2108 to shorten at the first lower plateau stress.

The second temperature may be selected such that the second upper plateau stress and first lower plateau stress are similar in value, so that the compression force generated by the tension member during insertion at the second temperature will be similar to the compressive force generated by the tension member at body temperature as the variable-length screw contracts in length during the healing process. Stresses that are "similar in value" generally means values that differ by less than 25%. In some embodiments, stresses that are similar in value may differ by less than 10%, or more specifically, by less than 5%. Thus, with similar compression forces exerted by the tension member 2108 during and after insertion, the forces imparted by the bone screw 2100 to the first and second bone portions may also be similar during insertion and during length contraction of the variable-length bone screw.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

As used herein, the term "proximal" means a location relatively closer to a user (i.e., a surgeon) when the user is installing the implant. The term "distal" means a location relatively further from the user. For example, when a user installs a bone screw into a material with a driver, the end of the bone screw engaged with the driver is the proximal end, and the tip of the bone screw that first engages the material is the distal end. The term "cannulated" means having a central bore extending along a longitudinal axis of a part between a proximal end and a distal end of the part.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A bone screw insertable into a bone, the bone screw comprising:
   a distal member comprising bone-engaging threads;
   a proximal member configured to slidably engage the distal member; and
   a tension member coupled to the proximal member and the distal member such that, in response to motion of the distal member away from the proximal member, the tension member elongates and urges the distal member to move toward the proximal member;
   wherein:
      the proximal member is further configured to cooperate with the distal member and/or the tension member to define a length limiting mechanism configured to prevent the bone screw from decreasing below a minimum length and from exceeding a maximum length that is greater than the minimum length;
      the tension member is at least partially formed of a superelastic material having an upper plateau stress and a lower plateau stress;
      the tension member imparts a first compressive force between the proximal member and the distal member when the bone screw is at the minimum length and a second compression force between the proximal member and the distal member when the bone screw is at the maximum length; and
      the maximum length is selected such that, at the maximum length, the tension member is at the upper plateau stress;
      the minimum length is selected such that, at the minimum length, the tension member is at the lower plateau stress;
      the length limiting mechanism comprises a distal shoulder, a proximal shoulder, and a stop feature, each of which is on the proximal member, the tension member, and/or the distal member; and
      the stop feature is positioned between the distal shoulder and the proximal shoulder to define the minimum length and the maximum length by abutting the distal shoulder and the proximal shoulder.

2. The bone screw of claim 1, wherein the tension member further comprises a shaft extending from a proximal end to a distal end of the tension member, the shaft comprising a cannula sized to receive a guidewire.

3. The bone screw of claim 1, wherein the proximal member comprises a shank and a head comprising head threading with a first pitch different from a second pitch of the bone-engaging threads.

4. The bone screw of claim 1, wherein:
   the proximal member and the distal member define a longitudinal axis; and
   the proximal member comprises a shank and a head comprising a proximal-most surface that is nonperpendicular to the longitudinal axis.

5. The bone screw of claim 1, wherein:
   the proximal member and the distal member define a longitudinal axis;
   one of the distal member and the tension member comprises a distal engagement surface facing away from the longitudinal axis;
   the proximal member comprises a proximal engagement surface facing toward the longitudinal axis; and
   the distal engagement surface is positioned to abut the proximal engagement surface to transmit bending loads from the distal member to the proximal member without transmission of torque about the longitudinal axis between the distal engagement surface and the proximal engagement surface.

6. The bone screw of claim 1, wherein the tension member is configured such that, at the minimum length of the bone screw, the tension member is pre-stretched so that the tension member is under tension to urge the bone screw to shorten.

7. The bone screw of claim 1, wherein:
   the tension member is further configured to have the upper plateau stress at a first temperature and to have a second lower plateau stress at a second temperature higher than the first temperature; and
   the upper plateau stress is similar in value to the second lower plateau stress.

8. A bone screw insertable into a bone, the bone screw comprising:
   a distal member comprising bone-engaging threads;
   a proximal member configured to slidably engage the distal member and to cooperate with the distal member to define a length limiting mechanism configured to prevent the bone screw from decreasing below a minimum length and from exceeding a maximum length that is greater than the minimum length; and
   a tension member coupled to the proximal member and the distal member such that, in response to motion of the distal member away from the proximal member, the tension member elongates and urges the distal member to move toward the proximal member;
   wherein:
      the tension member is at least partially formed of a superelastic material having an upper plateau stress at a first temperature and a lower plateau stress at a second temperature;
      the bone screw is at the minimum length when the superelastic material is at the lower plateau stress; and
      the bone screw is at the maximum length when the superelastic material is at the upper plateau stress.

9. The bone screw of claim 8, wherein the tension member further comprises a shaft extending from a proximal end to a distal end of the tension member, the shaft comprising a cannula sized to receive a guidewire.

10. The bone screw of claim 8, wherein the proximal member comprises a shank and a head comprising head threading with a first pitch different from a second pitch of the bone-engaging threads.

11. The bone screw of claim 8, wherein:
   the proximal member and the distal member define a longitudinal axis; and
   the proximal member comprises a shank and a head comprising a proximal-most surface that is nonperpendicular to the longitudinal axis.

12. The bone screw of claim 8, wherein:
   the proximal member and the distal member define a longitudinal axis;
   the distal member comprises a distal engagement surface facing away from the longitudinal axis;
   the proximal member comprises a proximal engagement surface facing toward the longitudinal axis; and
   the distal engagement surface is positioned to abut the proximal engagement surface to transmit bending loads from the distal member to the proximal member without transmission of torque about the longitudinal axis between the distal engagement surface and the proximal engagement surface.

13. The bone screw of claim 8, wherein the tension member is configured such that, at the minimum length of the bone screw, the tension member is pre-stretched so that the tension member is under tension to urge the bone screw to shorten.

14. The bone screw of claim 8, wherein the second temperature is an internal body temperature of a patient.

* * * * *